United States Patent
Alten et al.

(10) Patent No.: US 10,874,731 B2
(45) Date of Patent: *Dec. 29, 2020

(54) T CELL RECEPTORS AND IMMUNE THERAPY USING THE SAME

(71) Applicant: immatics biotechnologies GmbH, Tuebingen (DE)

(72) Inventors: Leonie Alten, Tuebingen (DE); Sebastian Bunk, Tuebingen (DE); Dominik Maurer, Moessingen (DE); Claudia Wagner, Tuebingen (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 92 days.

This patent is subject to a terminal disclaimer.

(21) Appl. No.: 15/834,633

(22) Filed: Dec. 7, 2017

(65) Prior Publication Data

US 2018/0161396 A1    Jun. 14, 2018

Related U.S. Application Data

(60) Provisional application No. 62/431,588, filed on Dec. 8, 2016.

(30) Foreign Application Priority Data

Dec. 8, 2016  (DE) .......................... 10 2016 123 847

(51) Int. Cl.

| | | |
|---|---|---|
| A61K 39/00 | (2006.01) | |
| C07K 14/47 | (2006.01) | |
| C07K 14/705 | (2006.01) | |
| A61P 35/00 | (2006.01) | |
| A61K 35/17 | (2015.01) | |
| A61K 38/17 | (2006.01) | |
| C07K 14/725 | (2006.01) | |
| C12N 15/85 | (2006.01) | |
| A61K 38/00 | (2006.01) | |
| C07K 14/73 | (2006.01) | |

(52) U.S. Cl.
CPC ...... *A61K 39/001186* (2018.08); *A61K 35/17* (2013.01); *A61K 38/1764* (2013.01); *A61K 38/1774* (2013.01); *A61K 39/0011* (2013.01); *A61P 35/00* (2018.01); *C07K 14/4748* (2013.01); *C07K 14/705* (2013.01); *C07K 14/7051* (2013.01); *C12N 15/85* (2013.01); *A61K 38/00* (2013.01); *A61K 2039/572* (2013.01); *C07K 14/70514* (2013.01); *C07K 14/70517* (2013.01); *C07K 2317/21* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 2015/0337369 A1 | 11/2015 | Davis et al. | |
| 2017/0267738 A1 | 9/2017 | Maurer et al. | |
| 2018/0161396 A1 | 6/2018 | Alten et al. | |
| 2019/0321478 A1* | 10/2019 | Alten ...................... | A61P 35/00 |

FOREIGN PATENT DOCUMENTS

| | | |
|---|---|---|
| CN | 106 749 620 A | 5/2017 |
| CN | 106749620 A | 5/2017 |
| WO | 2013/039889 A1 | 3/2013 |
| WO | 2014/118236 A2 | 8/2014 |
| WO | 2016011210 A2 | 1/2016 |
| WO | 2017/158103 A1 | 9/2017 |
| WO | 2017/216324 A1 | 12/2017 |
| WO | 2018/170338 A2 | 9/2018 |
| WO | 2019/067242 A1 | 4/2019 |

OTHER PUBLICATIONS

International Search Reporting for PCT/EP2017/081800, dated May 15, 2018.
Database [Online] "*Homo sapiens* (human) partial T cell receptor alpha chain V-J region", XP002778462, retrieved from EBI accession No. EMBL:BAS03561. Jul. 30, 2015.
Gong, Ying et al. "Generation of dual-RMCE-mediated TCR gene replacement system", Chinese Journal of Cell Biology, vol. 37(11): 1481-1489. Nov. 12, 2015.
Obenaus, Matthias et al., "Identification of human T-cell receptors with optimal affinity to cancer antigens using antigen-negative humanized mice", Nature Biotechnology, vol. 33(4): 402-407. Mar. 16, 2015. DOI: 10.1038/nbt.3147. 1----1.
Saeed, Mesha et al., "Targeting melanoma with immunoliposomes coupled to anti-MAGE A1 TCR-like single-chain antibody", International Journal of Nanomedicine. p. 955. Mar. 8, 2016. DOI: 10.2147/IJN.S96123.
Database UniProt [Online] Mar. 4, 2015, XP002778463, retrieved from EBI Accession No. UNIPROT:A0A0B4J275. Database Accession No. A0A0B4J275.

(Continued)

*Primary Examiner* — Peter J Reddig
(74) *Attorney, Agent, or Firm* — McBee Moore & Vanik IP, LLC

(57) ABSTRACT

The present invention pertains to antigen recognizing constructs against tumor associated antigens (MAGEA1). The invention in particular provides novel T cell receptor (TCR) based molecules which are selective and specific for the tumor expressed antigen of the invention. The TCR of the invention, and TAA binding fragments derived therefrom, are of use for the diagnosis, treatment and prevention of TAA expressing cancerous diseases. Further provided are nucleic acids encoding the antigen recognizing constructs of the invention, vectors comprising these nucleic acids, recombinant cells expressing the antigen recognizing constructs and pharmaceutical compositions comprising the compounds of the invention.

15 Claims, 44 Drawing Sheets
(4 of 44 Drawing Sheet(s) Filed in Color)

Specification includes a Sequence Listing.

(56) References Cited

OTHER PUBLICATIONS

Ottaviani, Sabrina et al., "A MAGE-1 antigenic peptide recognized by human cytolytic T lymphocytes on HLA-A2 tumor cells", Cancer Immunology, Immunotherapy, vol. 54(12):1214-1220. Dec. 1, 2005. DOI: 10.1007/S00262-005-0705-2.

German Search Report in corresponding application No. 10 2016 123 847.3, dated Jul. 4, 2017.

Bonini and Mondino (Eur. J. Immunol. 2015 45: 2457-2469) (Year: 2015).

Steffen, Walter et al., "Cutting Edge: Predetermined Avidity of Human CD8 T Cells Expanded on Calibrated MHC/Anti-CD-28-Coated Microspheres", The Journal of Immunology, 2003, pp. 4974-4978, vol. 171.

Blevins, Sydney J. et al., "How structural adaptability exists alongside HLA-A2 bias in the human αβ TCR repertoire", PNAS, Feb. 16, 2016, E1276-E1285.

Cole, David K. et al., "T-cell Receptor (TCR)-Peptide Specificity Overrides Affinity-enhancing TCR-Major Histocompatibility Complex Interactions", The Journal of Biological Chemistry, Jan. 10, 2014, pp. 628-638, vol. 289, No. 2.

Janeway, Jr., Charles A., "Immunobiology: The Immune System in Health and Disease", 5th Edition, 2001, New York: Garland Science.

Wang, Bo et al., "Peptidic Termini Play a Significant Role in TCR Recognition", The Journal of Immunology, 2002, pp. 3137-3145, vol. 169.

Sabrina Ottaviani et al : A MAGE-1 antigenic peptide recognized by human cytolytic T lymphocytes on HLA-A2 tumor cells. Cancer Immunol Immunother (2005) 54: 1214-1220[Abstract, Figs. 2 and 3].

Database EEBL EBI accession No.EMBL : BAS03561 (Laid-open date: Jul. 30, 2015) pp. 1-2 [Entirety].

* cited by examiner

T CELL RECEPTORS AND IMMUNE THERAPY USING THE SAME

CROSS REFERENCE TO RELATED APPLICATIONS

This application claims the benefit of U.S. Provisional Application Ser. No. 62/431,588, filed 8 Dec. 2016, and German Application No. 102016123847.3, filed 8 Dec. 2016, the content of each of these applications is herein incorporated by reference in their entirety.

This application also is related to PCT/EP2017/081800 filed 7 Dec. 2017, the content of which is incorporated herein by reference in its entirety.

REFERENCE TO SEQUENCE LISTING SUBMITTED AS A COMPLIANT ASCII TEXT FILE (.TXT)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2912919-081001_ST25.txt" created on 6 Dec. 2017, and 128,613 bytes in size) is submitted concurrently with the instant application, and the entire contents of the Sequence Listing are incorporated herein by reference.

BACKGROUND

Field

The present invention pertains to antigen recognizing constructs against the tumor associated antigen (TAA) derived peptide MAGEA1-003. The invention in particular provides novel T cell receptor (TCR) based molecules which are selective and specific for the TAA of the invention. The TCR of the invention, and TAA binding fragments derived therefrom, are of use for the diagnosis, treatment and prevention of TAA expressing cancerous diseases. Further provided are nucleic acids encoding the antigen recognizing constructs of the invention, vectors comprising these nucleic acids, recombinant cells expressing the antigen recognizing constructs and pharmaceutical compositions comprising the compounds of the invention.

Description of Related Art

The melanoma antigen genes (MAGE-A) were found to be expressed in a variety of tumors of different histological origin. Proteins encoded by the MAGE genes are tumor rejection anti-gens, which can induce specific cytotoxic T-lymphocytes (CTL) having the ability to recognize and kill cancerous cells. MAGE genes and proteins are thus a preferential target for the development of novel drugs to fight cancer by immunotherapy. MAGE-A proteins constitute a sub-family of Cancer-Testis Antigens which are expressed mainly, but not exclusively, in the germ line. They are however also expressed in various human cancers where they are associated with, and may drive, malignancy. This specific expression of MAGE antigens in tumors and not the normal surrounding healthy tissue makes this family of antigens very interesting for targeted adoptive T cell transfer. However, to date no satisfactory immune therapy is known due to the lack of specific and highly avid antibodies or T cell receptors targeting the MAGE antigen.

T-cell based immunotherapy targets represent peptide epitopes derived from tumor-associated or tumor-specific proteins, which are presented by molecules of the major histocompatibility complex (MHC). These tumor associated antigens (TAAs) can be peptides derived from all protein classes, such as enzymes, receptors, transcription factors, etc. which are expressed and, as compared to unaltered cells of the same origin, usually up-regulated in cells of the respective tumor.

Specific elements of the cellular immune response are capable of selectively recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defective ribosomal products (DRiPs) located in the cytosol, play an important role in this response. The MHC-molecules of the human are also designated as human leukocyte-antigens (HLA).

There are two classes of MHC-molecules, MHC class I and MHC class II. Complexes of peptide and MHC class I are recognized by CD8-positive T-cells bearing the appropriate T-cell receptor (TCR), whereas complexes of peptide and MHC class II molecules are recognized by CD4-positive-helper-T-cells bearing the appropriate TCR. Since both types of response, CD8 and CD4 dependent, contribute jointly and synergistically to the anti-tumor effect, the identification and characterization of tumor-associated antigens and corresponding T cell receptors is important in the development of cancer immunotherapies such as vaccines and cell therapies.

In the MHC class I dependent immune reaction, peptides not only have to be able to bind to certain MHC class I molecules expressed by tumor cells, they subsequently also have to be recognized by T-cells bearing specific T-cell receptors (TCR). There-fore, TAAs are a starting point for the development of a T-cell based therapy including but not limited to tumor vaccines and cell therapies.

Approximately 90 percent of peripheral blood T cells express a TCR consisting of an a polypeptide and a β polypeptide. Beside αβ T cells, a small percentage of T cells (about 5% of total T cells) have been shown to express a TCR consisting of a γ polypeptide and a δ polypeptide. γδ T cells are found at their highest abundance in the gut mucosa, within a population of lymphocytes known as intraepithelial lymphocytes (IELs). The antigenic molecules that activate γδ T cells are still widely unknown. However, γδ T cells are not MHC restricted and seem to be able to recognize whole proteins rather than requiring peptides to be presented by MHC molecules on antigen presenting cells, although some recognize MHC class IB molecules. Human Vγ9/Vδ2 T cells, which constitute the major γδ T cell population in peripheral blood, are unique in that they specifically and rapidly respond to a small non-peptidic microbial metabolite, HMB-PP, an isopentenyl pyrophosphate precursor.

The chains of the T cell antigen receptor of a T cell clone are each composed of a unique combination of domains designated variable (V), [diversity (D),] joining (J), and constant (C). In each T cell clone, the combination of V, D and J domains of both the alpha and the beta chains or of both the delta and the gamma chains participates in antigen recognition in a manner which is uniquely characteristic of that T cell clone and defines a unique binding site, also known as the idiotype of the T cell clone. In contrast, the C domain does not participate in antigen binding.

A TCR is a heterodimeric cell surface protein of the immunoglobulin super-family, which is associated with invariant proteins of the CD3 complex involved in mediating signal transduction. TCRs exist in αβ and γδ forms, which are structurally similar but have quite distinct anatomical locations and probably functions. The extracellular portion of native heterodimeric αβTCR and γδTCR each contain two polypeptides, each of which has a membrane-proximal constant domain, and a membrane-distal variable domain. Each of the constant and variable domains includes an intra-chain disulfide bond. The variable domains contain the highly polymorphic loops analogous to the complementarity determining regions (CDRs) of antibodies. The use of TCR gene therapy overcomes a number of current hurdles. It allows equipping patients' own T cells with desired specificities and generation of sufficient numbers of T cells in a short period of time, avoiding their exhaustion. The TCR will be transduced into central memory T cells or T cells with stem cell characteristics, which may ensure better persistence and function upon transfer. TCR-engineered T cells will be infused into cancer patients rendered lymphopenic by chemotherapy or irradiation, allowing efficient engraftment but inhibiting immune suppression.

SUMMARY

While advances have been made in the development of molecular-targeting drugs for cancer therapy, there remains a need in the art to develop new anti-cancer agents that specifically target molecules highly specific to cancer cells. The present description addresses that need by providing novel MAGEA1 TCRs, respective recombinant TCR constructs, nucleic acids, vectors and host cells that specifically bind TAA epitope(s) as disclosed; and methods of using such molecules in the treatment of cancer. The term TAA in context of the invention relates in particular to the following preferred proteins, namely MAGEA1 proteins, fragments thereof, in particular antigenic peptides presented by HLA, and preferably associated with a proliferative disorder. The preferred antigenic peptide of the invention is the peptide MAGEA1-003, having the amino acid sequence set forth in any of the SEQ ID NO: 133 to 142 and 154 to 162 in table 2 below. A TAA peptide preferably is a peptide as set forth in any of SEQ ID NO: 133 to 142 and 154 to 162.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1: IFNγ release from CD8+ T-cells electroporated with alpha and beta chain RNA of TCR R26P1A9 (SEQ ID NO:1-12) after co-incubation with T2 target cells loaded with MAGEA1-003 peptide (SEQ ID NO:133) or various MAGEA1-003 alanine-substitution variants at positions 1-9 of SEQ ID NO:1 (SEQ ID NO:134-142) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 2: IFNγ release from CD8+ T-cells electroporated with alpha and beta chain RNA of TCR R26P2A6 (SEQ ID NO:13-24) after co-incubation with T2 target cells loaded with MAGEA1-003 peptide (SEQ ID NO:133) or various MAGEA1-003 alanine-substitution variants at positions 1-9 of SEQ ID NO:1 (SEQ ID NO:134-142) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 3: IFNγ release from CD8+ T-cells electroporated with alpha and beta chain RNA of TCR R26P3H1 (SEQ ID NO:25-36) after co-incubation with T2 target cells loaded with MAGEA1-003 peptide (SEQ ID NO:133) or various MAGEA1-003 alanine-substitution variants at positions 1-9 of SEQ ID NO:1 (SEQ ID NO:134-142) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 4: IFNγ release from CD8+ T-cells electroporated with alpha and beta chain RNA of TCR R35P3A4 (SEQ ID NO:37-48) after co-incubation with T2 target cells loaded with MAGEA1-003 peptide (SEQ ID NO:133) or various MAGEA1-003 alanine-substitution variants at positions 1-9 of SEQ ID NO:1 (SEQ ID NO:134-142) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 5: IFNγ release from CD8+ T-cells electroporated with alpha and beta chain RNA of TCR R37P1C9 (SEQ ID NO:49-60) after co-incubation with T2 target cells loaded with MAGEA1-003 peptide (SEQ ID NO:133) or various MAGEA1-003 alanine-substitution variants at positions 1-9 of SEQ ID NO:1 (SEQ ID NO:134-142) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 6: IFNγ release from CD8+ T-cells electroporated with alpha and beta chain RNA of TCR R37P1H1 (SEQ ID NO:61-72) after co-incubation with T2 target cells loaded with
MAGEA1-003 peptide (SEQ ID NO:133) or various MAGEA1-003 alanine-substitution variants at positions 1-9 of SEQ ID NO:1 (SEQ ID NO:134-142) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 7: IFNγ release from CD8+ T-cells electroporated with alpha and beta chain RNA of TCR R42P3A9 (SEQ ID NO:73-84) after co-incubation with T2 target cells loaded with MAGEA1-003 peptide (SEQ ID NO:133) or various MAGEA1-003 alanine-substitution variants at positions 1-9 of SEQ ID NO:1 (SEQ ID NO:134-142) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 8: IFNγ release from CD8+ T-cells electroporated with alpha and beta chain RNA of TCR R43P3F2 (SEQ ID NO:85-96) after co-incubation with T2 target cells loaded with MAGEA1-003 peptide (SEQ ID NO:133) or various MAGEA1-003 alanine-substitution variants at positions 1-9 of SEQ ID NO:1 (SEQ ID NO:134-142) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 9: IFNγ release from CD8+ T-cells electroporated with alpha and beta chain RNA of TCR R43P3G5 (SEQ ID NO:97-108) after co-incubation with T2 target cells loaded with MAGEA1-003 peptide (SEQ ID NO:133) or various MAGEA1-003 alanine-substitution variants at positions 1-9 of SEQ ID NO:1 (SEQ ID NO:134-142) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 10: IFNγ release from CD8+ T-cells electroporated with alpha and beta chain RNA of TCR R59P2E7 (SEQ ID NO:109-120) after co-incubation with T2 target cells loaded with MAGEA1-003 peptide (SEQ ID NO:133) or various MAGEA1-003 alanine-substitution variants at positions 1-9 of SEQ ID NO:1 (SEQ ID NO:134-142) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 11: IFNγ release from CD8+ T-cells electroporated with alpha and beta chain RNA of TCR R26P1A9 (SEQ ID NO:1-12) after co-incubation with T2 target cells loaded with MAGEA1-003 peptide (SEQ ID NO:133) or homologous but unrelated peptide TMEM175-001 (SEQ ID NO:143), EPAS-001 (SEQ ID NO:144), PTRF-001 (SEQ ID NO:145), GALNTL4-001 (SEQ ID NO:146), PSME2-001 (SEQ ID NO:147), KIAA103-002 (SEQ ID NO:148), NSD1-001 (SEQ ID NO:149), TBC1D9-002 (SEQ ID NO:150), TMTC4-001 (SEQ ID NO:151) or RASAL2-002 (SEQ ID NO:152) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 12: IFNγ release from CD8+ T-cells electroporated with alpha and beta chain RNA of TCR R26P2A6 (SEQ ID NO:13-24) after co-incubation with T2 target cells loaded with MAGEA1-003 peptide (SEQ ID NO:133) or homologous but unrelated peptide TMEM175-001 (SEQ ID NO:143), EPAS-001 (SEQ ID NO:144), PTRF-001 (SEQ ID NO:145), GALNTL4-001 (SEQ ID NO:146), PSME2-001 (SEQ ID NO:147), KIAA103-002 (SEQ ID NO:148), NSD1-001 (SEQ ID NO:149), TBC1D9-002 (SEQ ID NO:150), TMTC4-001 (SEQ ID NO:151) or RASAL2-002 (SEQ ID NO:152) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 13: IFNγ release from CD8+ T-cells electroporated with alpha and beta chain RNA of TCR R26P3H1 (SEQ ID NO:25-36) after co-incubation with T2 target cells loaded with MAGEA1-003 peptide (SEQ ID NO:133) or homologous but unrelated peptide TMEM175-001 (SEQ ID NO:143), EPAS-001 (SEQ ID NO:144), PTRF-001 (SEQ ID NO:145), GALNTL4-001 (SEQ ID NO:146), PSME2-001 (SEQ ID NO:147), KIAA103-002 (SEQ ID NO:148), NSD1-001 (SEQ ID NO:149), TBC1D9-002 (SEQ ID NO:150), TMTC4-001 (SEQ ID NO:151) or RASAL2-002 (SEQ ID NO:152) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 14: IFNγ release from CD8+ T-cells electroporated with alpha and beta chain RNA of TCR R35P3A4 (SEQ ID NO:37-48) after co-incubation with T2 target cells loaded with MAGEA1-003 peptide (SEQ ID NO:133) or homologous but unrelated peptide TMEM175-001 (SEQ ID NO:143), EPAS-001 (SEQ ID NO:144), PTRF-001 (SEQ ID NO:145), GALNTL4-001 (SEQ ID NO:146), PSME2-001 (SEQ ID NO:147), KIAA103-002 (SEQ ID NO:148), NSD1-001 (SEQ ID NO:149), TBC1D9-002 (SEQ ID NO:150), TMTC4-001 (SEQ ID NO:151) or RASAL2-002 (SEQ ID NO:152) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 15: IFNγ release from CD8+ T-cells electroporated with alpha and beta chain RNA of TCR R37P1C9 (SEQ ID NO:49-60) after co-incubation with T2 target cells loaded with MAGEA1-003 peptide (SEQ ID NO:133) or homologous but unrelated peptide TMEM175-001 (SEQ ID NO:143), EPAS-001 (SEQ ID NO:144), PTRF-001 (SEQ ID NO:145), GALNTL4-001 (SEQ ID NO:146), PSME2-001 (SEQ ID NO:147), KIAA103-002 (SEQ ID NO:148), NSD1-001 (SEQ ID NO:149), TBC1D9-002 (SEQ ID NO:150), TMTC4-001 (SEQ ID NO:151) or RASAL2-002 (SEQ ID NO:152) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 16: IFNγ release from CD8+ T-cells electroporated with alpha and beta chain RNA of TCR R37P1H1 (SEQ ID NO:61-72) after co-incubation with T2 target cells loaded with MAGEA1-003 peptide (SEQ ID NO:133) or homologous but unrelated peptide TMEM175-001 (SEQ ID NO:143), EPAS-001 (SEQ ID NO:144), PTRF-001 (SEQ ID NO:145), GALNTL4-001 (SEQ ID NO:146), PSME2-001 (SEQ ID NO:147), KIAA103-002 (SEQ ID NO:148), NSD1-001 (SEQ ID NO:149), TBC1D9-002 (SEQ ID NO:150), TMTC4-001 (SEQ ID NO:151) or RASAL2-002 (SEQ ID NO:152) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 17: IFNγ release from CD8+ T-cells electroporated with alpha and beta chain RNA of TCR R42P3A9 (SEQ ID NO:73-84) after co-incubation with T2 target cells loaded with MAGEA1-003 peptide (SEQ ID NO:133) or homologous but unrelated peptide TMEM175-001 (SEQ ID NO:143), EPAS-001 (SEQ ID NO:144), PTRF-001 (SEQ ID NO:145), GALNTL4-001 (SEQ ID NO:146), PSME2-001 (SEQ ID NO:147), KIAA103-002 (SEQ ID NO:148), NSD1-001 (SEQ ID NO:149), TBC1D9-002 (SEQ ID NO:150), TMTC4-001 (SEQ ID NO:151) or RASAL2-002 (SEQ ID NO:152) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 18: IFNγ release from CD8+ T-cells electroporated with alpha and beta chain RNA of TCR R43P3F2 (SEQ ID NO:85-96) after co-incubation with T2 target cells loaded with MAGEA1-003 peptide (SEQ ID NO:133) or homologous but unrelated peptide TMEM175-001 (SEQ ID NO:143), EPAS-001 (SEQ ID NO:144), PTRF-001 (SEQ ID NO:145), GALNTL4-001 (SEQ ID NO:146), PSME2-001 (SEQ ID NO:147), KIAA103-002 (SEQ ID NO:148), NSD1-001 (SEQ ID NO:149), TBC1D9-002 (SEQ ID NO:150), TMTC4-001 (SEQ ID NO:151) or RASAL2-002 (SEQ ID NO:152) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 19: IFNγ release from CD8+ T-cells electroporated with alpha and beta chain RNA of TCR R43P3G5 (SEQ ID NO:97-108) after co-incubation with T2 target cells loaded with MAGEA1-003 peptide (SEQ ID NO:133) or homologous but unrelated peptide TMEM175-001 (SEQ ID NO:143), EPAS-001 (SEQ ID NO:144), PTRF-001 (SEQ ID NO:145), GALNTL4-001 (SEQ ID NO:146), PSME2-001 (SEQ ID NO:147), KIAA103-002 (SEQ ID NO:148), NSD1-001 (SEQ ID NO:149), TBC1D9-002 (SEQ ID NO:150), TMTC4-001 (SEQ ID NO:151) or RASAL2-002 (SEQ ID NO:152) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 20: IFNγ release from CD8+ T-cells electroporated with alpha and beta chain RNA of TCR R59P2E7 (SEQ ID NO:109-120) after co-incubation with T2 target cells loaded with MAGEA1-003 peptide (SEQ ID NO:133) or homologous but unrelated peptide TMEM175-001 (SEQ ID NO:143), EPAS-001 (SEQ ID NO:144), PTRF-001 (SEQ ID NO:145), GALNTL4-001 (SEQ ID NO:146), PSME2-001 (SEQ ID NO:147), KIAA103-002 (SEQ ID NO:148), NSD1-001 (SEQ ID NO:149), TBC1D9-002 (SEQ ID NO:150), TMTC4-001 (SEQ ID NO:151) or RASAL2-002 (SEQ ID NO:152) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0004) is shown on the left Y-axis, donor 2 (TCRA-0005) on the right Y-axis, respectively.

FIG. 21: HLA-A*02/MAGEA1-003 tetramer or HLA-A*02/NYESO1-001 tetramer staining, respectively, of CD8+ T-cells electroporated with alpha and beta chain RNA of TCR R26P2A6 and R26P3H1, respectively. CD8+ T-cells electroporated with RNA of 1G4 TCR that specifically binds to HLA-A*02/NYESO1-001 complex and mock electroporated CD8+ T-cells served as controls.

FIG. 22: IFNγ release from CD8+ T-cells electroporated with alpha and beta chain RNA of TCR R26P1A9 (SEQ ID NO:1-12) after co-incubation with T2 target cells loaded with MAGEA1-003 peptide (SEQ ID NO:133) or various MAGEA1-003 threonine-substitution variants at positions 1-9 of SEQ ID NO:1 (SEQ ID NO:154-162) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0006) is shown on the left Y-axis, donor 2 (TCRA-0007) on the right Y-axis respectively.

FIG. 23: IFNγ release from CD8+ T-cells electroporated with alpha and beta chain RNA of TCR R26P2A6 (SEQ ID NO:13-24) after co-incubation with T2 target cells loaded with MAGEA1-003 peptide (SEQ ID NO:133) or various MAGEA1-003 threonine-substitution variants at positions 1-9 of SEQ ID NO:1 (SEQ ID NO:154-162) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0006) is shown on the left Y-axis, donor 2 (TCRA-0007) on the right Y-axis, respectively.

FIG. 24: IFNγ release from CD8+ T-cells electroporated with alpha and beta chain RNA of TCR R26P3H1 (SEQ ID NO:25-36) after co-incubation with T2 target cells loaded with MAGEA1-003 peptide (SEQ ID NO:133) or various MAGEA1-003 threonine-substitution variants at positions 1-9 of SEQ ID NO:1 (SEQ ID NO:154-162) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0006) is shown on the left Y-axis, donor 2 (TCRA-0007) on the right Y-axis, respectively.

FIG. 25: IFNγ release from CD8+ T-cells electroporated with alpha and beta chain RNA of TCR R35P3A4 (SEQ ID NO:37-48) after co-incubation with T2 target cells loaded with MAGEA1-003 peptide (SEQ ID NO:133) or various MAGEA1-003 threonine-substitution variants at positions 1-9 of SEQ ID NO:1 (SEQ ID NO:154-162) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0006) is shown on the left Y-axis, donor 2 (TCRA-0007) on the right Y-axis, respectively.

FIG. 26: IFNγ release from CD8+ T-cells electroporated with alpha and beta chain RNA of TCR R37P1C9 (SEQ ID NO:49-60) after co-incubation with T2 target cells loaded with MAGEA1-003 peptide (SEQ ID NO:133) or various MAGEA1-003 threonine-substitution variants at positions 1-9 of SEQ ID NO:1 (SEQ ID NO:154-162) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0006) is shown on the left Y-axis, donor 2 (TCRA-0007) on the right Y-axis, respectively.

FIG. 27: IFNγ release from CD8+ T-cells electroporated with alpha and beta chain RNA of TCR R37P1H1 (SEQ ID NO:61-72) after co-incubation with T2 target cells loaded with MAGEA1-003 peptide (SEQ ID NO:133) or various MAGEA1-003 threonine-substitution variants at positions 1-9 of SEQ ID NO:1 (SEQ ID NO:154-162) or control peptide NYESO1-001 (SEQ ID NO:153). IFNγ release data were obtained with CD8+ T-cells derived from one donors. RNA electroporated CD8+ T-cells alone or in co-incubation with unloaded target cells served as controls.

FIG. 28: IFNγ release from CD8+ T-cells electroporated with alpha and beta chain RNA of TCR R42P3A9 (SEQ ID NO:73-84) after co-incubation with T2 target cells loaded with MAGEA1-003 peptide (SEQ ID NO:133) or various MAGEA1-003 threonine-substitution variants at positions 1-9 of SEQ ID NO:1 (SEQ ID NO:154-162) or control peptide NYESO1-001 (SEQ ID NO:153). IFNγ release data were obtained with CD8+ T-cells derived from one donors. RNA electroporated CD8+ T-cells alone or in co-incubation with unloaded target cells served as controls.

FIG. 29: IFNγ release from CD8+ T-cells electroporated with alpha and beta chain RNA of TCR R43P3F2 (SEQ ID NO:85-96) after co-incubation with T2 target cells loaded with MAGEA1-003 peptide (SEQ ID NO:133) or various MAGEA1-003 threonine-substitution variants at positions 1-9 of SEQ ID NO:1 (SEQ ID NO:154-162) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0006) is shown on the left Y-axis, donor 2 (TCRA-0007) on the right Y-axis, respectively.

FIG. 30: IFNγ release from CD8+ T-cells electroporated with alpha and beta chain RNA of TCR R43P3G5 (SEQ ID NO:97-108) after co-incubation with T2 target cells loaded with MAGEA1-003 peptide (SEQ ID NO:133) or various MAGEA1-003 threonine-substitution variants at positions 1-9 of SEQ ID NO:1 (SEQ ID NO:154-162) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0006) is shown on the left Y-axis, donor 2 (TCRA-0007) on the right Y-axis, respectively.

FIG. 31: IFNγ release from CD8+ T-cells electroporated with alpha and beta chain RNA of TCR R59P2E7 (SEQ ID NO:109-120) after co-incubation with T2 target cells loaded with MAGEA1-003 peptide (SEQ ID NO:133) or various MAGEA1-003 threonine-substitution variants at positions 1-9 of SEQ ID NO:1 (SEQ ID NO:154-162) or control peptide NYESO1-001 (SEQ ID NO:153). IFNγ release data were obtained with CD8+ T-cells derived from two different donors. RNA electroporated CD8+ T-cells alone or in co-incubation with unloaded target cells served as controls. Donor 1 (TCRA-0006) is shown on the left Y-axis, donor 2 (TCRA-0007) on the right Y-axis, respectively.

FIG. 32: IFNγ release from CD8+ T-cells electroporated with alpha and beta chain RNA of TCRs R35P3A4 (SEQ ID NO:37-48), R37P1C9 (SEQ ID NO:49-60) and R43P3G5 (SEQ ID NO:97-108) after co-incubation with different tumor cell lines. U266B1 and UACC-257 present the target, KMM-1, NCI-H2023, L-1236, MCF-7 and A-375 do not present the target. T2 target cells loaded with MAGEA1-003 or control peptide NYESO1-001 (SEQ ID NO:153) and RNA electroporated CD8+ T-cells alone served as controls.

FIG. 33: IFNγ release from T-cells after lentiviral transduction with different constructs containing alpha and beta chain of TCRs R35P3A4 (SEQ ID NO:37-48; constructs R35D, R35G), R37P1C9 (SEQ ID NO:49-60; constructs R37D, R37G) and R43P3G5 (SEQ ID NO:97-108; constructs R43A, R43H) after co-incubation with different primary cells and iPSC-derived cell types. U266B1 and UACC-257 and T-cells alone served as controls.

| Cell type | Abbreviation | source |
|---|---|---|
| Normal Human Dermal Fibroblasts | NHDF | Primary cells |
| Human Coronary Artery Smooth Muscle Cells | HCASMC | Primary cells |
| Human Tracheal Smooth Muscle Cells | HTSMC | Primary cells |
| Human Renal Epithelial Cells | HREpC | Primary cells |
| Human Cardiomyocytes | HCM | Primary cells |
| Human Cardiac Microvascular Endothelial Cells | HCMEC | Primary cells |
| iCell Hepatocytes 2.0 | — | iPSC-derived cells |
| iCell Astrocytes | — | iPSC-derived cells |
| iCell Neurons | — | iPSC-derived cells |

Figure 34:
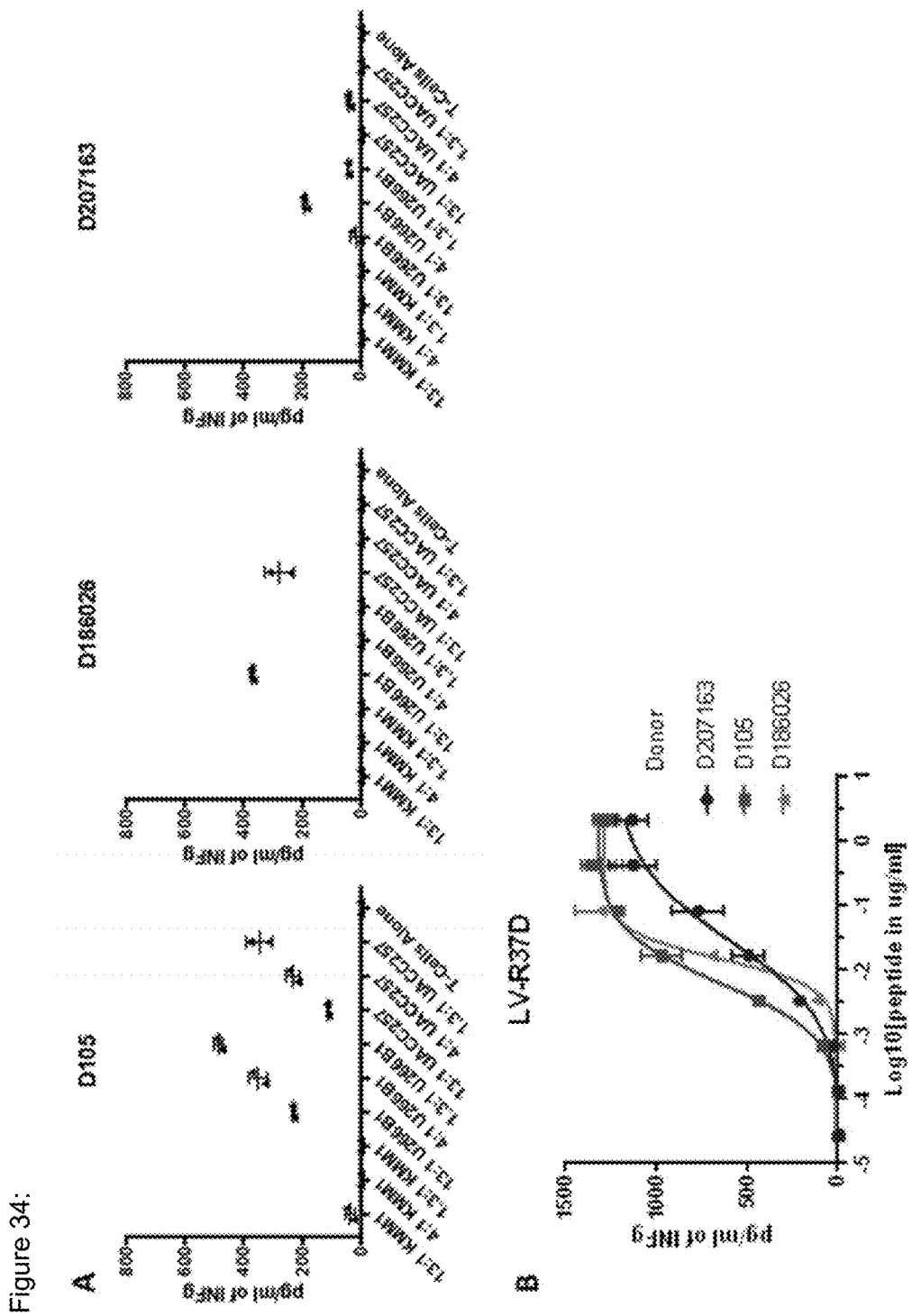

FIG. 34: IFNγ release from T-cells after lentiviral transduction with different constructs containing alpha and beta chain of TCR R37P1C9 to assess LV-R37D-mediated recognition of endogenously processed and presented MAGEA1-003. (A) T cells from three healthy donors, non-transduced (NT) or transduced with LV-R37D were co-cultured with 3 different tumor cell lines. IFN-γ production with HLA-A*02+ tumor cell lines endogenously expressing MAGEA1 (UACC257 and U266B1) or lacking surface-presented (KMM1). E:T targets are indicated. (B) IFN-γ production with serially diluted MAGEA1 peptide pulsed T2 cells. Co-cultures were set up at E:T ratio 4:1 (60,000 T cells; 15,000 T2 cells). Mean and standard deviation of IFN-γ released after 20 h from three replicates (donors) is shown as duplicate measurements by ELISA.

Figure 35:
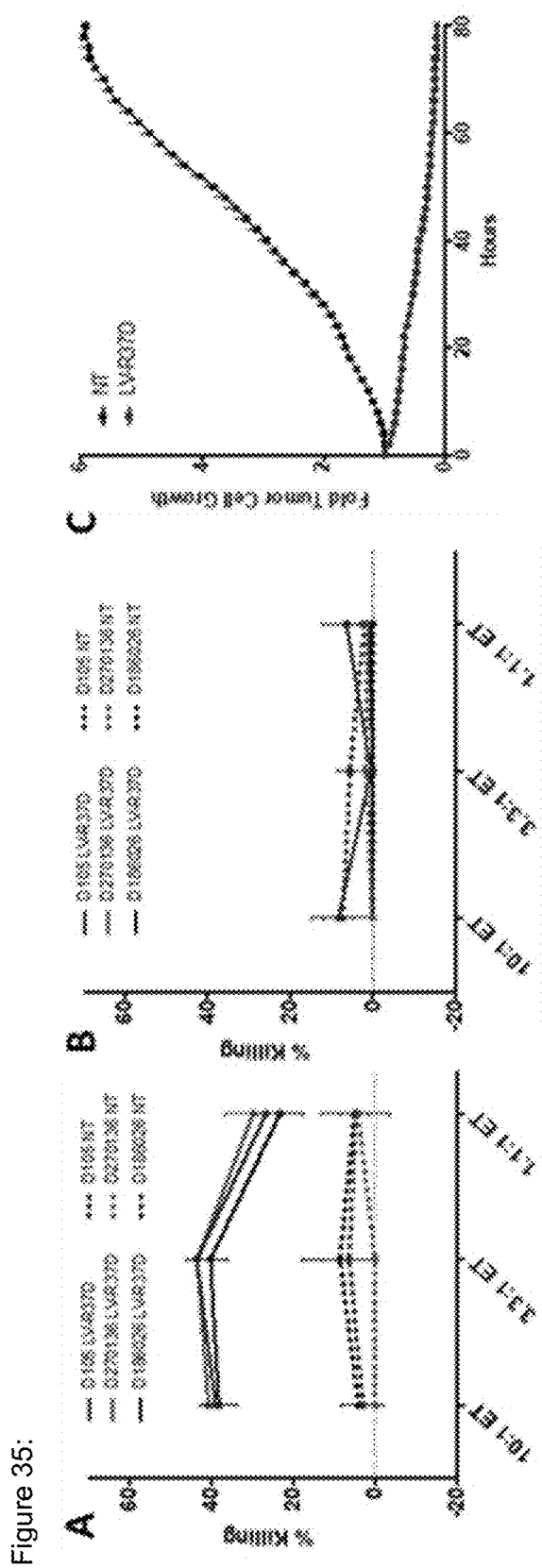

FIG. 35: Potency assay evaluating cytolytic activity of lentivirally transduced T cells expressing TCR R37P1C9 (construct R37D) against MAGEA1+ tumor cells. Cytotoxic response of LV-R37D transduced and non-transduced (NT) T cells measured against (A) U138MG MAGEA1+ tumor cells (HLA-A*02+), (B) U138MG MAGEA1− (HLA-A*02+), or (C) U2-OS MAGEA1+(HLA-A*02+) tumor cells. The assays were performed at various E:T ratios (A and B) or at 10:1 E:T ratio (C) in a 96 hour fluorescence microscopy based cytotoxicity assay. Results are presented as mean±SD of 3 replicates. NT—Non-transduced. For graphs A and B, % Killing=(Area-Under-Curve of experiment sample with T cells/Area-Under-Curve tumor targets alone)*100, where Area-Under-Curve is calculated from the longitudinal growth measurements as shown in graph C; negative % Killing values are set to 0.

Figure 36:
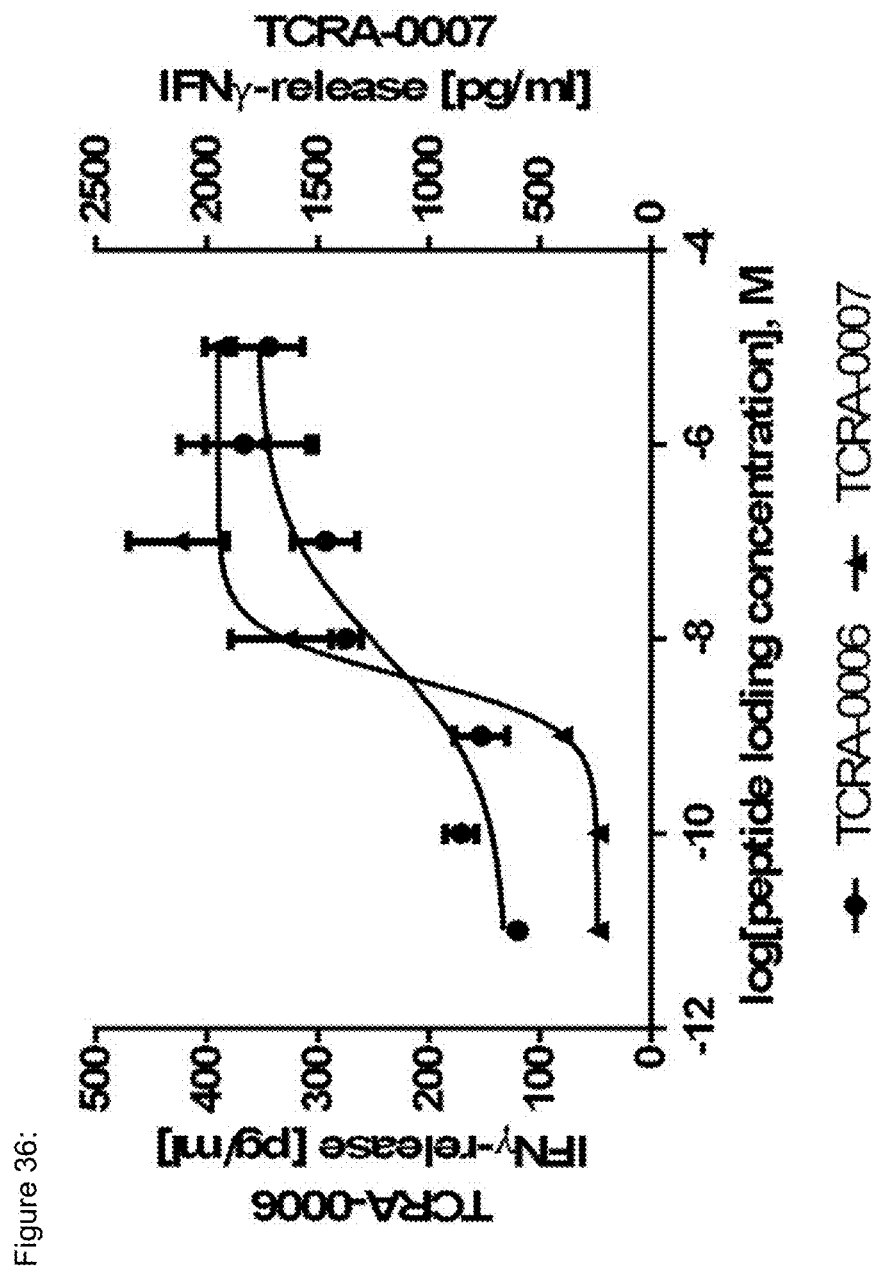

FIG. 36: IFNγ release from CD8+ T-cells electroporated with alpha and beta chain RNA of TCR R26P1A9 (Table 1) after co-incubation with T2 target cells loaded with MAGEA1-003 peptide (SEQ ID NO:133) in various peptide loading concentrations from 10 μM to 10 μM. IFNγ release data were obtained with CD8+ T-cells derived from two different healthy donors.

Figure 37:
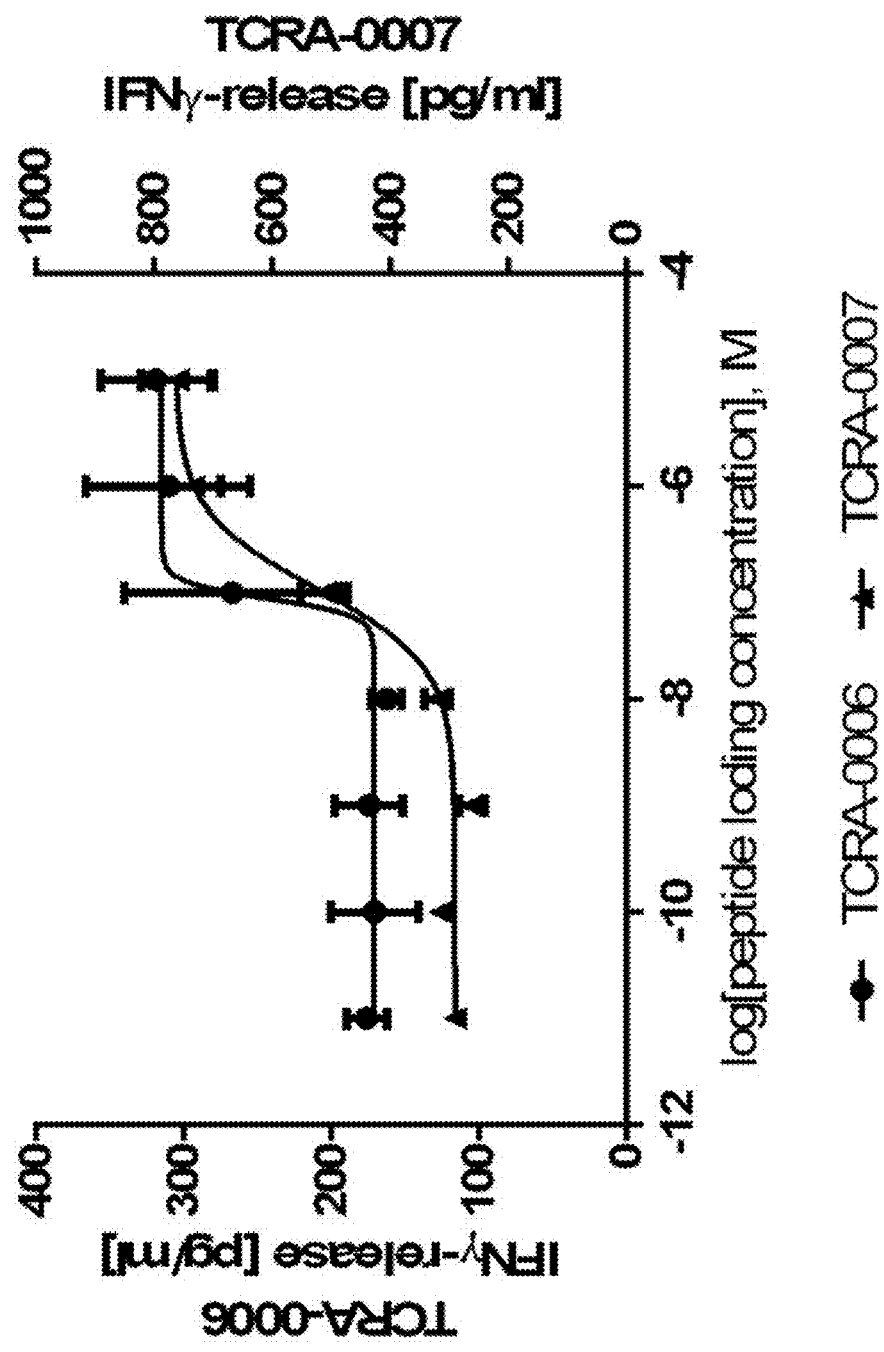

FIG. 37: IFNγ release from CD8+ T-cells electroporated with alpha and beta chain RNA of TCR R26P2A6 (Table 1) after co-incubation with T2 target cells loaded with MAGEA1-003 peptide (SEQ ID NO:133) in various peptide loading concentrations from 10 μM to 10 pM. IFNγ release data were obtained with CD8+ T-cells derived from two different healthy donors.

Figure 38:
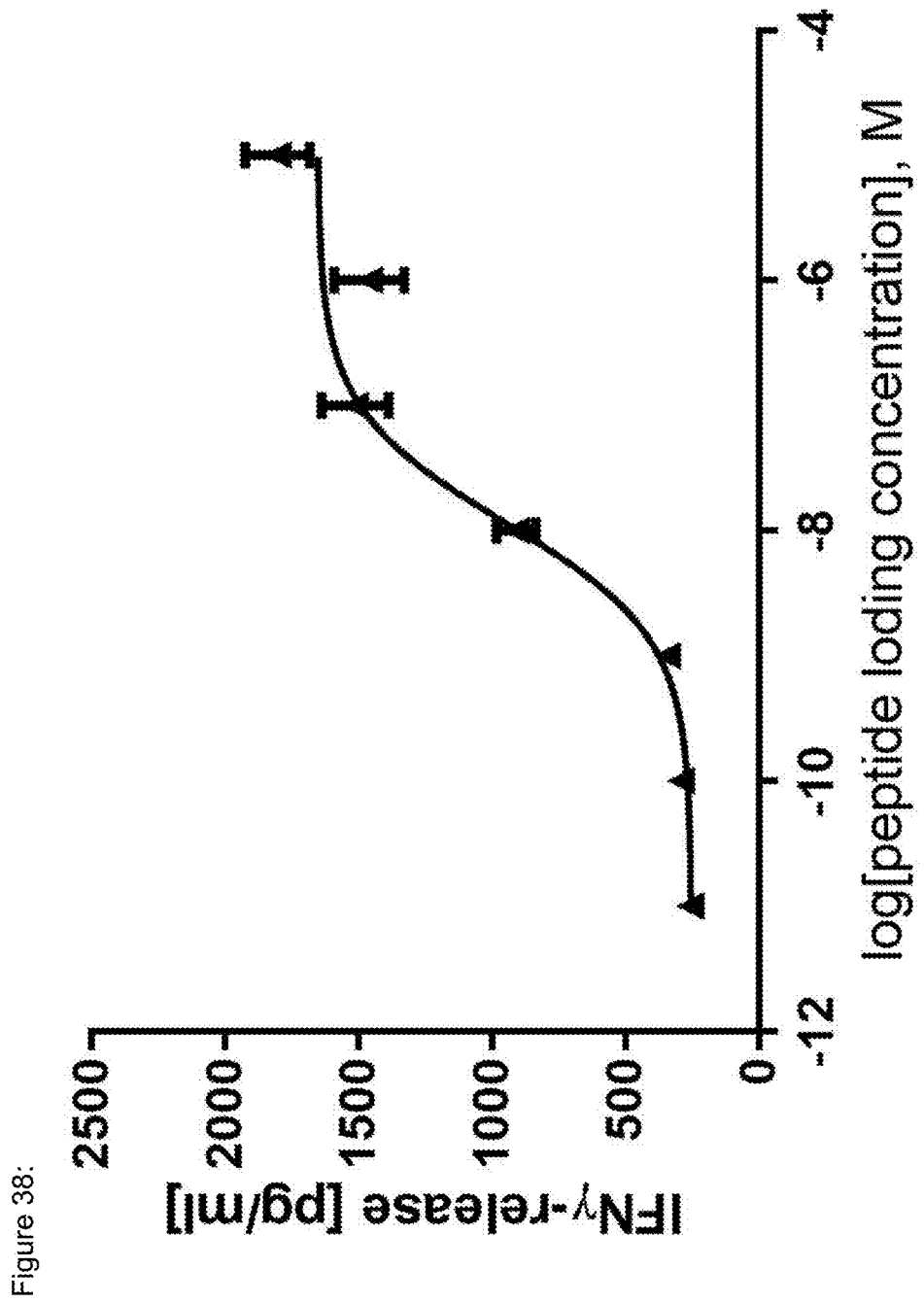

FIG. 38: IFNγ release from CD8+ T-cells electroporated with alpha and beta chain RNA of TCR R35P3A4 (Table 1) after co-incubation with T2 target cells loaded with MAGEA1-003 peptide (SEQ ID NO:133) in various peptide loading concentrations from 10 μM to 10 pM.

Figure 39:
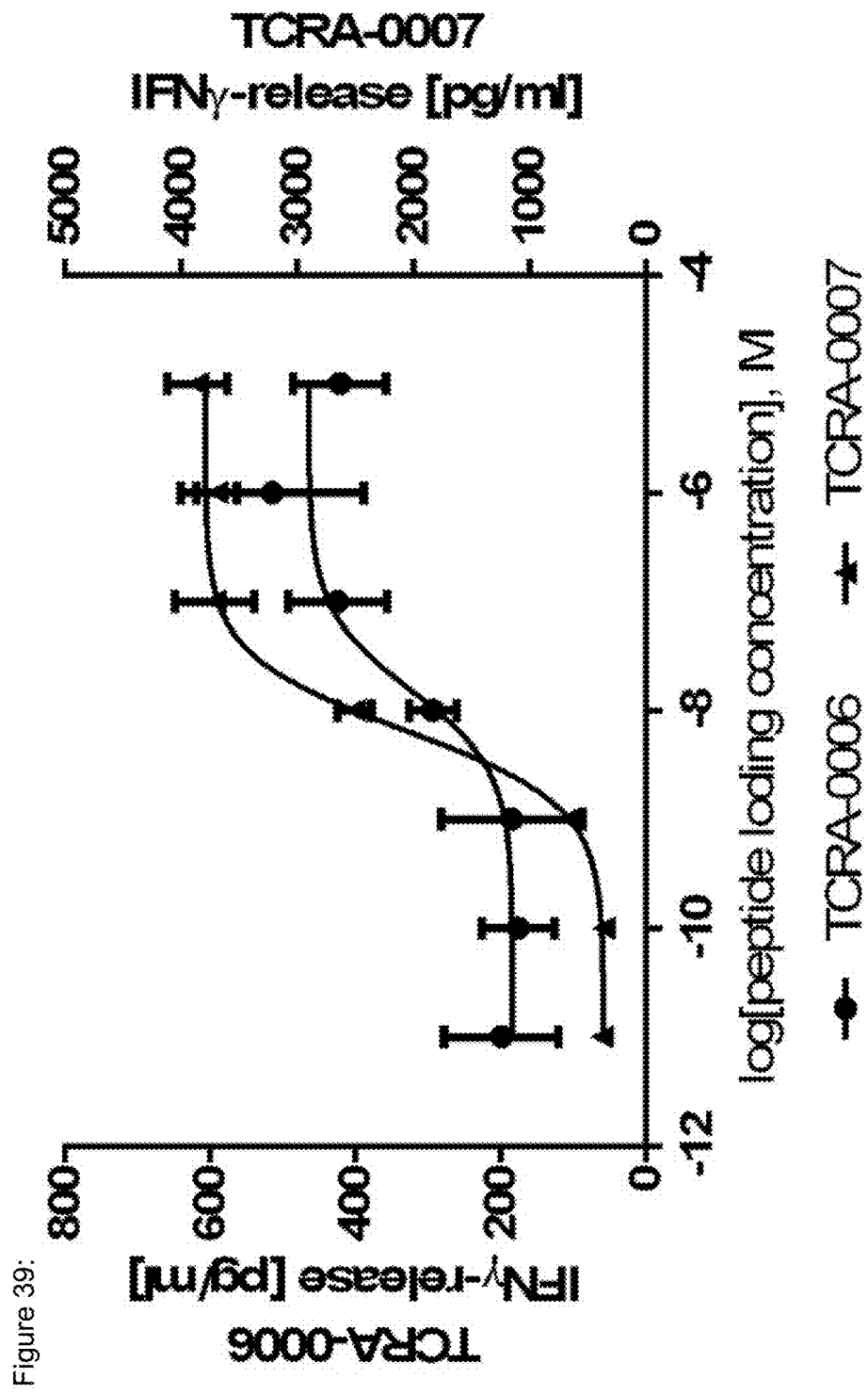

FIG. 39: IFNγ release from CD8+ T-cells electroporated with alpha and beta chain RNA of TCR R37P1C9 (Table 1) after co-incubation with T2 target cells loaded with MAGEA1-003 peptide (SEQ ID NO:133) in various peptide loading concentrations from 10 μM to 10 pM. IFNγ release data were obtained with CD8+ T-cells derived from two different healthy donors.

Figure 40:
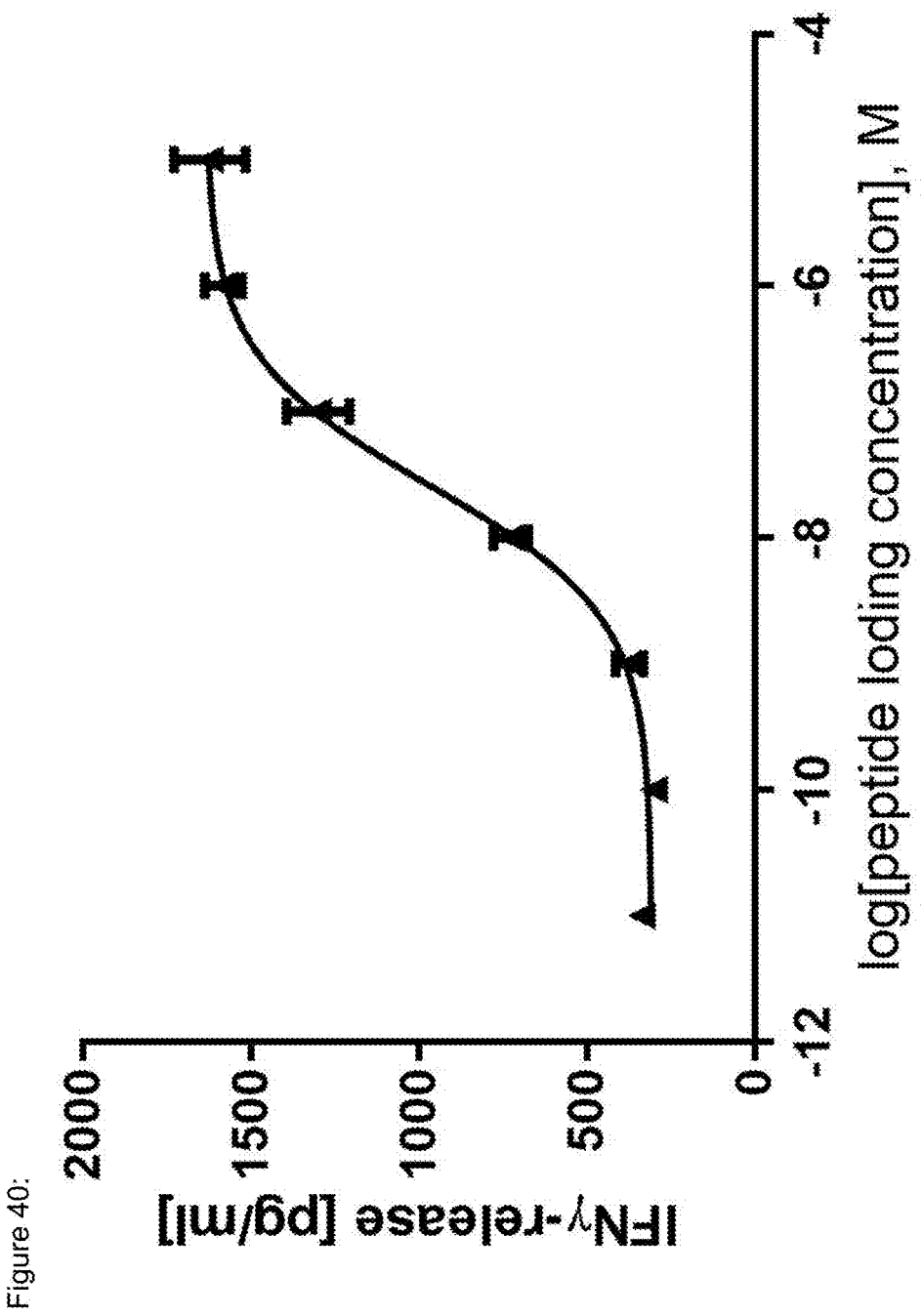

FIG. 40: IFNγ release from CD8+ T-cells electroporated with alpha and beta chain RNA of TCR R37P1H1 (Table 1) after co-incubation with T2 target cells loaded with MAGEA1-003 peptide (SEQ ID NO:133) in various peptide loading concentrations from 10 μM to 10 pM.

Figure 41:
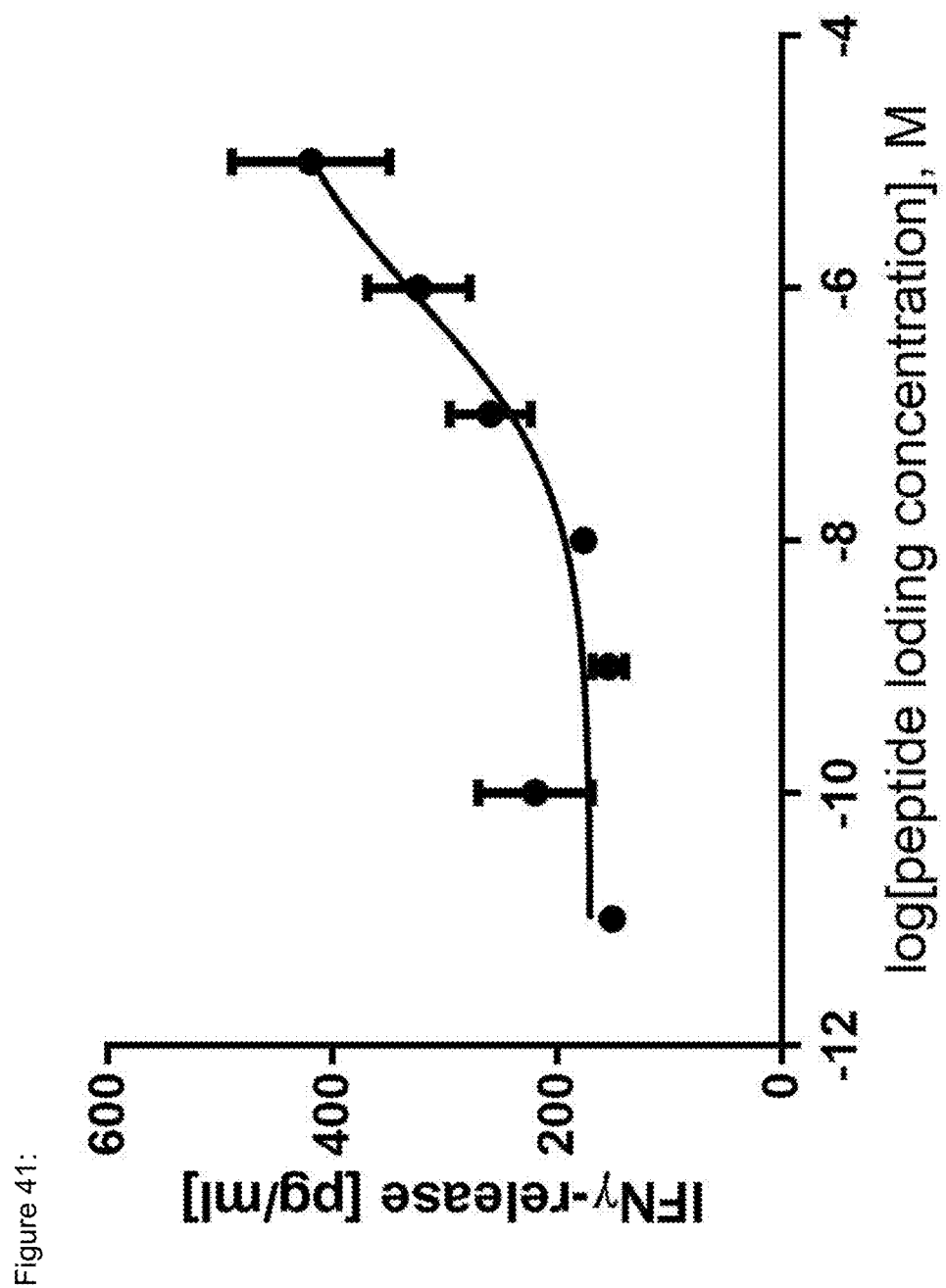

FIG. 41: IFNγ release from CD8+ T-cells electroporated with alpha and beta chain RNA of TCR R42P3A9 (Table 1) after co-incubation with T2 target cells loaded with MAGEA1-003 peptide (SEQ ID NO:133) in various peptide loading concentrations from 10 μM to 10 pM.

Figure 42:
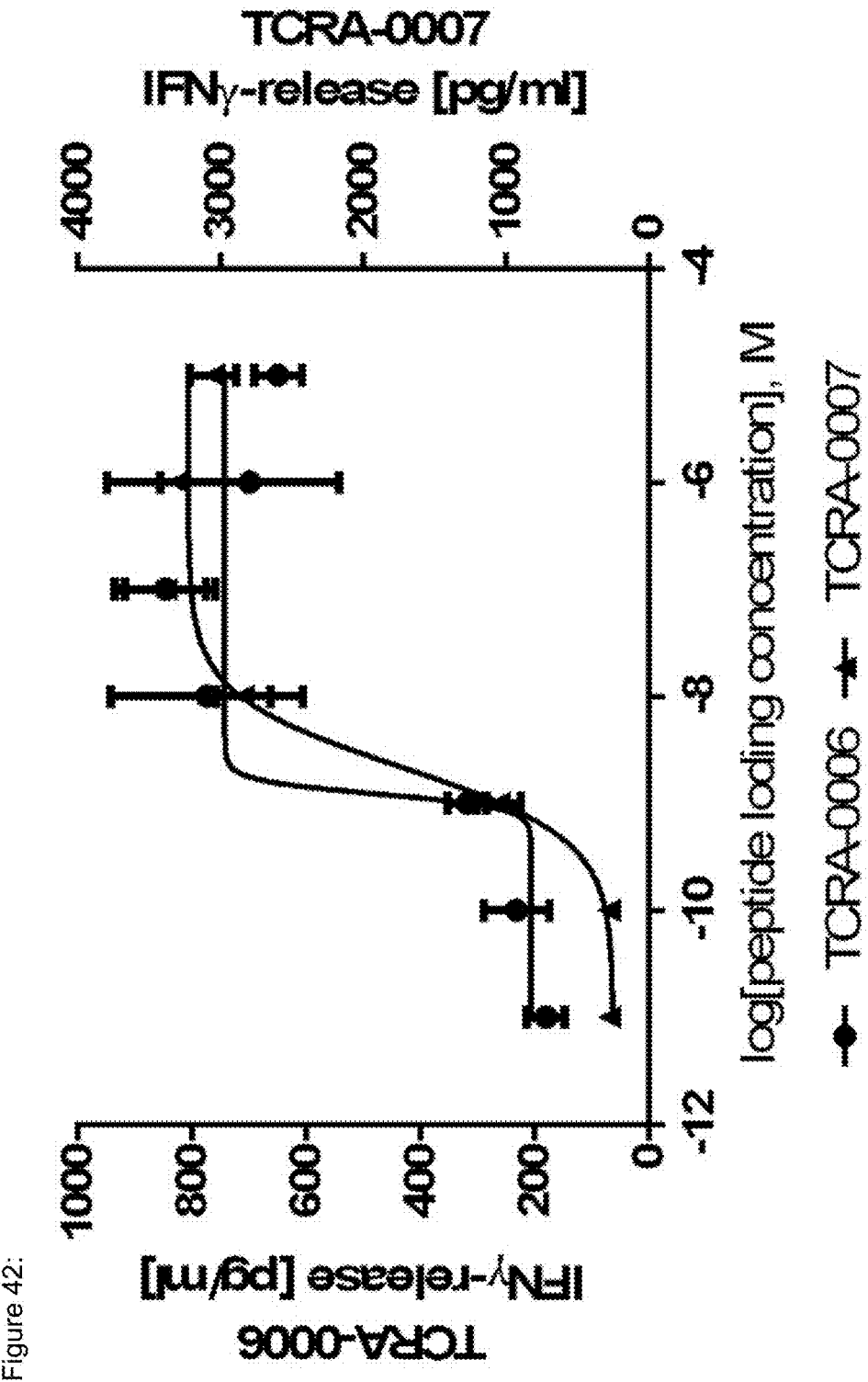

FIG. 42: IFNγ release from CD8+ T-cells electroporated with alpha and beta chain RNA of TCR R43P3F2 (Table 1) after co-incubation with T2 target cells loaded with MAGEA1-003 peptide (SEQ ID NO:133) in various peptide loading concentrations from 10 μM to 10 pM. IFNγ release data were obtained with CD8+ T-cells derived from two different healthy donors.

Figure 43:
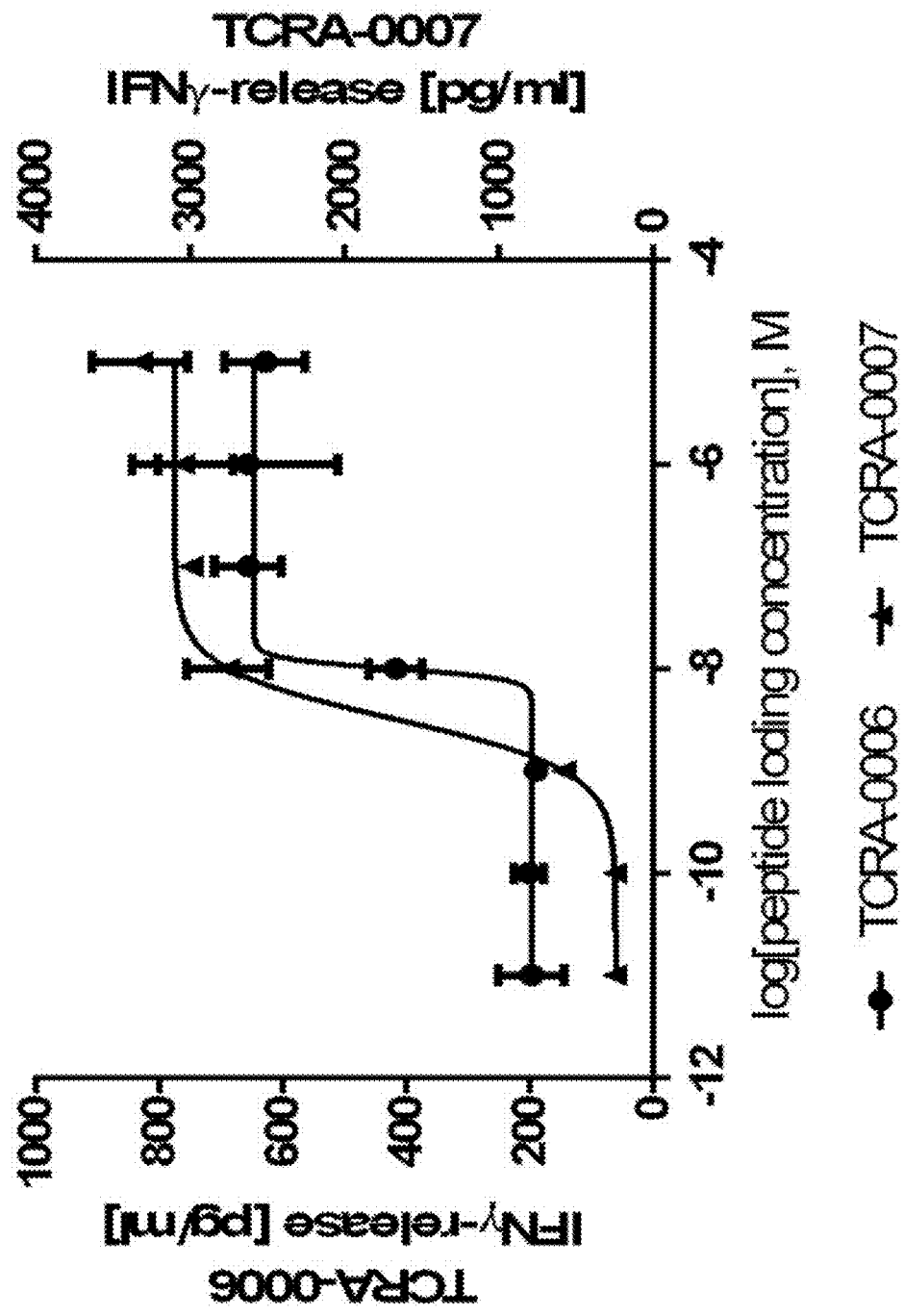

FIG. 43: IFNγ release from CD8+ T-cells electroporated with alpha and beta chain RNA of TCR R43P3G5 (Table 1) after co-incubation with T2 target cells loaded with MAGEA1-003 peptide (SEQ ID NO:133) in various peptide loading concentrations from 10 μM to 10 pM. IFNγ release data were obtained with CD8+ T-cells derived from two different healthy donors.

Figure 44:
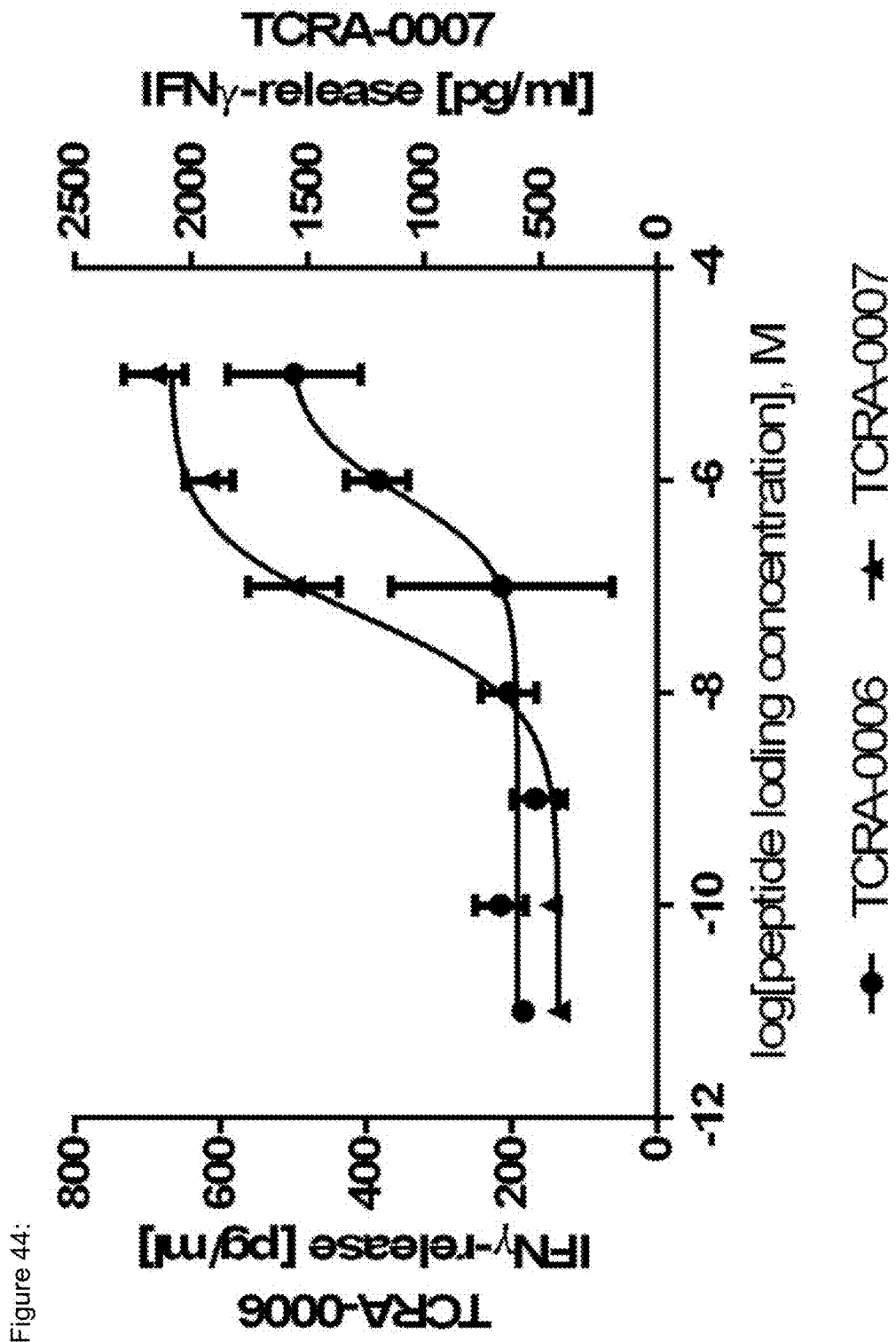

FIG. 44: IFNγ release from CD8+ T-cells electroporated with alpha and beta chain RNA of TCR R59P2E7 (Table 1) after co-incubation with T2 target cells loaded with MAGEA1-003 peptide (SEQ ID NO:133) in various peptide loading concentrations from 10 μM to 10 pM. IFNγ release data were obtained with CD8+ T-cells derived from two different healthy donors.

DETAILED DESCRIPTION OF A PREFERRED EMBODIMENT

Antigen Recognizing Constructs

The object of the invention is solved in a first aspect by an antigen recognizing construct comprising at least one complementary determining region (CDR) 3 having at least 50%, 60%, 70%, 80%, 90%, 95%, 98%, 99%, or preferably 100% sequence identity to an amino acid sequence selected from SEQ ID NOs. 3, 9, 15, 21, 27, 33, 39, 45, 51, 57, 63, 69, 75, 81, 87, 93, 99, 105, 111 and 117.

In some embodiments the antigen recognizing construct of the invention specifically binds to a TAA-peptide-HLA molecule complex, wherein the TAA peptide comprises, or alternatively consists of, a variant of the TAA which is at least 66%, preferably at least 77%, and more preferably at least 88% homologous (preferably at least 77% or at least 88% identical) to the amino acid sequence of the TAA of the invention, wherein said variant binds to an HLA class I or class II molecule and/or induces T-cells cross-reacting with said peptide, or a pharmaceutically acceptable salt thereof, wherein said peptide is not the underlying full-length polypeptide.

As used herein, the terms "identical" or percent "identity", when used anywhere herein in the context of two or more nucleic acid or protein/polypeptide sequences, refer to two or more sequences or subsequences that are the same or have (or have at least) a specified percentage of amino acid residues or nucleotides that are the same (i.e., at, or at least, about 60% identity, preferably at, or at least, 65%, 70%, 75%, 80%, 85%, 90%, 91%, 92%, 93% or 94%, identity, and more preferably at, or at least, about 95%, 96%, 97%, 98%, 99%, or higher identity over a specified region—preferably over their full length sequences—, when compared and aligned for maximum correspondence over the comparison window or designated region) as measured using a sequence comparison algorithms, or by manual alignment and visual inspection (see, e.g., NCBI web site). In a particular embodiment, for example when comparing the protein or nucleic acid sequence of an antigen recognizing construct of the invention to another protein/gene, the percentage identity can be determined by the Blast searches supported at the Human Olfactory Data Explorer (e.g., https://genome.weizmann.ac.il/cgi-bin/horde/blastHorde.pl); in particular for amino acid identity, those using BLASTP 2.2.28+ with the following parameters: Matrix: BLOSUM62; Gap Penalties: Existence: 11, Extension: 1; Neighboring words threshold: 11; Window for multiple hits: 40.

In the context of the present invention it shall be understood that any embodiments referred to as "comprising" certain features of the invention, shall be understood to include in some more preferred embodiments the more restricted description of "consisting of" or "consisting essentially of" the very same features of the present invention.

In another additional or alternative embodiment, the antigen recognizing construct may further comprise a CDR1 and/or a CDR2 domain sequence. Within the variable domain, CDR1 and CDR2 are found in the variable (V) region of a polypeptide chain, and CDR3 includes some of V, all of diversity (D) and joining (J) regions. CDR3 is the most variable and is the main CDR responsible for specifically and selectively recognizing an antigen. CDR1 and CDR2 sequences may be selected from a CDR sequence of a human variable chain allele.

Native alpha-beta heterodimeric TCRs have an alpha chain and a beta chain. Each chain comprises variable, joining and constant regions, and the beta chain also usually contains a short diversity region between the variable and joining regions, but this diversity region is often considered as part of the joining region. Each variable region comprises three CDRs (Complementarity Determining Regions) embedded in a framework sequence, one being the hypervariable region named CDR3. There are several types of alpha chain variable (Vα) regions and several types of beta chain variable (Vβ) regions distinguished by their framework, CDR1 and CDR2 sequences, and by a partly defined CDR3 sequence. The Vα types are referred to in IMGT nomenclature by a unique TRAV number, Vβ types are referred to by a unique TRBV number. For more information on immunoglobulin antibody and TCR genes see the international ImMunoGeneTics information System®, Lefranc M-P et al (Nucleic Acids Res. 2015 January; 43(Database issue):D413-22; and http://www.imgt.org/).

Therefore, in one additional or alternative embodiment the antigen recognizing construct of the invention comprises CDR1, CDR2 and CDR3 sequences in a combination as provided in table 1 herein below, which display the respective variable chain allele together with the CDR3 sequence. Therefore, preferred are antigen recognizing constructs of the invention which comprise at least one, preferably, all three CDR sequences CDR1, CDR2 and CDR3. Preferably, an antigen recognizing construct of the invention comprises the respective CDR1 to CDR3 of one individual herein disclosed TCR variable region of the invention (see table 1 herein below and the example section).

The term "specificity" or "antigen specificity" or "specific for" a given antigen, as used herein means that the antigen recognizing construct can specifically bind to said antigen, preferably a TAA antigen, more preferably with high avidity, when said antigen is presented by HLA, preferably by HLA A2. For example, a TCR, as antigen recognizing construct, may be considered to have "antigenic specificity" for the TAA, if T cells expressing the TCR secrete at least 200 pg/ml or more (e.g., 250 pg/ml or more, 300 pg/ml or more, 400 pg/ml or more, 500 pg/ml or more, 600 pg/ml or more, 700 pg/ml or more, 1000 pg ml or more, 2,000 pg/ml or more, 2,500 pg/ml or more, 5,000 pg/ml or more) of interferon β (IFN-γ) upon co-culture with HLA A2-positive target cells pulsed with a low concentration of a TAA antigen, such as the TAA epitopes and antigens provided herein below (e.g., about 10-11 mol/l, 10-10 mol/l, 10-9 mol/l, 10-8 mol/l, 10-7 mol/l, 10-6 mol/l, 10-5 mol/l). Alternatively, or additionally, a TCR may be considered to have "antigenic specificity" for the TAA, if T cells expressing the TCR secrete at least twice as much IFN-γ as the untransduced background level of IFN-γ upon co-culture with target cells pulsed with a low concentration of the TAA antigens. Such a "specificity" as described above can—for example—be analyzed with an ELISA.

In one alternative or additional embodiment of the invention, the antigen recognizing construct selectively binds to a TAA derived antigenic peptide; preferably wherein the TAA antigenic peptide is a protein epitope or peptide having an amino acid sequence shown in SEQ ID NO: 133, or a variant thereof, wherein the variant is an amino acid deletion, addition, insertion or substitution of not more than three, preferably two and most preferably not more than one amino acid position. In some embodiments, the antigen recognizing construct of the invention selectively binds any of the modified MAGEA1-003 peptides set forth in SEQ ID NO: 132 to 142 and 154 to 162. In some preferred embodiments, the antigen recognizing construct of the invention does not selectively bind any of the modified MAGEA1-003 peptides set forth in SEQ ID NO: 143 to 152.

The term "selectivity" or "selective recognizing/binding" is understood to refer to the property of an antigen recognizing construct, such as a TCR or antibody, to selectively recognize or bind to preferably only one specific epitope and preferably shows no or substantially no cross-reactivity to another epitope. Preferably "selectivity" or "selective recognizing/binding" means that the antigen recognizing construct (e.g. a TCR) selectively recognizes or binds to preferably only one specific epitope and preferably shows no or substantially no cross-reactivity to another epitope, wherein said epitope is unique for one protein, such that the antigen recognizing construct shows no or substantially no cross-reactivity to another epitope and another protein.

The antigen recognizing construct according to the invention is preferably selected from an antibody, or derivative or fragment thereof, or a T cell receptor (TCR), or derivative or fragment thereof. A derivative or fragment of an antibody or TCR of the invention shall preferably retain the antigen binding/recognizing ability of the parent molecule, in particular its specificity and/or selectivity as explained above. Such binding functionality may be retained by the presence of a CDR3 region as defined herein.

In an embodiment of the invention, the inventive TCRs are able to recognize TAA antigens in a major histocompatibility complex (MHC) class I-dependent manner. "MHC class I-dependent manner," as used herein, means that the TCR elicits an immune response upon binding to TAA antigens within the context of an MHC class I molecule. The MHC class I molecule can be any MHC class I molecule known in the art, e.g., HLA-A molecules. In a preferred embodiment of the invention, the MHC class I molecule is an HLA-A2 molecule.

The invention provides both single chain antigen recognizing construct and double chain recognizing constructs.

In an embodiment, the TCR alpha variable domain has at least one mutation relative to a TCR alpha domain shown in Table 1; and/or the TCR beta variable domain has at least one mutation relative to a TCR alpha domain shown in Table 1. In an embodiment, a TCR comprising at least one mutation in the TCR alpha variable domain and/or TCR beta variable domain has a binding affinity for, and/or a binding half-life for, a TAA peptide-HLA molecule complex, which is at least double that of a TCR comprising the unmutated TCR alpha domain and/or unmutated TCR beta variable domain.

The TCR alpha chains of the present description may further comprise a TCR alpha transmembrane domain and/or a TCR alpha intracellular domain. The TCR beta chains of the present description may further comprise a TCR beta transmembrane domain and/or a TCR beta intracellular domain.

The invention in particular provides a TCR as antigen recognizing construct, or fragment or derivative thereof. The TCR preferably is of human, which is understood as being generated from a human TCR locus and therefore comprising human TCR sequences. Furthermore, the TCR of the invention may be characterized in that it is of human origin and specifically recognizes a TAA antigen of the invention.

Another embodiment of the invention additionally or alternatively provides the antigen recognizing construct described above, which induces an immune response, preferably wherein the immune response is characterized by an increase in interferon (IFN) γ levels.

TCRs of the invention may be provided as single chain α or β, or γ and δ, molecules, or alternatively as double chain constructs composed of both the α and β chain, or γ and δ chain.

The antigen recognizing construct of the invention may comprise a TCR α or γ chain; and/or a TCR β or δ chain; wherein the TCR α or γ chain comprises a CDR3 having at least 50%, 60%, 70%, 80%, 90%, 95%, 98%, 99%, or 100% sequence identity to an amino acid sequence selected from SEQ ID Nos. 3, 15, 27, 39, 51, 63, 75, 87, 99 and 111, and/or wherein the TCR β or δ chain comprises a CDR3 having at least 50%, 60%, 70%, 80%, 90%, 95%, 98%, 99%, or 100% sequence identity to an amino acid sequence selected from SEQ ID Nos. 9, 21, 33, 45, 57, 69, 81, 93, 105 and 117.

Most preferably, in some additional embodiments, wherein the disclosure refers to antigen recognizing constructs comprising any one, two or all of the CDR1 to CDR3 regions of the herein disclosed TCR chains (see Table 1), such antigen recognizing constructs may be preferred, which comprise the respective CDR sequence of the invention with not more than three, two, and preferably only one, modified amino acid residues. A modified amino acid residue may be selected from an amino acid insertion, deletion or substitution. Most preferred is that the three, two, preferably only one modified amino acid residue is the first or last amino acid residue of the respective CDR sequence. If the modification is a substitution then it is preferable in some embodiments that the substitution is a conservative amino acid substitution.

If the antigen recognizing construct of the invention is composed of at least two amino acid chains, such as a double chain TCR, or antigen binding fragment thereof, the antigen recognizing construct may comprise in a first polypeptide chain the amino acid sequence according to SEQ ID NO: 3, and in a second polypeptide chain the amino acid sequence according to SEQ ID NO: 9; or in a first polypeptide chain the amino acid sequence according to SEQ ID NO: 15, and in a second polypeptide chain the amino acid sequence according to SEQ ID NO: 21; or in a first polypeptide chain the amino acid sequence according to SEQ ID NO: 27, and in a second polypeptide chain the amino acid sequence according to SEQ ID NO: 33; or in a first polypeptide chain the amino acid sequence according to SEQ ID NO: 39, and in a second polypeptide chain the amino acid sequence according to SEQ ID NO: 45; or in a first polypeptide chain the amino acid sequence according to SEQ ID NO: 51, and in a second polypeptide chain the amino acid sequence according to SEQ ID NO: 57; or in a first polypeptide chain the amino acid sequence according to SEQ ID NO: 63, and in a second polypeptide chain the amino acid sequence according to SEQ ID NO: 69; or in a first polypeptide chain the amino acid sequence according to SEQ ID NO: 75, and in a second polypeptide chain the amino acid sequence according to SEQ ID NO: 81; or in a first polypeptide chain the amino acid sequence according to SEQ ID NO: 87, and in a second polypeptide chain the amino acid sequence according to SEQ ID NO: 93; or in a first polypeptide chain the amino acid sequence according to SEQ ID NO: 99, and in a second polypeptide chain the amino acid sequence according to SEQ ID NO: 105; or in a first polypeptide chain the amino acid sequence according to SEQ ID NO: 111, and in a second polypeptide chain the amino acid sequence according to SEQ ID NO: 117. Any one of the aforementioned double chain TCR, or antigen binding fragments thereof, are preferred TCR of the present invention. In some embodiments, the CDR3 of the double chain TCR of the invention may be mutated. Mutations of the CDR3 sequences of SEQ ID NOs. 3, 9, 15, 21, 27, 33, 39, 45, 51, 57, 63, 69, 75, 81, 87, 93, 99, 105, 111 and 117, as provided above preferably include a substitution, deletion, addition, or insertion of not more than three, preferably not more than two, and most preferably not more than one amino acid residue. In some embodiments, the first polypeptide chain may be a TCR α or γ chain, and the second polypeptide chain may be a TCR β or δ chain. Preferred is the combination of an αβ or γδ TCR.

The TCR, or the antigen binding fragment thereof, is in some embodiments composed of a TCR α and a TCR β chain, or γ and δ chain. Such a double chain TCR comprises within each chain variable regions, and the variable regions each comprise one CDR1, one CDR2 and one CDR3 sequence. The TCRs comprises the CDR1 to CDR3 sequences as comprised in the variable chain amino acid sequence of SEQ ID NO: 4 and SEQ ID NO: 10 (R26P1A9), or SEQ ID NO: 16 and SEQ ID NO: 22 (R26P2A6); or SEQ ID NO: 28 and SEQ ID NO: 34 (R26P3H1) or SEQ ID NO: 40 and SEQ ID NO: 46 (R35P3A4), or SEQ ID NO: 52 and SEQ ID NO: 58 (R37P1C9), or SEQ ID NO: 64 and SEQ ID NO: 70 (R37P1H1), or SEQ ID NO: 76 and SEQ ID NO: 82 (R42P3A9), or SEQ ID NO: 88 and SEQ ID NO: 94 (R43P3F2), or SEQ ID NO: 100 and SEQ ID NO: 106 (R43P3G5), or SEQ ID NO: 112 and SEQ ID NO: 118 (R59P2E7).

Some embodiments of the invention pertain to a TCR, or a fragment thereof, composed of a TCR α and a TCR β chain, wherein said TCR comprises the variable region sequences having at least 50%, 60%, 70%, 80%, 90%, 95%, 98%, 99%, or preferably 100% sequence identity to the amino acid sequence selected from the α and β chain according to SEQ ID NO: 4 and 10 respectively, or 16 and 22 respectively; or 28 and 34 respectively or 40 and 46 respectively, or 52 and 58 respectively, or 64 and 70 respectively, or 76 and 82 respectively, or 88 and 94 respectively, or 100 and 106 respectively or 112 and 118 respectively.

The inventive TCRs may further comprise a constant region derived from any suitable species, such as any mammal, e.g., human, rat, monkey, rabbit, donkey, or mouse. In an embodiment of the invention, the inventive TCRs further comprise a human constant region. In some preferred embodiments, the constant region of the TCR of the invention may be slightly modified, for example, by the introduction of heterologous sequences, preferably mouse sequences, which may increase TCR expression and stability.

Some embodiments of the invention pertain to a TCR, or a fragment thereof, composed of a TCR α and a TCR β chain, wherein said TCR comprises the constant region having at least 50%, 60%, 70%, 80%, 90%, 95%, 98%, 99%, or preferably 100% sequence identity to an amino acid sequence selected from of the α and β chain according to SEQ ID NO: 5 and 11 respectively, or 17 and 23 respectively; or 29 and 35 respectively; or 41 and 47 respectively; or 53 and 59 respectively; or 65 and 71 respectively; or 77 and 83 respectively; or 89 and 95 respectively; or 101 and 107 respectively; or 113 and 119 respectively.

The TCR α or γ chain of the invention may further comprise a CDR1 having at least 50%, 60%, 70%, 80%, 90%, 95%, 98%, 99%, or 100% sequence identity to an amino acid sequence selected from SEQ ID Nos. 1, 13, 25, 37, 49, 61, 73, 85, 97, and 109; and/or a CDR2 having at least 50%, 60%, 70%, 80%, 90%, 95%, 98%, 99%, or 100% sequence identity to an amino acid sequence selected from SEQ ID Nos. 2, 14, 26, 38, 50, 62, 74, 86, 98, and 110.

According to the invention the TCR β or δ chain may further comprise a CDR1 having at least 50%, 60%, 70%, 80%, 90%, 95%, 98%, 99%, or 100% sequence identity to an amino acid sequence selected from SEQ ID Nos. 7, 19, 31, 43, 55, 67, 79, 91, 103 and 115; and/or a CDR2 having at least 50%, 60%, 70%, 80%, 90%, 95%, 98%, 99%, or 100% sequence identity to an amino acid sequence selected from SEQ ID Nos. 8, 20, 32, 44, 56, 68, 80, 92, 104 and 116.

The antigen recognizing construct may in a further embodiment comprise a binding fragment of a TCR, and wherein said binding fragment comprises CDR1 to CDR3, optionally selected from the CDR1 to CDR3 sequences having the amino acid sequences of SEQ ID Nos. 1, 2, 3, or 7, 8, 9 or 13, 14, 15, or 19, 20, 21, or 25, 26, 27 or 31, 32, 33 or 37, 38, 39 or 43, 44, 45 or 49, 50, 51 or 55, 56, 57 or 61, 62, 63 or 67, 68, 69 or 73, 74, 75 or 79, 80, 81 or 85, 86, 87 or 91, 92, 93 or 97, 98, 99 or 103, 104, 105 or 109, 110, 111 or 115, 116, 117.

In further embodiments of the invention the antigen recognizing construct as described herein elsewhere is a TCR, or a fragment thereof, composed of at least one TCR α and one TCR β chain sequence, wherein said TCR α chain sequence comprises the CDR1 to CDR3 sequences having the amino acid sequences of SEQ ID NO: 1 to 3, and said TCR β chain sequence comprises the CDR1 to CDR3 sequences having the amino acid sequences of SEQ ID NO: 7 to 9; or wherein said TCR α chain sequence comprises the CDR1 to CDR3 sequences having the amino acid sequences of SEQ ID NO: 13 to 15, and said TCR β chain sequence comprises the CDR1 to CDR3 sequences having the amino acid sequences of SEQ ID NO: 19 to 21; or wherein said TCR α chain sequence comprises the CDR1 to CDR3 sequences having the amino acid sequences of SEQ ID NO: 25 to 27, and said TCR β chain sequence comprises the CDR1 to CDR3 sequences having the amino acid sequences of SEQ ID NO: 31 to 33; or wherein said TCR α chain sequence comprises the CDR1 to CDR3 sequences having the amino acid sequences of SEQ ID NO: 37 to 39, and said TCR β chain sequence comprises the CDR1 to CDR3 sequences having the amino acid sequences of SEQ ID NO: 43 to 45; or wherein said TCR α chain sequence comprises the CDR1 to CDR3 sequences having the amino acid sequences of SEQ ID NO: 49 to 51, and said TCR β chain sequence comprises the CDR1 to CDR3 sequences having the amino acid sequences of SEQ ID NO: 55 to 57; or wherein said TCR α chain sequence comprises the CDR1 to CDR3 sequences having the amino acid sequences of SEQ ID NO: 61 to 63, and said TCR β chain sequence comprises the CDR1 to CDR3 sequences having the amino acid sequences of SEQ ID NO: 67 to 69; or wherein said TCR α chain sequence comprises the CDR1 to CDR3 sequences having the amino acid sequences of SEQ ID NO: 73 to 75, and said TCR β chain sequence comprises the CDR1 to CDR3 sequences having the amino acid sequences of SEQ ID NO: 79 to 81; or wherein said TCR α chain sequence comprises the CDR1 to CDR3 sequences having the amino acid sequences of SEQ ID NO: 85 to 87, and said TCR β chain sequence comprises the CDR1 to CDR3 sequences having the amino acid sequences of SEQ ID NO: 91 to 93; or wherein said TCR α chain sequence comprises the CDR1 to CDR3 sequences having the amino acid sequences of SEQ ID NO: 97 to 99, and said TCR β chain sequence comprises the CDR1 to CDR3 sequences having the amino acid sequences of SEQ ID NO: 103 to 105; or wherein said TCR α chain sequence comprises the CDR1 to CDR3 sequences having the amino acid sequences of SEQ ID NO: 109 to 111, and said TCR β chain sequence comprises the CDR1 to CDR3 sequences having the amino acid sequences of SEQ ID NO: 115 to 117.

In further embodiments of the invention the antigen recognizing construct as described herein before is a TCR, or a fragment thereof, comprising at least one TCR α and one TCR β chain sequence, wherein said TCR α chain sequence comprises a variable region sequence having the amino acid sequence of SEQ ID No. 4, and wherein said TCR β chain sequence comprises a variable region sequence having the amino acid sequence of SEQ ID No. 10; or wherein said TCR α chain sequence comprises a variable region sequence having the amino acid sequence of SEQ ID No. 16, and wherein said TCR β chain sequence comprises a variable region sequence having the amino acid sequence of SEQ ID No. 22; or wherein said TCR α chain sequence comprises a variable region sequence having the amino acid sequence of SEQ ID No. 28, and wherein said TCR β chain sequence comprises a variable region sequence having the amino acid sequence of SEQ ID No. 34; or wherein said TCR α chain sequence comprises a variable region sequence having the amino acid sequence of SEQ ID No. 40, and wherein said TCR β chain sequence comprises a variable region sequence having the amino acid sequence of SEQ ID No. 46; or wherein said TCR α chain sequence comprises a variable region sequence having the amino acid sequence of SEQ ID No. 52, and wherein said TCR β chain sequence comprises a variable region sequence having the amino acid sequence of SEQ ID No. 58; or wherein said TCR α chain sequence comprises a variable region sequence having the amino acid sequence of SEQ ID No. 64, and wherein said TCR β chain sequence comprises a variable region sequence having the amino acid sequence of SEQ ID No. 70; or wherein said TCR α chain sequence comprises a variable region sequence having the amino acid sequence of SEQ ID No. 76, and wherein said TCR β chain sequence comprises a variable region sequence having the amino acid sequence of SEQ ID No. 82; or wherein said TCR α chain sequence comprises a variable region sequence having the amino acid sequence of SEQ ID No. 88, and wherein said TCR β chain sequence comprises a variable region sequence having the amino acid sequence of SEQ ID No. 94; or wherein said TCR α chain sequence comprises a variable region sequence having the amino acid sequence of SEQ ID No. 100, and wherein said TCR β chain sequence comprises a variable region sequence having the amino acid sequence of SEQ ID No. 106; or wherein said TCR α chain sequence comprises a variable region sequence having the amino acid sequence of SEQ ID No. 112, and wherein said TCR β chain sequence comprises a variable region sequence having the amino acid sequence of SEQ ID No. 118.

In further embodiments of the invention the antigen recognizing construct as described herein before is a TCR, or a fragment thereof, further comprising a TCR constant region having at least 50%, 60%, 70%, 80%, 90%, 95%, 98%, 99%, or 100% sequence identity to an amino acid sequence selected from SEQ ID Nos. 5, 11, 17, 23, 29,35, 41, 47, 53, 59, 65, 71, 77, 83, 89, 95, 101, 107, 113 and 119, preferably wherein the TCR is composed of at least one TCR α and one TCR β chain sequence, wherein the TCR α chain sequence comprises a constant region having at least 50%, 60%, 70%, 80%, 90%, 95%, 98%, 99%, or 100% sequence identity to an amino acid sequence selected from SEQ ID Nos. 5, 17, 29, 41, 53, 65, 77, 89, 101 and 113.

Also disclosed are antigen recognizing constructs as described herein before comprising a first TCR chain having at least 50%, 60%, 70%, 80%, 90%, 95%, 98%, 99%, or 100% sequence identity to the amino acid sequence of SEQ ID No. 6, and a second TCR chain having at least 50%, 60%, 70%, 80%, 90%, 95%, 98%, 99%, or 100% sequence identity to the amino acid sequence of SEQ ID No. 12. The invention also provides TCRs comprising a first TCR chain having at least 50%, 60%, 70%, 80%, 90%, 95%, 98%, 99%, or 100% sequence identity to the amino acid sequence of SEQ ID No. 18, and a second TCR chain having at least 50%, 60%, 70%, 80%, 90%, 95%, 98%, 99%, or 100% sequence identity to the amino acid sequence of SEQ ID No. 24. In further embodiments the invention provides antigen recognizing constructs which are TCR and comprise a first TCR chain having at least 50%, 60%, 70%, 80%, 90%, 95%, 98%, 99%, or 100% sequence identity to the amino acid sequence of SEQ ID No. 30, and a second TCR chain having at least 50%, 60%, 70%, 80%, 90%, 95%, 98%, 99%, or 100% sequence identity to the amino acid sequence of SEQ ID No. 36. In further embodiments the invention provides antigen recognizing constructs which are TCR and comprise a first TCR chain having at least 50%, 60%, 70%, 80%, 90%, 95%, 98%, 99%, or 100% sequence identity to the amino acid sequence of SEQ ID No. 42, and a second TCR chain having at least 50%, 60%, 70%, 80%, 90%, 95%, 98%, 99%, or 100% sequence identity to the amino acid sequence of SEQ ID No. 48. In further embodiments the invention provides antigen recognizing constructs which are TCR and comprise a first TCR chain having at least 50%, 60%, 70%, 80%, 90%, 95%, 98%, 99%, or 100% sequence identity to the amino acid sequence of SEQ ID No. 54, and a second TCR chain having at least 50%, 60%, 70%, 80%, 90%, 95%, 98%, 99%, or 100% sequence identity to the amino acid sequence of SEQ ID No. 60. In further embodiments the invention provides antigen recognizing constructs which are TCR and comprise a first TCR chain having at least 50%, 60%, 70%, 80%, 90%, 95%, 98%, 99%, or 100% sequence identity to the amino acid sequence of SEQ ID No. 66, and a second TCR chain having at least 50%, 60%, 70%, 80%, 90%, 95%, 98%, 99%, or 100% sequence identity to the amino acid sequence of SEQ ID No. 72. In further embodiments the invention provides antigen recognizing constructs which are TCR and comprise a first TCR chain having at least 50%, 60%, 70%, 80%, 90%, 95%, 98%, 99%, or 100% sequence identity to the amino acid sequence of SEQ ID No. 78, and a second TCR chain having at least 50%, 60%, 70%, 80%, 90%, 95%, 98%, 99%, or 100% sequence identity to the amino acid sequence of SEQ ID No. 84. In further embodiments the invention provides antigen recognizing constructs which are TCR and comprise a first TCR chain having at least 50%, 60%, 70%, 80%, 90%, 95%, 98%, 99%, or 100% sequence identity to the amino acid sequence of SEQ ID No. 90, and a second TCR chain having at least 50%, 60%, 70%, 80%, 90%, 95%, 98%, 99%, or 100% sequence identity to the amino acid sequence of SEQ ID No. 96. In further embodiments the invention provides antigen recognizing constructs which are TCR and comprise a first TCR chain having at least 50%, 60%, 70%, 80%, 90%, 95%, 98%, 99%, or 100% sequence identity to the amino acid sequence of SEQ ID No. 102, and a second TCR chain having at least 50%, 60%, 70%, 80%, 90%, 95%, 98%, 99%, or 100% sequence identity to the amino acid sequence of SEQ ID No. 108. In further embodiments the invention provides antigen recognizing constructs which are TCR and comprise a first TCR chain having at least 50%, 60%, 70%, 80%, 90%, 95%, 98%, 99%, or 100% sequence identity to the amino acid sequence of SEQ ID No. 114, and a second TCR chain having at least 50%, 60%, 70%, 80%, 90%, 95%, 98%, 99%, or 100% sequence identity to the amino acid sequence of SEQ ID No. 120.

As used herein, the term "murine" or "human," when referring to an antigen recognizing construct, or a TCR, or any component of a TCR described herein (e.g., complementarity determining region (CDR), variable region, constant region, α chain, and/or β chain), means a TCR (or component thereof), which is derived from a mouse or a human unrearranged TCR locus, respectively.

In an embodiment of the invention, chimeric TCR are provided, wherein the TCR chains comprise sequences from multiple species. Preferably, a TCR of the invention may comprise an a chain comprising a human variable region of an α chain and, for example, a murine constant region of a murine TCR α chain.

In one embodiment, the TCR of the invention is a human TCR comprising human variable regions according to the above embodiments and human constant regions.

In some embodiments the antigen recognizing construct is murinized or humanized. These terms are used when amino acid sequences from a foreign species are introduced into a construct of the invention.

The TCR of the invention may be provided as a single chain TCR (scTCR). A scTCR can comprise a polypeptide of a variable region of a first TCR chain (e.g., an alpha chain) and a polypeptide of an entire (full-length) second TCR chain (e.g., a beta chain), or vice versa. Furthermore, the scTCR can optionally comprise one or more linkers which join the two or more polypeptides together. The linker can be, for instance, a peptide, which joins together two single chains, as described herein. Also provided is such a scTCR of the invention, which is fused to a human cytokine, such as IL-2, IL-7 or IL-15.

The antigen recognizing construct according to the invention can also be provided in the form of a multimeric complex, comprising at least two scTCR molecules, wherein said scTCR molecules are each fused to at least one biotin moiety, or other interconnecting molecule/linker, and wherein said scTCRs are interconnected by biotin-streptavidin interaction to allow the formation of said multimeric complex. Similar approaches known in the art for the generation of multimeric TCR are also possible and included in this disclosure. Also provided are multimeric complexes of a higher order, comprising more than two scTCR of the invention.

For the purposes of the present invention, a TCR is a moiety having at least one TCR alpha or gamma and/or TCR beta or delta variable domain. Generally, they comprise both a TCR alpha variable domain and a TCR beta variable domain, alternatively both a TCR gamma variable domain and a TCR delta variable domain. They may be αβ/γδ heterodimers or may be in single chain format. For use in adoptive therapy, an αβ or γδ heterodimeric TCR may, for example, be transfected as full length chains having both cytoplasmic and transmembrane domains. If desired, an introduced disulfide bond between residues of the respective constant domains may be present.

In a preferred embodiment, the antigen recognizing construct is a human TCR, or fragment or derivative thereof. A human TCR or fragment or derivative thereof is a TCR, which comprises over 50% of the corresponding human TCR sequence. Preferably, only a small part of the TCR sequence is of artificial origin or derived from other species. It is known, however, that chimeric TCRs, e.g. derived from human origin with murine sequences in the constant domains, are advantageous. Particularly preferred are, therefore, TCRs in accordance with the present invention, which contains murine sequences in the extracellular part of their constant domains.

Thus, it is also preferred that the inventive antigen recognizing construct is able to recognize its antigen in a human leucocyte antigen (HLA) dependent manner, preferably in a HLA-A02 dependent manner. The term "HLA dependent manner" in the context of the present invention means that the antigen recognizing construct binds to the antigen only in the event that the antigenic peptide is presented by said HLA.

The antigen recognizing construct in accordance with the invention in one embodiment preferably induces an immune response, preferably wherein the immune response is characterized by the increase in interferon (IFN) γ levels.

Also provided by the invention is a polypeptide comprising a functional portion of any of the TCRs (or functional variants thereof) described herein, for examples, of any one of the TCRs selected from R26P1A9, R26P2A6, R26P3H1, R35P3A4, R37P1C9, R37P1H1, R42P3A9, R43P3F2, R43P3G5 and R59P2E7, as provided in the example section and table 1. The term "polypeptide" as used herein includes oligopeptides and refers to a single chain of amino acids connected by one or more peptide bonds. With respect to the inventive polypeptides, the functional portion can be any portion comprising contiguous amino acids of the TCR (or functional variant thereof), of which it is a part, provided that the functional portion specifically binds to the TAA antigen, preferably as disclosed herein in Table 2, and peptides MAGEA1-003_A1 to A9 (SEQ ID NOs: 134-142) and MAGEA1-003_T1 to T9 (SEQ ID NOs: 154-162). The term "functional portion" when used in reference to a TCR (or functional variant thereof) refers to any part or fragment of the TCR (or functional variant thereof) of the invention, which part or fragment retains the biological activity of the TCR (or functional variant thereof), of which it is a part (the parent TCR or parent functional variant thereof). Functional portions encompass, for example, those parts of a TCR (or functional variant thereof) that retain the ability to specifically bind to the TAA antigen (in an HLA dependent manner), or detect, treat, or prevent cancer, to a similar extent, the same extent, or to a higher extent, as the parent TCR (or functional variant thereof). In reference to the parent TCR (or functional variant thereof), the functional portion can comprise, for instance, about 10%, 25%, 30%, 50%, 68%, 80%, 90%, 95%, or more, of the parent TCR variable sequences (or functional variant thereof).

The functional portion can comprise additional amino acids at the amino or carboxy terminus of the portion, or at both termini, in which additional amino acids are not found in the amino acid sequence of the parent TCR or functional variant thereof. Desirably, the additional amino acids do not interfere with the biological function of the functional portion, e.g., specifically binding to the TAA antigens; and/or having the ability to detect cancer, treat or prevent cancer, etc. More desirably, the additional amino acids enhance the biological activity, as compared to the biological activity of the parent TCR or functional variant thereof.

The polypeptide can comprise a functional portion of either or both of the α and β chains of the TCRs or functional variant thereof of the invention, such as a functional portion comprising one of more of CDR1, CDR2, and (preferably) CDR3 of the variable region(s) of the α chain and/or β chain of a TCR or functional variant thereof of the invention. In an embodiment of the invention, the polypeptide can comprise a functional portion comprising the amino acid sequence of SEQ ID NO: 3, 9, 15, 21, 27, 33, 39, 45, 51, 57, 63, 69, 75, 81, 87, 93, 99, 105, 111 and 117 (CDR3 of the variable regions of the TCR of the invention), or a combination thereof. In an embodiment of the invention, the inventive polypeptide can comprise, for instance, the variable region of the inventive TCR or functional variant thereof comprising a combination of the CDR regions set forth above. In this regard, the polypeptide can comprise the amino acid sequence of any of SEQ ID NO: 4, 10, 16, 22, 28, 34, 40, 46, 52, 58, 64, 70, 76, 82, 88, 94, 100, 106, 112 and 118 (the variable regions of an α or β chain of the TCR of the invention).

In some instances, the construct of the invention may comprise one or two polypeptide chains comprising sequences according to any of the SEQ ID NO: 1 to 120 (CDR sequences, constant and variable regions and full-length sequences), or functional fragments thereof, and further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide may include any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. In some embodiments of the invention, the TCRs (and functional portions and functional variants thereof), polypeptides, and proteins of the invention may be expressed as a single protein comprising a linker peptide linking the a chain and the β chain, and linking the γ chain and the δ chain. In this regard, the TCRs (and functional variants and functional portions thereof), polypeptides, and proteins of the invention comprising the amino acid sequences of the variable regions of the TCR of the invention and may further comprise a linker peptide. The linker peptide may advantageously facilitate the expression of a recombinant TCR (including functional portions and functional variants thereof), polypeptide, and/or protein in a host cell. The linker peptide may comprise any suitable amino acid sequence. Linker sequences for single chain TCR constructs are well known in the art. Such a single chain construct may further comprise one, or two, constant domain sequences. Upon expression of the construct including the linker peptide by a host cell, the linker peptide may also be cleaved, resulting in separated α and β chains, and separated γ and δ chain.

The TCR of the invention may be modified in order to avoid mispairing of the TCR chains. The term "mispairing" shall relate to the incorrect pairing between a TCR chain of a TCR α/γ or β/δ transgene of the invention and an endogenous TCR α/γ or β/δ chain, respectively, and results in diluted cell surface expression of the transgenic TCRαβ/γδ heterodimer, which reduces the functional avidity of the modified T cells. Preferably, Q at position 44 in the TCR variable domain according to the IMGT numbering is substituted by another amino acid in one or both chains of the TCR of the invention. The substitution is preferably selected from the group consisting of R, D, E, K, I, W and V.

As already mentioned above, the binding functionality of the TCR of the invention may be provided in the framework of an antibody. For example, CDR sequences of the TCR of the invention, possibly including additional 3, 2 or 1 N and/or C terminal framework residues, may be directly grafted into an antibody variable heavy/light chain sequence. The term "antibody" in its various grammatical forms is used herein to refer to immunoglobulin molecules and immunologically active portions of immunoglobulin molecules, i.e., molecules that contain an antigen-binding site or a paratope. Such molecules are also referred to as "antigen binding fragments" of immunoglobulin molecules. The invention further provides an antibody, or antigen binding portion thereof, which specifically binds to the antigens described herein. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form.

The term "antibody" includes, but is not limited to, genetically engineered or otherwise modified forms of immunoglobulins, such as intrabodies, chimeric antibodies, fully human antibodies, humanized antibodies (e.g. generated by "CDR-grafting"), antibody fragments, and heteroconjugate antibodies (e.g., bispecific antibodies, diabodies, triabodies, tetra-bodies, etc.). The term "antibody" includes cys-diabodies and minibodies. Thus, each and every embodiment provided herein in regard to "antibodies", or "antibody like constructs" is also envisioned as, bi-specific antibodies, diabodies, scFv fragments, chimeric antibody receptor (CAR) constructs, diabody and/or minibody embodiments, unless explicitly denoted otherwise. The term "antibody" includes a polypeptide of the immunoglobulin family or a polypeptide comprising fragments of an immunoglobulin that is capable of non-covalently, reversibly, and in a specific manner binding a corresponding antigen, preferably the TAA of the invention, as disclosed herein. An exemplary antibody structural unit comprises a tetramer. In some embodiments, a full length antibody can be composed of two identical pairs of polypeptide chains, each pair having one "light" and one "heavy" chain (connected through a disulfide bond). Antibody structure and isotypes are well known to the skilled artisan (for example from Janeway's Immunobiology, 9th edition, 2016).

The recognized immunoglobulin genes of mammals include the kappa, lambda, alpha, gamma, delta, epsilon, and mu constant region genes, as well as the myriad immunoglobulin variable region genes (for more information on immunoglobulin genes see the international Im-MunoGeneTics information System®, Lefranc M-P et al, Nucleic Acids Res. 2015 January; 43(Database issue):D413-22; and http://www.imgt.org/). For full-length chains, the light chains are classified as either kappa or lambda. For full-length chains, the heavy chains are classified as gamma, mu, alpha, delta, or epsilon, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain (VL) and variable heavy chain (VH) refer to these regions of light and heavy chains respectively. As used in this invention, an "antibody" encompasses all variations of antibody and fragments thereof. Thus, within the scope of this concept are full length antibodies, chimeric antibodies, humanized antibodies, single chain antibodies (scFv), Fab, Fab', and multimeric versions of these fragments (e.g., F(ab')2) with the same, essentially the same or similar binding specificity. In some embodiments, the anti-body binds specifically to a peptide TAA of the invention. Preferred antigen recognizing constructs according to the invention include an antibody heavy chain, preferably the variable domain thereof, or an antigen binding fragment thereof, and/or an antibody light chain, preferably the variable domain thereof, or an antigen binding fragment thereof. Similarly, disulfide-stabilized variable region fragments (dsFv) can be prepared by recombinant DNA technology, antibody fragments of the invention, however, are not limited to these exemplary types of antibody fragments. Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles). In some instances, the TCR CDR3 sequence may be slightly modified, but preferably by not more than 3 amino acid residues, preferably only two and most preferably only one amino acid position, as compared to the CDR3 sequences provided in SEQ ID Nos: 3, 9, 15, 21, 27, 33, 39, 45, 51, 57, 63, 69, 75, 81, 87, 93, 99, 105, 111 and 117. Preferably, the antibodies comprise the CDR3, preferably all of CDR1 to CDR3 regions in the combination, as indicated for the TCR of the invention in table 1, in each case independently, optionally with not more than three or two, preferably one, amino acid substitution(s), insertion(s) and/or deletion(s) compared to these sequences.

Suitable methods of making antibodies are known in the art. For instance, standard hybridoma methods are described in, e.g., Kohler and Milstein, Eur. J. Immunol, 5, 51 1-519 (1976), Harlow and Lane (eds.), Antibodies: A Laboratory Manual, CSH Press (1988), and C. A. Janeway et al. (eds.), Immunobiology, 8 Ed., Garland Publishing, New York, N.Y. (201 1)). Alternatively, other methods, such as EBV-hybridoma methods (Haskard and Archer, J. Immunol. Methods, 74(2), 361-67 (1984), and Roder et al, Methods Enzymol, 121, 140-67 (1986)), and bacteriophage vector expression systems (see, e.g., Huse et al., Science, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266.

Some embodiments of the invention also pertain to TCRs, or functional fragments and polypeptides thereof, which are soluble TCRs. As used herein, the term "soluble T-cell receptor" refers to heterodimeric truncated variants of native TCRs, which comprise extracellular portions of the TCR α-chain and β-chain, for example linked by a disulfide bond, but which lack the transmembrane and cytosolic domains of the native protein. The terms "soluble T-cell receptor α-chain sequence and soluble T-cell receptor β-chain sequence" refer to TCR α-chain and β-chain sequences that lack the transmembrane and cytosolic domains. The sequence (amino acid or nucleic acid) of the soluble TCR α-chain and β-chains may be identical to the corresponding sequences in a native TCR or may comprise variant soluble TCR α-chain and β-chain sequences, as compared to the corresponding native TCR sequences. The term "soluble T-cell receptor" as used herein encompasses soluble TCRs with variant or non-variant soluble TCR α-chain and β-chain sequences. The variations may be in the variable or constant regions of the soluble TCR α-chain and β-chain sequences and can include, but are not limited to, amino acid deletion, insertion, substitution mutations as well as changes to the nucleic acid sequence, which do not alter the amino acid sequence. Soluble TCR of the invention in any case retain the binding functionality of their parent molecules.

The above problem is further solved by a nucleic acid encoding for an antigen recognizing construct of the invention, or any of the aforementioned protein or polypeptide constructs. The nucleic acid preferably (a) has a strand encoding for an antigen recognizing construct according to the invention; (b) has a strand complementary to the strand in (a); or (c) has a strand that hybridizes under stringent conditions with a molecule as described in (a) or (b). Stringent conditions are known to the person of skill in the art, specifically from Sambrook et al, "Molecular Cloning". In addition to that, the nucleic acid optionally has further sequences, which are necessary for expressing the nucleic acid sequence corresponding to the protein, specifically for expression in a mammalian/human cell. The nucleic acid used can be contained in a vector suitable for allowing expression of the nucleic acid sequence corresponding to the peptide in a cell. However, the nucleic acids can also be used to transform an antigen-presenting cell, which may not be restricted to classical antigen-presenting cells, such as dendritic cells, in such a way that they themselves produce the corresponding proteins on their cellular surface.

In some embodiments, the polypeptides of the antigen recognizing constructs can be encoded by nucleic acids and expressed in vivo or in vitro. Thus, in some embodiments, a nucleic acid encoding an antigen recognizing construct is provided. In some embodiments, the nucleic acid encodes one part or monomer of an antigen recognizing construct of the invention (for example one of two chains of a TCR of the invention), and/or another nucleic acid encodes another part or monomer of an antigen recognizing construct of the invention (for example the other of two chains of the TCR). In some embodiments, the nucleic acid encodes two or more antigen recognizing construct polypeptide chains, for example, at least 2 TCR chains. Nucleic acids encoding multiple antigen recognizing construct chains can include nucleic acid cleavage sites between at least two chain sequences, can encode transcription or translation start site between two or more chains sequences, and/or can encode proteolytic target sites between two or more antigen recognizing construct chains.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and can contain a natural, non-natural or altered internucleotide linkage, such as a phosphoroamidate linkage or a phosphorothioate linkage, instead of the phosphodiester found between the nucleotides of an unmodified oligonucleotide.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication. The nucleic acid can comprise any nucleotide sequence, which encodes any of the TCRs, polypeptides, or proteins, or functional portions or functional variants thereof described herein.

Furthermore, the invention provides a vector comprising a nucleic acid in accordance to the invention as described above. Desirably, the vector is an expression vector or a recombinant expression vector. The term "recombinant expression vector" refers in context of the present invention to a nucleic acid construct that allows for the expression of an mRNA, protein or polypeptide in a suitable host cell. The recombinant expression vector of the invention can be any suitable recombinant expression vector, and can be used to transform or transfect any suitable host. Suitable vectors include those designed for propagation and expansion or for expression or both, such as plasmids and viruses. Examples of animal expression vectors include pEUK-CI, pMAM, and pMAMneo. Preferably, the recombinant expression vector is a viral vector, e.g., a retroviral vector. The recombinant expression vector comprises regulatory sequences, such as transcription and translation initiation and termination codons, which are specific to the type of host cell (e.g., bacterium, fungus, plant, or animal), into which the vector is to be introduced and in which the expression of the nucleic acid of the invention may be performed. Furthermore, the vector of the invention may include one or more marker genes, which allow for selection of transformed or transfected hosts. The recombinant expression vector can comprise a native or normative promoter operably linked to the nucleotide sequence encoding the constructs of the invention, or to the nucleotide sequence, which is complementary to or which hybridizes to the nucleotide sequence encoding the constructs of the invention. The selections of promoters include, e.g., strong, weak, inducible, tissue-specific and developmental-specific promoters. The promoter can be a non-viral promoter or a viral promoter. The inventive recombinant expression vectors can be designed for either transient expression, for stable expression, or for both. Also, the recombinant expression vectors can be made for constitutive expression or for inducible expression.

The invention also pertains to a host cell comprising an antigen recognizing construct in accordance with the invention. Specifically, the host cell of the invention comprises a nucleic acid, or a vector as described herein above. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood leukocyte (PBL) or a peripheral blood mononuclear cell (PBMC). More preferably, the host cell is a T cell. The T cell can be any T cell, such as a cultured T cell, e.g., a primary T cell, or a T cell from a cultured T cell line, e.g., Jurkat, SupT1, etc., or a T cell obtained from a mammal, preferably a T cell or T cell precursor from a human patient. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, CD4-positive and/or CD8-positive, CD4-positive helper T cells, e.g., Th1 and Th2 cells, CD8-positive T cells (e.g., cytotoxic T cells), tumor infiltrating cells (TILs), memory T cells, naive T cells, and the like. Preferably, the T cell is a CD8-positive T cell or a CD4-positive T cell.

Preferably, the host cell of the invention is a lymphocyte, preferably, a T lymphocyte, such as a CD4-positive or CD8-positive T-cell. The host cell furthermore preferably is a tumor reactive T cell specific for TAA expressing tumor cells.

The objective of the invention is also solved by a method of manufacturing a TAA specific antigen recognizing construct, or of a TAA specific antigen recognizing construct expressing cell line, comprising a. Providing a suitable host cell,
b. Providing a genetic construct comprising a coding sequence encoding for an antigen recognizing construct according to the herein disclosed invention,
c. Introducing into said suitable host cell said genetic construct, and d. Expressing said genetic construct by said suitable host cell.

The method may further comprise a step of cell surface presentation of said antigen recognizing construct on said suitable host cell.

In other preferred embodiments, the genetic construct is an expression construct comprising a promoter sequence operably linked to said coding sequence.

Preferably, said antigen recognizing construct is of mammalian origin, preferably of human origin. The preferred suitable host cell for use in the method of the invention is a mammalian cell, such as a human cell, in particular a human T lymphocyte. T cells for use in the invention are described in detail herein above.

Also encompassed by the invention are embodiments, wherein said antigen recognizing construct is a modified TCR, wherein said modification is the addition of functional domains, such as a label or a therapeutically active substance. Furthermore, encompassed are TCR having alternative domains, such as an alternative membrane anchor domain instead of the endogenous transmembrane region.

Desirably, the transfection system for introducing the genetic construct into said suitable host cell is a retroviral vector system. Such systems are well known to the skilled artisan.

Also comprised by the present invention is in one embodiment the additional method step of isolation and purification of the antigen recognizing construct from the cell and, optionally, the reconstitution of the translated antigen recognizing construct-fragments in a T-cell.

In an alternative aspect of the invention a T-cell is provided obtained or obtainable by a method for the production of a T cell receptor (TCR), which is specific for tumorous cells and has high avidity as described herein above. Such a T cell is depending on the host cell used in the method of the invention, for example, a human or non-human T-cell, preferably a human TCR.

The term "isolated" as used herein in the context of a polypeptide, such as an antigen recognizing construct (an example of which could be an antibody), refers to a polypeptide that is purified from proteins or polypeptides or other contaminants that would interfere with its therapeutic, diagnostic, prophylactic, research or other use. An antigen recognizing construct according to the invention may be a recombinant, synthetic or modified (non-natural) antigen binding construct. The term "isolated" as used herein in the context of a nucleic acid or cells refers to a nucleic acid or cells that is/are purified from DNA, RNA, proteins or polypeptides or other contaminants (such as other cells) that would interfere with its therapeutic, diagnostic, prophylactic, research or other use, or it refers to a recombinant, synthetic or modified (non-natural) nucleic acid. In this context, a "recombinant" protein/polypeptide or nucleic acid is one made using recombinant techniques. Methods and techniques for the production of recombinant nucleic acids and proteins are well known in the art.

Treatment Methods and Diseases

One further aspect of the present invention relates to the herein disclosed antigen recognizing constructs, nucleic acids, vectors, pharmaceutical compositions and/or host cell for use in medicine. The use in medicine in one preferred embodiment includes the use in the diagnosis, prevention and/or treatment of a tumor disease, such as a malignant or benign tumor disease. The tumor disease is, for example, a tumor disease characterized by the expression of the TAA, in a cancer or tumor cell of said tumor disease.

With respect to the above mentioned medical applications of the antigen recognizing constructs and other materials derived therefrom, pertaining thereto or encoding the same, in accordance of the present disclosure, the to be treated and/or to be diagnosed diseases can be any proliferative disorder, preferably characterized by the expression of the TAA or TAA epitope sequence of the invention, for example any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, esophageal cancer, cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is cancer is cancer of the uterine cervix, oropharynx, anus, anal canal, anorectum, vagina, vulva, or penis. A particularly preferred cancer is a TAA positive cancer, including preferably, melanoma, gastrointestinal and gastric cancer.

The constructs, proteins, TCRs antibodies, polypeptides and nucleic acids of the invention are in particular for use in immune therapy, preferably, in adoptive T cell therapy. The administration of the compounds of the invention can, for example, involve the infusion of T cells of the invention into said patient. Preferably, such T cells are autologous T cells of the patient and in vitro transduced with a nucleic acid or antigen recognizing construct of the present invention.

The inventive antigen recognizing constructs, TCRs, polypeptides, proteins (including functional variants thereof), nucleic acids, recombinant expression vectors, host cells (including populations thereof), and antibodies (including antigen binding portions thereof), all of which are collectively referred to as "inventive TCR materials" hereinafter, can be formulated into a composition, such as a pharmaceutical composition. In this regard, the invention provides a pharmaceutical composition comprising any of the antigen recognizing constructs, TCRs, polypeptides, proteins, functional portions, functional variants, nucleic acids, expression vectors, host cells (including populations thereof), and antibodies (including antigen binding portions thereof) described herein, and a pharmaceutically acceptable carrier, excipient and/or stabilizer. The inventive pharmaceutical compositions containing any of the inventive TCR materials can comprise more than one inventive TCR material, e.g., a polypeptide and a nucleic acid, or two or more different TCRs (including functional portions and functional variants thereof). Alternatively, the pharmaceutical composition can comprise an inventive TCR material in combination with another pharmaceutically active agent(s) or drug(s), such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. Preferably, the carrier is a pharmaceutically acceptable carrier. With respect to pharmaceutical compositions, the carrier can be any of those conventionally used for the particular inventive TCR material under consideration. Such pharmaceutically acceptable carriers are well-known to those skilled in the art and are readily available to the public. It is preferred that the pharmaceutically acceptable carrier be one, which has no detrimental side effects or toxicity under the conditions of use.

Thus also provided is a pharmaceutical composition, comprising any of the herein described products of the invention and TCR materials of the invention, specifically any proteins, nucleic acids or host cells. In a preferred embodiment the pharmaceutical composition is for immune therapy, preferably adoptive cell therapy.

Preferably, the inventive TCR material is administered by injection, e.g., intravenously. When the inventive TCR material is a host cell expressing the inventive TCR (or functional variant thereof), the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered may be sufficient to affect, e.g., a therapeutic or prophylactic response, in the subject or animal over a reasonable time frame. For example, the dose of the inventive TCR material should be sufficient to bind to a cancer antigen, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

It is contemplated that the inventive pharmaceutical compositions, antigen recognizing constructs, TCRs (including functional variants thereof), polypeptides, proteins, nucleic acids, recombinant expression vectors, host cells, or populations of cells can be used in methods of treating or preventing cancer, or TAA-positive premalignancy. The inventive TCRs (and functional variants thereof) are believed to bind specifically to the TAA of the invention, such that the TCR (or related inventive polypeptide or protein and functional variants thereof), when expressed by or on a cell, such as a T cell, is able to mediate an immune response against a target cell expressing the TAA of the invention, preferably presenting TAA peptides via MHC I or II on the surface of said target cell. In this regard, the invention provides a method of treating or preventing a condition, in particular cancer, in a mammal, comprising administering to the mammal any of the pharmaceutical compositions, antigen recognizing constructs, in particular TCRs (and functional variants thereof), polypeptides, or proteins described herein, any nucleic acid or recombinant expression vector comprising a nucleotide sequence encoding any of the TCRs (and functional variants thereof), polypeptides, proteins described herein, or any host cell or population of cells comprising a nucleic acid or recombinant vector, which encodes any of the constructs of the invention (and functional variants thereof), polypeptides, or proteins described herein, in an amount effective to treat or prevent the condition in the mammal, wherein the condition is preferably cancer, such as a cancer expressing the TAA of the invention.

Examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of a condition in a mammal. Furthermore, the treatment or prevention provided by the inventive method can include treatment or prevention of one or more conditions or symptoms of the condition, e.g., cancer, being treated or prevented. For example, treatment or prevention can include promoting the regression of a tumor. Also, for purposes herein, "prevention" can encompass delaying the onset of the condition, or a symptom or condition thereof.

The present invention also relates to a method of treating cancer comprising administering a TCR, a nucleic acid, or a host cell of the present description in combination with at least one chemotherapeutic agent and/or radiation therapy.

Another aspect of the invention further pertains to a method for detecting a TAA protein, or a complex of MHC and the TAA protein (protein epitope of the TAA), in a (biological) sample—such as one obtained from a subject or patient—comprising contacting the sample with an antigen recognizing construct specifically binding to said TAA peptide, or to the TAA peptide/MHC complex, and detecting the binding between said antigen recognizing construct and said TAA peptide, or to the TAA peptide/MHC complex. In some embodiments, the antigen recognizing construct is a TCR or antibody, or similar constructs, or preferably the antigen recognizing construct according to the herein described invention. In some embodiments, the (biological) sample is a sample of a tumour or a cancer (such as one of those described elsewhere herein) for example a sample comprising tumour or cancer cells.

Also provided is a method of treating cancer in a subject in need thereof, comprising:
a) isolating a cell from said subject;
b) transforming the cell with at least one vector encoding an antigen recognizing construct of the present invention to produce a transformed cell;
c) expanding the transformed cell to produce a plurality of transformed cells; and
d) administering the plurality of transformed cells to said subject.

Also provided is a method of treating cancer in a subject in need thereof, comprising:
a) isolating a cell from a healthy donor;
b) transforming the cell with a vector encoding an antigen recognizing construct of the present invention to produce a transformed cell;
c) expanding the transformed cell to produce a plurality of transformed cells; and
d) administering the plurality of transformed cells to said subject.

Also provided is a method of detecting cancer in a biological sample comprising:

a) contacting the biological sample with an antigen recognizing construct of the present description;
b) detecting binding of the antigen recognizing construct to the biological sample.

In some embodiments, the method of detecting cancer is carried out in vitro, in vivo or in situ.

Also provided is a method of detecting the presence of a condition in a mammal. The method comprises (i) contacting a sample comprising one or more cells from the mammal with any of the inventive TCRs (and functional variants thereof), polypeptides, proteins, nucleic acids, recombinant expression vectors, host cells, populations of cells, antibodies, or antigen binding portions thereof, or pharmaceutical compositions described herein, thereby forming a complex, and detecting the complex, wherein detection of the complex is indicative of the presence of the condition in the mammal, wherein the condition is cancer, such as a TAA expressing malignancy.

With respect to the inventive method of detecting a condition in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the mammal. Preferably, the contacting is in vitro.

Also, detection of the complex can occur through any number of ways known in the art. For instance, the inventive antigen recognizing constructs (and functional variants thereof), polypeptides, proteins, nucleic acids, recombinant expression vectors, host cells, populations of cells, or antibodies or TCRs, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the above mentioned medical applications of the TCR material of the invention, the to be treated and/or diagnosed cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, esophageal cancer, cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is cancer is cancer of the uterine cervix, oropharynx, anus, anal canal, anorectum, vagina, vulva, or penis. A particularly preferred cancer is a TAA positive cancer, such as skin cancer, such as preferably melanoma, gastrointestinal or gastric cancer.

In general, the invention provides a method for treating a subject suffering from a tumor or tumor disease comprising the administration of the antigen recognizing constructs, nucleic acids, vectors, pharmaceutical compositions and/or host cell as disclosed by the present invention. Preferably the subject is a subject in need of such a treatment. The subject in preferred embodiments is a mammalian subject, preferably a human patient, suffering from a tumor or tumor disease, which is TAA-positive.

In view of the disclosure herein it will be appreciated that the invention furthermore pertains to the following items:

Item 1: An antigen recognizing construct comprising at least one complementary determining region (CDR) 3 having at least 50% sequence identity to an amino acid sequence selected from SEQ ID NOs. 3, 9, 15, 21, 27, 33, 39, 45, 51, 57, 63, 69, 75, 81, 87, 93, 99, 105, 111 and 117.

Item 2: The antigen recognizing construct according to item 1, wherein said antigen recognizing construct is capable of specifically and/or selectively binding to a TAA of the invention antigenic peptide.

Item 3: The antigen recognizing construct according to item 1 or 2, wherein the antigen recognizing construct is an antibody, or derivative or fragment thereof, or a T cell receptor (TCR), or a derivative or fragment thereof.

Item 4: The antigen recognizing construct according to any one of items 1 to 3, wherein said antigen recognizing construct binds to a human leucocyte antigen (HLA) presented TAA antigenic peptide, wherein said HLA is optionally type A2.

Item 5: The antigen recognizing construct according to any one of items 1 to 4, wherein the construct specifically and/or selectively binds to an epitope having the amino acid sequence selected from SEQ ID NO: 133 to 142, preferably to SEQ ID NO: 133.

Item 6: The antigen recognizing construct according to any one of items 1 to 5, wherein the construct is an α/β-TCR, or fragment or derivative thereof, or the construct is a γ/δ-TCR, or a fragment or derivative thereof.

Item 7: The antigen recognizing construct according to any one of items 1 to 6, characterized in that the construct is of human origin and specifically and/or selectively recognizes a TAA antigenic peptide.

Item 8: The antigen recognizing construct according to any one of items 1 to 7, wherein said antigen recognizing construct is capable of inducing an immune response in a subject, optionally wherein the immune response is characterized by an increase in interferon (IFN) γ levels.

Item 9: The antigen recognizing construct according to any one of items 1 to 8, comprising a TCR α or γ chain; and/or a TCR β or δ chain; wherein the TCR α or γ chain comprises a CDR3 having at least 50%, 60%, 70%, 80%, 90%, 95%, 98%, 99%, or 100% sequence identity to an amino acid sequence selected from SEQ ID Nos. 3, 15, 27, 39, 51, 63, 75, 87, 99 and 111, and/or wherein the TCR β or δ chain comprises a CDR3 having at least 50%, 60%, 70%, 80%, 90%, 95%, 98%, 99%, or 100% sequence identity to an amino acid sequence selected from SEQ ID Nos. 9, 21, 33, 45, 57, 69, 81, 93, 105 and 117.

Item 10: The antigen recognizing construct according to item 9, wherein the TCR α or γ chain further comprises a CDR1 having at least 50%, 60%, 70%, 80%, 90%, 95%, 98%, 99%, or 100% sequence identity to an amino acid sequence selected from SEQ ID Nos. 1, 13, 25, 37, 49, 61, 73, 85, 97 and 109; and/or a CDR2 having at least 50%, 60%, 70%, 80%, 90%, 95%, 98%, 99%, or 100% sequence identity to an amino acid sequence selected from SEQ ID Nos. 2, 14, 26, 38, 50, 62, 74, 86, 98 and 110.

Item 11: The antigen recognizing construct according to item 9 or 10, wherein the TCR β or δ chain further comprises a CDR1 having at least 50%, 60%, 70%, 80%, 90%, 95%, 98%, 99%, or 100% sequence identity to an amino acid sequence selected from SEQ ID Nos. 7, 19, 31, 43, 55, 67, 79, 91, 103 and 115; and/or a CDR2 having at least 50%, 60%, 70%, 80%, 90%, 95%, 98%, 99%, or 100% sequence identity to an amino acid sequence selected from SEQ ID Nos. 8, 20, 32, 44, 56, 68, 80, 92, 104 and 116.

Item 12: The antigen recognizing construct according to any of items 1 to 11, comprising a TCR variable chain region having at least 50%, 60%, 70%, 80%, 90%, 95%, 98%, 99%, or 100% sequence identity to an amino acid sequence selected from SEQ ID Nos. 4, 10, 16, 22, 28, 34, 40, 46, 52, 58, 64, 70, 76, 82, 88, 94, 100, 106, 112 and 118.

Item 13: The antigen recognizing construct according to any of items 1 to 12, wherein the construct is humanized, chimerized and/or murinized.

Item 14: The antigen recognizing construct according to any of items 1 to 13, comprising a binding fragment of a TCR, and wherein said binding fragment comprises CDR1 to CDR3 optionally selected from the CDR1 to CDR3 sequences having the amino acid sequences of SEQ ID Nos. 1, 2, 3, or 7, 8, 9 or 13, 14, 15, or 19, 20, 21, or 25, 26, 27 or 31, 32, 33 or 37, 38, 39 or 43, 44, 45 or 49, 50, 51 or 55, 56, 57 or 61, 62, 63 or 67, 68, 69 or 73, 74, 75 or 79, 80, 81 or 85, 86, 87 or 91, 92, 93 or 97, 98, 99 or 103, 104, 105 or 109, 110, 111 or 115, 116, 117.

Item 15: The antigen recognizing construct according to any of items 1 to 14, wherein the construct is a TCR, or a fragment thereof, composed of at least one TCR α and one TCR β chain sequence, wherein said TCR α chain sequence comprises the CDR1 to CDR3 sequences having the amino acid sequences of SEQ ID NO: 1 to 3, and said TCR β chain sequence comprises the CDR1 to CDR3 sequences having the amino acid sequences of SEQ ID NO: 7 to 9; or wherein said TCR α chain sequence comprises the CDR1 to CDR3 sequences having the amino acid sequences of SEQ ID NO: 13 to 15, and said TCR β chain sequence comprises the CDR1 to CDR3 sequences having the amino acid sequences of SEQ ID NO: 19 to 21; or wherein said TCR α chain sequence comprises the CDR1 to CDR3 sequences having the amino acid sequences of SEQ ID NO: 25 to 27, and said TCR β chain sequence comprises the CDR1 to CDR3 sequences having the amino acid sequences of SEQ ID NO: 31 to 33; or wherein said TCR α chain sequence comprises the CDR1 to CDR3 sequences having the amino acid sequences of SEQ ID NO: 37 to 39, and said TCR β chain sequence comprises the CDR1 to CDR3 sequences having the amino acid sequences of SEQ ID NO: 43 to 45; or wherein said TCR α chain sequence comprises the CDR1 to CDR3 sequences having the amino acid sequences of SEQ ID NO: 49 to 51, and said TCR β chain sequence comprises the CDR1 to CDR3 sequences having the amino acid sequences of SEQ ID NO: 55 to 57; or wherein said TCR α chain sequence comprises the CDR1 to CDR3 sequences having the amino acid sequences of SEQ ID NO: 61 to 63, and said TCR β chain sequence comprises the CDR1 to CDR3 sequences having the amino acid sequences of SEQ ID NO: 67 to 69; or wherein said TCR α chain sequence comprises the CDR1 to CDR3 sequences having the amino acid sequences of SEQ ID NO: 73 to 75, and said TCR β chain sequence comprises the CDR1 to CDR3 sequences having the amino acid sequences of SEQ ID NO: 79 to 81; or wherein said TCR α chain sequence comprises the CDR1 to CDR3 sequences having the amino acid sequences of SEQ ID NO: 85 to 87, and said TCR β chain sequence comprises the CDR1 to CDR3 sequences having the amino acid sequences of SEQ ID NO: 91 to 93; or wherein said TCR α chain sequence comprises the CDR1 to CDR3 sequences having the amino acid sequences of SEQ ID NO: 97 to 99, and said TCR β chain sequence comprises the CDR1 to CDR3 sequences having the amino acid sequences of SEQ ID NO: 103 to 105; or wherein said TCR α chain sequence comprises the CDR1 to CDR3 sequences having the amino acid sequences of SEQ ID NO: 109 to 111, and said TCR β chain sequence comprises the CDR1 to CDR3 sequences having the amino acid sequences of SEQ ID NO: 115 to 117.

Item 16: The antigen recognizing construct according to any of items 1 to 15, wherein the construct is a TCR, or a fragment thereof, comprising at least one TCR α and one TCR β chain sequence, wherein said TCR α chain sequence comprises a variable region sequence having the amino acid sequence of SEQ ID No. 4, and wherein said TCR β chain sequence comprises a variable region sequence having the amino acid sequence of SEQ ID No. 10; or wherein said TCR α chain sequence comprises a variable region sequence having the amino acid sequence of SEQ ID No. 16, and wherein said TCR β chain sequence comprises a variable region sequence having the amino acid sequence of SEQ ID No. 22; or wherein said TCR α chain sequence comprises a variable region sequence having the amino acid sequence of SEQ ID No. 28, and wherein said TCR β chain sequence comprises a variable region sequence having the amino acid sequence of SEQ ID No. 34; or wherein said TCR α chain sequence comprises a variable region sequence having the amino acid sequence of SEQ ID No. 40, and wherein said TCR β chain sequence comprises a variable region sequence having the amino acid sequence of SEQ ID No. 46; or wherein said TCR α chain sequence comprises a variable region sequence having the amino acid sequence of SEQ ID No. 52, and wherein said TCR β chain sequence comprises a variable region sequence having the amino acid sequence of SEQ ID No. 58; or wherein said TCR α chain sequence comprises a variable region sequence having the amino acid sequence of SEQ ID No. 64, and wherein said TCR β chain sequence comprises a variable region sequence having the amino acid sequence of SEQ ID No. 70; or wherein said TCR α chain sequence comprises a variable region sequence having the amino acid sequence of SEQ ID No. 76, and wherein said TCR β chain sequence comprises a variable region sequence having the amino acid sequence of SEQ ID No. 82; or wherein said TCR α chain sequence comprises a variable region sequence having the amino acid sequence of SEQ ID No. 88, and wherein said TCR β chain sequence comprises a variable region sequence having the amino acid sequence of SEQ ID No. 94; or wherein said TCR α chain sequence comprises a variable region sequence having the amino acid sequence of SEQ ID No. 100, and wherein said TCR β chain sequence comprises a variable region sequence having the amino acid sequence of SEQ ID No. 106; or wherein said TCR α chain sequence comprises a variable region sequence having the amino acid sequence of SEQ ID No. 112, and wherein said TCR β chain sequence comprises a variable region sequence having the amino acid sequence of SEQ ID No. 118.

Item 17: The antigen recognizing construct according to any of items 1 to 16, wherein the construct is a TCR, or a fragment thereof, further comprising a TCR constant region having at least 50%, 60%, 70%, 80%, 90%, 95%, 98%, 99%, or 100% sequence identity to an amino acid sequence selected from SEQ ID Nos. 5, 11, 17, 23, 29, 35, 41, 47, 53, 59, 65, 71, 77, 83, 89, 95, 101, 107, 113 and 119, preferably wherein the TCR is composed of at least one TCR α and one TCR β chain sequence, wherein the TCR α chain sequence comprises a constant region having at least 50%, 60%, 70%, 80%, 90%, 95%, 98%, 99%, or 100% sequence identity to an amino acid sequence selected from SEQ ID Nos. 5, 17, 29, 41, 53, 65, 77, 89, 101 and 113.

Item 18: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID No. 6, and a second TCR chain having at least 50%, 60%, 70%, 80%, 90%, 95%, 98%, 99%, or 100% sequence identity to the amino acid sequence of SEQ ID No. 12.

Item 19: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID No. 18, and a second TCR chain having at least 50%, 60%, 70%, 80%, 90%, 95%, 98%, 99%, or 100% sequence identity to the amino acid sequence of SEQ ID No. 24.

Item 20: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID No. 30, and a second TCR chain having at least 50%, 60%, 70%, 80%, 90%, 95%, 98%, 99%, or 100% sequence identity to the amino acid sequence of SEQ ID No. 36.

Item 21: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID No. 42, and a second TCR chain having at least 50%, 60%, 70%, 80%, 90%, 95%, 98%, 99%, or 100% sequence identity to the amino acid sequence of SEQ ID No. 48.

Item 22: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID No. 54, and a second TCR chain having at least 50%, 60%, 70%, 80%, 90%, 95%, 98%, 99%, or 100% sequence identity to the amino acid sequence of SEQ ID No. 60.

Item 23: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID No. 66, and a second TCR chain having at least 50%, 60%, 70%, 80%, 90%, 95%, 98%, 99%, or 100% sequence identity to the amino acid sequence of SEQ ID No. 72.

Item 24: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID No. 78, and a second TCR chain having at least 50%, 60%, 70%, 80%, 90%, 95%, 98%, 99%, or 100% sequence identity to the amino acid sequence of SEQ ID No. 84.

Item 25: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID No. 90, and a second TCR chain having at least 50%, 60%, 70%, 80%, 90%, 95%, 98%, 99%, or 100% sequence identity to the amino acid sequence of SEQ ID No. 96.

Item 26: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID No. 102, and a second TCR chain having at least 50%, 60%, 70%, 80%, 90%, 95%, 98%, 99%, or 100% sequence identity to the amino acid sequence of SEQ ID No. 108.

Item 27: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID No. 114, and a second TCR chain having at least 50%, 60%, 70%, 80%, 90%, 95%, 98%, 99%, or 100% sequence identity to the amino acid sequence of SEQ ID No. 120.

Item 28: A nucleic acid encoding for an antigen recognizing construct according to any one of items 1 to 27.

Item 29: A vector comprising a nucleic acid according to item 28.

Item 30: A host cell comprising an antigen recognizing construct according to any one of items 1 to 27, or a nucleic acid according to item 28, or a vector according to item 29.

Item 31: The host cell according to item 30, wherein the cell is a lymphocyte, preferably a T lymphocyte or T lymphocyte progenitor, more preferably a CD4 or CD8 positive T-cell.

Item 32: A pharmaceutical composition comprising the antigen recognizing construct according to any of items 1 to 27, or the nucleic acid according to item 28, or the vector according to item 29, or the host cell according to item 30 or 31, and a pharmaceutical acceptable carrier, stabilizer and/or excipient.

Item 33: The antigen recognizing construct according to any one of items 1 to 27, or a nucleic acid according to item 28, or a vector according to item 29, or a host cell according to item 30 or 31, or the pharmaceutical composition according to item 32, for use in medicine.

Item 34: The antigen recognizing construct, or the nucleic acid, or the vector, or the host cell, or the pharmaceutical composition, for use according to item 33, for use in the diagnosis, prevention, and/or treatment of a proliferative disease, wherein the disease comprises a malignant or benign tumor disease.

Item 35: The antigen recognizing construct, or the nucleic acid, or the vector, or the host cell, or the pharmaceutical composition, for use according to item 34, wherein the tumor disease is characterized by the expression of TAA in a tumor cell of the tumor disease.

Item 36: The antigen recognizing construct, or the nucleic acid, or the vector, or the host cell, or the pharmaceutical composition, for use according to any one of items 33 to 35, wherein the use in medicine is a use in immune therapy optionally comprising an adoptive cell transfer, wherein the immune therapy comprises adoptive autologous or heterologous T-cell therapy.

Item 37: A method of manufacturing a TAA specific antigen recognizing construct expressing cell line, comprising
a. providing a suitable host cell,
b. providing a genetic construct comprising a coding sequence encoding the antigen recognizing construct according to any of items 1 to 27,
c. introducing into said suitable host cell said genetic construct,
d. expressing said genetic construct by said suitable host cell.

Item 38: The method according to item 37, further comprising cell surface presentation of said antigen recognizing construct.

Item 39: The method according to item 37 or 38, wherein the genetic construct is an expression construct comprising a promoter sequence operably linked to said coding sequence.

Item 40: The method according to any one of items 37 to 39, wherein said antigen recognizing construct is of mammalian origin, preferably of human origin.

Item 41: The method according to any one of items 37 to 40, wherein said suitable host cell is a mammalian cell, optionally selected from a human cell or a human T lymphocyte.

Item 42: The method according to any of items 37 to 41, wherein said antigen recognizing construct is a modified TCR, wherein said modification comprises addition of a functional domain comprising a label, or an alternative domain comprising a membrane anchor domain.

Item 43: The method according to item 42, wherein said antigen recognizing construct is an alpha/beta TCR, gamma/delta TCR, or a single chain TCR (scTCR).

Item 44: The method according to any of items 37 to 43, wherein said genetic construct is introduced into said suitable host cell by retroviral transfection.

Item 45: The method according to any of items 37 to 44, further comprising the isolation and purification of the antigen recognizing construct from the suitable host cell and, optionally, reconstitution of the antigen recognizing construct in a T-cell.

Item 46: A method of killing target-cells in a patient, in which target cells aberrantly express TAA, the method comprising administering to the patient an effective number of T cells expressing a TCR of any of the aforementioned items, the nucleic acid, the expression vector, the host cell, and/or the pharmaceutical composition of the aforementioned items.

Item 47: The TCR of any of the aforementioned items, wherein the alpha chain comprises a TCR alpha variable domain at least 95% identical to the amino acid sequence of SEQ ID NO: 4; and the beta chain comprises a TCR beta variable domain at least 95% identical to SEQ ID NO: 10, and wherein the TCR specifically binds to a TAA-peptide MHC molecule complex.

Item 48: The TCR of any of the aforementioned items having at least one mutation in the alpha chain relative to SEQ ID NO: 4 and/or having at least one mutation in the beta chain relative to SEQ ID NO: 10, and wherein the TCR has a binding affinity for, and/or a binding half-life for, a TAA peptide-HLA molecule complex, which is at least double that of the unmutated TCR for the same peptide.

Item 49: The TCR of any of the aforementioned items having at least one mutation in the alpha chain relative to SEQ ID NO: 4 and/or having at least one mutation in the beta chain relative to SEQ ID NO: 10, and wherein the TCR has modified glycosylation compared to the unmutated TCR.

Item 50: The method of treating of the aforementioned items, wherein the TCR, the nucleic acid, the expression vector, the host cell or the pharmaceutical composition is administered in at least two administrations separated by at least 24 hours.

Item 51: The method of item 50, wherein the TCR, the nucleic acid, the expression vector, the host cell or the pharmaceutical composition is administered to the subject over a period of days, weeks or months, for example by local infusion, such as by an infusion pump and/or a catheter system.

Item 52: The method of item 51, wherein said local infusion is into a solid tumor, a blood vessel that feeds a solid tumor, and/or the area surrounding a solid tumor.

Item 52: The treatment method of any of the aforementioned items, wherein the TCR, the nucleic acid, the expression vector, the host cell or the pharmaceutical composition of is administered in a dose of about 104 to about 1010 cells per dose.

Item 53: A TCR comprising at least one alpha chain complementarity determining region (CDR) selected from the group consisting of an alpha chain CDR1, CDR2 and CDR3 of SEQ ID NO: 4 and/or at least one beta chain complementarity determining region (CDR) selected from the group consisting of a beta chain CDR1, CDR2 and CDR3 of SEQ ID NO: 10, and wherein the TCR specifically binds to a TAA peptide-MHC molecule complex.

The present invention will now be further described in the following examples with reference to the accompanying figures and sequences, nevertheless, without being limited thereto. For the purposes of the present invention, all references as cited herein are incorporated by reference in their entireties.

TABLE 1

TCR sequences of the invention

| SEQ ID NO: | TCR | Chain | Region | Sequence |
|---|---|---|---|---|
| 1 | R26P1A9 | alpha | CDR1 | TSINN |
| 2 | R26P1A9 | alpha | CDR2 | IRS |
| 3 | R26P1A9 | alpha | CDR3 | CLIGASGSRLTF |
| 4 | R26P1A9 | alpha | variable domain | METLLGVSLVILWLQLARVNSQQGEED PQALSIQEGENATMNCSYKTSINNLQW YRQNSGRGLVHLILIRSNEREKHSGRLR VTLDTSKKSSSLLITASRAADTASYFCLI GASGSRLTFGEGTQLTVNP |
| 5 | R26P1A9 | alpha | constant domain | DIQNPDPAVYQLRDSKSSDKSVCLFTDF DSQTNVSQSKDSDVYITDKTVLDMRSM DFKSNSAVAWSNKSDFACANAFNNSIIP EDTFFPSPESSCDVKLVEKSFETDTNLN FQNLSVIGFRILLLKVAGFNLLMTLRLWS S |

TABLE 1-continued

TCR sequences of the invention

| SEQ ID NO: | TCR | Chain | Region | Sequence |
|---|---|---|---|---|
| 6 | R26P1A9 | alpha | full-length | METLLGVSLVILWLQLARVNSQQGEED PQALSIQEGENATMNCSYKTSINNLQW YRQNSGRGLVHLILIRSNEREKHSGRLR VTLDTSKKSSSLLITASRAADTASYFCLI GASGSRLTFGEGTQLTVNPDIONPDPA VYQLRDSKSSDKSVCLFTDFDSQTNVS QSKDSDVYITDKTVLDMRSMDFKSNSA VAWSNKSDFACANAFNNSIIPEDTFFPS PESSCDVKLVEKSFETDTNLNFQNLSVI GFRILLLKVAGFNLLMTLRLWSS |
| 7 | R26P1A9 | beta | CDR1 | SGHDY |
| 8 | R26P1A9 | beta | CDR2 | FNNNVP |
| 9 | R26P1A9 | beta | CDR3 | CASSYFGWNEKLFF |
| 10 | R26P1A9 | beta | variable domain | MGSWTLCCVSLCILVAKHTDAGVIQSPR HEVTEMGQEVTLRCKPISGHDYLFWYR QTMMRGLELLIYFNNNVPIDDSGMPED RFSAKMPNASFSTLKIQPSEPRDSAVYF CASSYFGWNEKLFFGSGTQLSVL |
| 11 | R26P1A9 | beta | constant domain | EDLNKVFPPEVAVFEPSEAEISHTQKAT LVCLATGFFPDHVELSWWVNGKEVHS GVSTDPQPLKEQPALNDSRYCLSSRLR VSATFWQNPRNHFRCQVFYGLSEND EWTQDRAKPVTQIVSAEAWGRADCGF TSVSYQQGVLSATILYEILLGKATLYAVL VSALVLMAMVKRKDF |
| 12 | R26P1A9 | beta | full-length | MGSWTLCCVSLCILVAKHTDAGVIQSPR HEVTEMGQEVTLRCKPISGHDYLFWYR QTMMRGLELLIYFNNNVPIDDSGMPED RFSAKMPNASFSTLKIQPSEPRDSAVYF CASSYFGWNEKLFFGSGTQLSVLEDLN KVFPPEVAVFEPSEAEISHTQKATLVCL ATGFFPDHVELSWWVNGKEVHSGVST DPQPLKEQPALNDSRYCLSSRLRVSAT FWQNPRNHFRCQVFYGLSENDEWTQ DRAKPVTQIVSAEAWGRADCGFTSVSY QQGVLSATILYEILLGKATLYAVLVSALV LMAMVKRKDF |
| 13 | R26P2A6 | alpha | CDR1 | NSAFQY |
| 14 | R26P2A6 | alpha | CDR2 | TY |
| 15 | R26P2A6 | alpha | CDR3 | CAMSDVSGGYNKLIF |
| 16 | R26P2A6 | alpha | variable domain | MMKSLRVLLVILWLQLSWVWSQQKEVE QDPGPLSVPEGAIVSLNCTYSNSAFQYF MWYRQYSRKGPELLMYTYSSGNKEDG RFTAQVDKSSKYISLFIRDSQPSDSATY LCAMSDVSGGYNKLIFGAGTRLAVHP |
| 17 | R26P2A6 | alpha | constant domain | YIQNPDPAVYQLRDSKSSDKSVCLFTDF DSQTNVSQSKDSDVYITDKTVLDMRSM DFKSNSAVAWSNKSDFACANAFNNSIIP EDTFFPSPESSCDVKLVEKSFETDTNLN FQNLSVIGFRILLLKVAGFNLLMTLRLWS S |
| 18 | R26P2A6 | alpha | full-length | MMKSLRVLLVILWLQLSWVWSQQKEVE QDPGPLSVPEGAIVSLNCTYSNSAFQYF MWYRQYSRKGPELLMYTYSSGNKEDG RFTAQVDKSSKYISLFIRDSQPSDSATY LCAMSDVSGGYNKLIFGAGTRLAVHPYI QNPDPAVYQLRDSKSSDKSVCLFTDFD SQTNVSQSKDSDVYITDKTVLDMRSMD FKSNSAVAWSNKSDFACANAFNNSIIPE DTFFPSPESSCDVKLVEKSFETDTNLNF QNLSVIGFRILLLKVAGFNLLMTLRLWSS |

TABLE 1-continued

TCR sequences of the invention

| SEQ ID NO: | TCR | Chain | Region | Sequence |
|---|---|---|---|---|
| 19 | R26P2A6 | beta | CDR1 | MNHEY |
| 20 | R26P2A6 | beta | CDR2 | SMNVEV |
| 21 | R26P2A6 | beta | CDR3 | CASTTPDGTDEQFF |
| 22 | R26P2A6 | beta | variable domain | MGPQLLGYVVLCLLGAGPLEAQVTQNP RYLITVTGKKLTVTCSQNMNHEYMSWY RQDPGLGLRQIYYSMNVEVTDKGDVPE GYKVSRKEKRNFPLILESPSPNQTSLYF CASTTPDGTDEQFFGPTRLTVL |
| 23 | R26P2A6 | beta | constant domain | EDLKNVFPPEVAVFEPSEAEISHTQKAT LVCLATGFYPDHVELSWWVNGKEVHS GVSTDPQPLKEQPALNDSRYCLSSRLR VSATFWQNPRNHFRCQVQFYGLSEND EWTQDRAKPVTQIVSAEAWGRADCGF TSESYQQGVLSATILYEILLGKATLYAVL VSALVLMAMVKRKDSRG |
| 24 | R26P2A6 | beta | full-length | MGPQLLGYVVLCLLGAGPLEAQVTQNP RYLITVTGKKLTVTCSQNMNHEYMSWY RQDPGLGLRQIYYSMNVEVTDKGDVPE GYKVSRKEKRNFPLILESPSPNQTSLYF CASTTPDGTDEQFFGPTRLTVLEDLK NVFPPEVAVFEPSEAEISHTQKATLVCL ATGFYPDHVELSWWVNGKEVHSGVST DPQPLKEQPALNDSRYCLSSRLRVSAT FWQNPRNHFRCQVQFYGLSENDEWTQ DRAKPVTQIVSAEAWGRADCGFTSESY QQGVLSATILYEILLGKATLYAVLVSALV LMAMVKRKDSRG |
| 25 | R26P3H1 | alpha | CDR1 | VSGNPY |
| 26 | R26P3H1 | alpha | CDR2 | YITG |
| 27 | R26P3H1 | alpha | CDR3 | CAVRDMNRDDKIIF |
| 28 | R26P3H1 | alpha | variable domain | MASAPISMLAMLFTLSGLRAQSVAQPE DQVNVAEGNPLTVKCTYSVSGNPYLFW YVQYPNRGLQFLLKYITGDNLVKGSYGF EAEFNKSQTSFHLKKPSALVSDSALYFC AVRDMNRDDKIIFGKGTRLHILP |
| 29 | R26P3H1 | alpha | constant domain | NIQNPDPAVYQLRDSKSSDKSVCLFTDF DSQTNVSQSKDSDVYITDKTVLDMRSM DFKSNSAVAWSNKSDFACANAFNNSIIP EDTFFPSPESSCDVKLVEKSFETDTNLN FQNLSVIGFRILLLKVAGFNLLMTLRLWS S |
| 30 | R26P3H1 | alpha | full-length | MASAPISMLAMLFTLSGLRAQSVAQPE DQVNVAEGNPLTVKCTYSVSGNPYLFW YVQYPNRGLQFLLKYITGDNLVKGSYGF EAEFNKSQTSFHLKKPSALVSDSALYFC AVRDMNRDDKIIFGKGTRLHILPNIQNPD PAVYQLRDSKSSDKSVCLFTDFDSQTN VSQSKDSDVYITDKTVLDMRSMDFKSN SAVAWSNKSDFACANAFNNSIIPEDTFF PSPESSCDVKLVEKSFETDTNLFQNLS VIGFRILLLKVAGFNLLMTLRLWSS |
| 31 | R26P3H1 | beta | CDR1 | LNHDA |
| 32 | R26P3H1 | beta | CDR2 | SQIVND |
| 33 | R26P3H1 | beta | CDR3 | CASSRAEGGEQYF |
| 34 | R26P3H1 | beta | variable domain | MSNQVLCCVVLCFLGANTVDGGITQSP KYLFRKEGQNVTLSCEQNLNHDAMYW YRQDPGQGLRLIYYSQIVNDFQKGDIAE GYSVSREKKESFPLTVTSAQKNPTAFYL CASSRAEGGEQYFGPGTRLTVT |

TABLE 1-continued

TCR sequences of the invention

| SEQ ID NO: | TCR | Chain | Region | Sequence |
|---|---|---|---|---|
| 35 | R26P3H1 | beta | constant domain | EDLKNVFPPEVAVFEPSEAEISHTQKAT LVCLATGFYPDHVELSWWVNGKEVHS GVSTDPQPLKEQPALNDSRYCLSSRLR VSATFWQNPRNHFRCQVQFYGLSEND EWTQDRAKPVTQIVSAEAWGRADCGF TSESYQQGVLSATILYEILLGKATLYAVL VSALVLMAMVKRKDSRG |
| 36 | R26P3H1 | beta | full-length | MSNQVLCCVVLCFLGANTVDGGITQSP KYLFRKEGQNVTLSCEQNLNHDAMYW YRQDPGQGLRLIYYSQIVNDFQKGDIAE GYSVSREKKESFPLTVTSAQKNPTAFYL CASSRAEGGEQYFGPGTRLTVTEDLKN VFPPEVAVFEPSEAEISHTQKATLVCLA TGFYPDHVELSWWVNGKEVHSVSTD PQPLKEQPALNDSRYCLSSRLRVSATF WQNPRNHFRCQVQFYGLSENDEWTQ DRAKPVTQIVSAEAWGRADCGFTSESY QQGVLSATILYEILLGKATLYAVLSALV LMAMVKRKDSRG |
| 37 | R35P3A4 | alpha | CDR1 | DSASNY |
| 38 | R35P3A4 | alpha | CDR2 | IRS |
| 39 | R35P3A4 | alpha | CDR3 | CAASPTGGYNKLIF |
| 40 | R35P3A4 | alpha | variable domain | MTSIRAVFIFLWLQLDLVNGENVEQHPS TLSVQEGDSAVIKCTYSDSASNYFPWY KQELGKRPQLIIDIRSNVGEKKDQRIAVT LNKTAKHFSLHITETQPEDSAVYFCAAS PTGGYNKLIFGAGTRLAVHP |
| 41 | R35P3A4 | alpha | constant domain | YIQNPDPAVYQLRDSKSSDKSVCLFTDF DSQTNVSQSKDSDVYITDKTVLDMRSM DFKSNSAVAWSNKSDFACANAFNNSIIP EDTFFPSPESSCDVKLVEKSFETDTNLN FQNLSVIGFRILLLKVAGFNLLMTLRLWS S |
| 42 | R35P3A4 | alpha | full-length | MTSIRAVFIFLWLQLDLVNGENVEQHPS TLSVQEGDSAVIKCTYSDSASNYFPWY KQELGKRPQLIIDIRSNVGEKKDQRIAVT LNKTAKHFSLHITETQPEDSAVYFCAAS PTGGYNKLIFGAGTRLAVHPYIQNPDPA VYQLRDSKSSDKSVCLFTDFDSQTNVS QSKDSDVYITDKTVLDMRSMDFKSNSA VAWSNKSDFACANAFNNSIIPEDTFFPS PESSCDVKLVEKSFETDTNLNFQNLSVI GFRILLLKVAGFNLLMTLRLWSS |
| 43 | R35P3A4 | beta | CDR1 | MNHEY |
| 44 | R35P3A4 | beta | CDR2 | SVGAGI |
| 45 | R35P3A4 | beta | CDR3 | CASSLGGASQEQYF |
| 46 | R35P3A4 | beta | variable domain | MSIGLLCCAALSLLWAGPVNAGVTQTP KFQVLKTGQSMTLQCAQDMNHEYMSW YRQDPGMGLRLIHYSVGAGITDQGEVP NGYNVSRSTTEDFPLRLLSAAPSQTSV YFCASSLGGASQEQYFGPGTRLTVT |
| 47 | R35P3A4 | beta | constant domain | EDLKNVFPPEVAVFEPSEAEISHTQKAT LVCLATGFYPDHVELSWWVNGKEVHS GVSTDPQPLKEQPALNDSRYCLSSRLR VSATFWQNPRNHFRCQVQFYGLSEND EWTQDRAKPVTQIVSAEAWGRADCGF TSESYQQGVLSATILYEILLGKATLYAVL VSALVLMAMVKRKDSRG |
| 48 | R35P3A4 | beta | full-length | MSIGLLCCAALSLLWAGPVNAGVTQTP KFQVLKTGQSMTLQCAQDMNHEYMSW |

TABLE 1-continued

TCR sequences of the invention

| SEQ ID NO: | TCR | Chain | Region | Sequence |
|---|---|---|---|---|
| | | | | YRQDPGMGLRLIHYSVGAGITDQGEVP NGYNVSRSTTEDFPLRLLSAAPSQTSV YFCASSLGGASQEQYFGPGTRLTVTED LKNVFPPEVAVFEPSEAEISHTQKATLV CLATGFYPDHVELSWWVNGKEVHSGV STDPQPLKEQPALNDSRYCLSSRLRVS ATFWQNPRNHFRCQVQFYGLSENDEW TQDRAKPVTQIVSAEAWGRADCGFTSE SYQQGVLSATILYEILLGKATLYAVLVSA LVLMAMVKRKDSRG |
| 49 | R37P1C9 | alpha | CDR1 | TISGTDY |
| 50 | R37P1C9 | alpha | CDR2 | G |
| 51 | R37P1C9 | alpha | CDR3 | CILFNFNKFYF |
| 52 | R37P1C9 | alpha | variable domain | MKLVTSITVLLSLGIMGDAKTTQPNSME SNEEEPVHLPCNHSTISGTDYIHWYRQL PSQGPEYVIHGLTSNVNNRMASLAIAED RKSSTLILHRATLRDAAVYYCILFNFNKF YFGSGTKLNVKP |
| 53 | R37P1C9 | alpha | constant domain | NIQNPDPAVYQLRDSKSSDKSVCLFTDF DSQTNVSQSKDSDVYITDKTVLDMRSM DFKSNSAVAWSNKSDFACANAFNNSIIP EDTFFPSPESSCDVKLVEKSFETDTNLN FQNLSVIGFRILLLKVAGFNLLMTLRLWS S |
| 54 | R37P1C9 | alpha | full-length | MKLVTSITVLLSLGIMGDAKTTQPNSME SNEEEPVHLPCNHSTISGTDYIHWYRQL PSQGPEYVIHGLTSNVNNRMASLAIAED RKSSTLILHRATLRDAAVYYCILFNFNKF YFGSGTKLNVKPNIQNPDPAVYQLRDS KSSDKSVCLFTDFDSQTNVSQSKDSDV YITDKTVLDMRSMDFKSNSAVAWSNKS DFACANAFNNSIIPEDTFFPSPESSCDV KLVEKSFETDTNLNFQNLSVIGFRILLLK VAGFNLLMTLRLWSS |
| 55 | R37P1C9 | beta | CDR1 | LNHNV |
| 56 | R37P1C9 | beta | CDR2 | YYDKDF |
| 57 | R37P1C9 | beta | CDR3 | CATSSGETNEKLFF |
| 58 | R37P1C9 | beta | variable domain | MGPGLLHWMALCLLGTGHGDAMVIQN PRYQVTQFGKPVTLSCSQTLNHNVMY WYQQKSSQAPKLLFHYYDKDFNNEADT PDNFQSRRPNTSFCFLDIRSPGLGDAA MYLCATSSGETNEKLFFGSGTQLSVL |
| 59 | R37P1C9 | beta | constant domain | EDLNKVFPPEVAVFEPSEAEISHTQKAT LVCLATGFFPDHVELSWWVNGKEVHS GVSTDPQPLKEQPALNDSRYCLSSRLR VSATFWQNPRNHFRCQVQFYGLSEND EWTQDRAKPVTQIVSAEAWGRADCGF TSVSYQQGVLSATILYEILLGKATLYAVL VSALVLMAMVKRKDF |
| 60 | R37P1C9 | beta | full-length | MGPGLLHWMALCLLGTGHGDAMVIQN PRYQVTQFGKPVTLSCSQTLNHNVMY WYQQKSSQAPKLLFHYYDKDFNNEADT PDNFQSRRPNTSFCFLDIRSPGLGDAA MYLCATSSGETNEKLFFGSGTQLSVLE DLNKVFPPEVAVFEPSEAEISHTQKATL VCLATGFFPDHVELSWWVNGKEVHSG VSTDPQPLKEQPALNDSRYCLSSRLRV SATFWQNPRNHFRCQVQFYGLSENDE WTQDRAKPVTQIVSAEAWGRADCGFT SVSYQQGVLSATILYEILLGKATLYAVLV SALVLMAMVKRKDF |

TABLE 1-continued

TCR sequences of the invention

| SEQ ID NO: | TCR | Chain | Region | Sequence |
|---|---|---|---|---|
| 61 | R37P1H1 | alpha | CDR1 | TSESNYY |
| 62 | R37P1H1 | alpha | CDR2 | QEAY |
| 63 | R37P1H1 | alpha | CDR3 | CAFGYSGGGADGLTF |
| 64 | R37P1H1 | alpha | variable domain | MTRVSLLWAVVVSTCLESGMAQTVTQS QPEMSVQEAETVTLSCTYDTSESNYYL FWYKQPPSRQMILVIRQEAYKQQNATE NRFSVNFQKAAKSFSLKISDSQLGDTA MYFCAFGYSGGGADGLTFGKGTHLIIQ P |
| 65 | R37P1H1 | alpha | constant domain | YIQNPDPAVYQLRDSKSSDKSVCLFTDF DSQTNVSQSKDSDVYITDKTVLDMRSM DFKSNSAVAWSNKSDFACANAFNNSIIP EDTFFPSPESSCDVKLVEKSFETDTNLN FQNLSVIGFRILLLKVAGFNLLMTLRLWS S |
| 66 | R37P1H1 | alpha | full-length | MTRVSLLWAVVVSTCLESGMAQTVTQS QPEMSVQEAETVTLSCTYDTSESNYYL FWYKQPPSRQMILVIRQEAYKQQNATE NRFSVNFQKAAKSFSLKISDSQLGDTA MYFCAFGYSGGGADGLTFGKGTHLIIQ PYIQNPDPAVYQLRDSKSSDKSVCLFTD FDSQTNVSQSKDSDVYITDKTVLDMRS MDFKSNSAVAWSNKSDFACANAFNNSI IPEDTFFPSPESSCDVKLVEKSFETDTN LNFQNLSVIGFRILLLKVAGFNLLMTLRL WSS |
| 67 | R37P1H1 | beta | CDR1 | SGHDT |
| 68 | R37P1H1 | beta | CDR2 | YYEEEE |
| 69 | R37P1H1 | beta | CDR3 | CASSNEGQGWEAEAFF |
| 70 | R37P1H1 | beta | variable domain | MGPGLLCWALLCLLGAGLVDAGVTQSP THLIKTRGQQVTLRCSPKSGHDTVSWY QQALGQGPQFIFQYYEEEERQRGNFPD RFSGHQFPNYSSELNVNALLLGDSALYL CASSNEGQGWEAEAFFGQGTRLTVV |
| 71 | R37P1H1 | beta | constant domain | EDLNKVFPPEVAVFEPSEAEISHTQKAT LVCLATGFFPDHVELSWWVNGKEVHS GVSTDPQPLKEQPALNDSRYCLSSRLR VSATFWQNPRNHFRCQVQFYGLSEND EWTQDRAKPVTQIVSAEAWGRADCGF TSVSYQQGVLSATILYEILLGKATLYAVL VSALVLMAMVKRKDF |
| 72 | R37P1H1 | beta | full-length | MGPGLLCWALLCLLGAGLVDAGVTQSP THLIKTRGQQVTLRCSPKSGHDTVSWY QQALGQGPQFIFQYYEEEERQRGNFPD RFSGHQFPNYSSELNVNALLLGDSALYL CASSNEGQGWEAEAFFGQGTRLTVVE DLNKVFPPEVAVFEPSEAEISHTQKATL VCLATGFFPDHVELSWWVNGKEVHSG VSTDPQPLKEQPALNDSRYCLSSRLRV SATFWQNPRNHFRCQVQFYGLSENDE WTQDRAKPVTQIVSAEAWGRADCGFT SVSYQQGVLSATILYEILLGKATLYAVLV SALVLMAMVKRKDF |
| 73 | R42P3A9 | alpha | CDR1 | DSVNN |
| 74 | R42P3A9 | alpha | CDR2 | I |
| 75 | R42P3A9 | alpha | CDR3 | CAVHNFNKFYF |
| 76 | R42P3A9 | alpha | variable domain | MKRILGALLGLLSAQVCCVRGIQVEQSP PDLILQEGANSTLRCNFSDSVNNLQWF HQNPWGQLINLFYIPSGTKQNGRLSATT |

TABLE 1-continued

TCR sequences of the invention

| SEQ ID NO: | TCR | Chain | Region | Sequence |
|---|---|---|---|---|
| | | | | VATERYSLLYISSSQTTDSGVYFCAVHN FNKFYFGSGTKLNVKP |
| 77 | R42P3A9 | alpha | constant domain | NIQNPDPAVYQLRDSKSSDKSVCLFTDF DSQTNVSQSKDSDVYITDKTVLDMRSM DFKSNSAVAWSNKSDFACANAFNNSIIP EDTFFPSPESSCDVKLVEKSFETDTNLN FQNLSVIGFRILLLKVAGFNLLMTLRLWS S |
| 78 | R42P3A9 | alpha | full-length | MKRILGALLGLLSAQVCCVRGIQVEQSP PDLILQEGANSTLRCNFSDSVNNLQWF HQNPWGQLINLFYIPSGTKQNGRLSATT VATERYSLLYISSSQTTDSGVYFCAVHN FNKFYFGSGTKLNVKPNIQNPDPAVYQL RDSKSSDKSVCLFTDFDSQTNVSQSKD SDVYITDKTVLDMRSMDFKSNSAVAWS NKSDFACANAFNNSIIPEDTFFPSPESS CDVKLVEKSFETDTNLFQNLSVIGFRIL LLKVAGFNLLMTLRLWSS |
| 79 | R42P3A9 | beta | CDR1 | PRHDT |
| 80 | R42P3A9 | beta | CDR2 | FYEKMQ |
| 81 | R42P3A9 | beta | CDR3 | CASSLLGQGYNEQFF |
| 82 | R42P3A9 | beta | variable domain | MLSPDLPDSAWNTRLLCHVMLCLLGAV SVAAGVIQSPRHLIKEKRETATLKCYPIP RHDTVYWYQQGPGQDPQFLISFYEKM QSDKGSIPDRFSAQQFSDYHSELNMSS LELGDSALYFCASSLLGQGYNEQFFGP GTRLTVL |
| 83 | R42P3A9 | beta | constant domain | EDLKNVFPPEVAVFEPSEAEISHTQKAT LVCLATGFYPDHVELSWWVNGKEVHS GVSTDPQPLKEQPALNDSRYCLSSRLR VSATFWQNPRNHFRCQVQFYGLSEND EWTQDRAKPVTQIVSAEAWGRADCGF TSESYQQGVLSATILYEILLGKATLYAVL VSALVLMAMVKRKDSRG |
| 84 | R42P3A9 | beta | full-length | MLSPDLPDSAWNTRLLCHVMLCLLGAV SVAAGVIQSPRHLIKEKRETATLKCYPIP RHDTVYWYQQGPGQDPQFLISFYEKM QSDKGSIPDRFSAQQFSDYHSELNMSS LELGDSALYFCASSLLGQGYNEQFFGP GTRLTVLEDLKNVFPPEVAVFEPSEAEI SHTQKATLVCLATGFYPDHVELSWWVN GKEVHSGVSTDPQPLKEQPALNDSRYC LSSRLRVSATFWQNPRNHFRCQVQFY GLSENDEWTQDRAKPVTQIVSAEAWG RADCGFTSESYQQGVLSATILYEILLGK ATLYAVLVSALVLMAMVKRKDSRG |
| 85 | R43P3F2 | alpha | CDR1 | TRDTTYY |
| 86 | R43P3F2 | alpha | CDR2 | RNSF |
| 87 | R43P3F2 | alpha | CDR3 | CALSNNAGNMLTF |
| 88 | R43P3F2 | alpha | variable domain | MLTASLLRAVIASICVVSSMAQKVTQAQ TEISVVEKEDVTLDCVYETRDTTYYLFW YKQPPSGELVFLIRRNSFDEQNEISGRY SWNFQKSTSSFNFTITASQVVDSAVYF CALSNNAGNMLTFGGGTRLMVKP |
| 89 | R43P3F2 | alph | a constant domain | HIQNPDPAVYQLRDSKSSDKSVCLFTDF DSQTNVSQSKDSDVYITDKTVLDMRSM DFKSNSAVAWSNKSDFACANAFNNSIIP EDTFFPSPESSCDVKLVEKSFETDTNLN FQNLSVIGFRILLLKVAGFNLLMTLRLWS S |

TABLE 1-continued

TCR sequences of the invention

| SEQ ID NO: | TCR | Chain | Region | Sequence |
|---|---|---|---|---|
| 90 | R43P3F2 | alpha | full-length | MLTASLLRAVIASICVVSSMAQKVTQAQ TEISVVEKEDVTLDCVYETRDTTYYLFW YKQPPSGELVFLIRRNSFDEQNEISGRY SWNFQKSTSSFNFTITASQVVDSAVYF CALSNNNAGNMLTFGGGTRLMVKPHIQ NPDPAVYQLRDSKSSDKSVCLFTDFDS QTNVSQSKDSDVYITDKTVLDMRSMDF KSNSAVAWSNKSDFACANAFNNSIIPED TFFPSPESSCDVKLVEKSFETDTNLNFQ NLSVIGFRILLLKVAGFNLLMTLRLWSS |
| 91 | R43P3F2 | beta | CDR1 | PRHDT |
| 92 | R43P3F2 | beta | CDR2 | FYEKMQ |
| 93 | R43P3F2 | beta | CDR3 | CASSPTGTSGYNEQFF |
| 94 | R43P3F2 | beta | variable domain | MLSPDLPDSAWNTRLLCHVMLCLLGAV SVAAGVIQSPRHLIKEKRETATLKCYPIP RHDTVYWYQQGPGQDPQFLISFYEKM QSDKGSIPDRFSAQQFSDYHSELNMSS LELGDSALYFCASSPTGTSGYNEQFFG PGTRLTVL |
| 95 | R43P3F2 | beta | constant domain | EDLKNVFPPEVAVFEPSEAEISHTQKAT LVCLATGFYPDHVELSWWVNGKEVHS GVSTDPQPLKEQPALNDSRYCLSSRLR VSATFWQNPRNHFRCQVQFYGLSEND EWTQDRAKPVTQIVSAEAWGRADCGF TSESYQQGVLSATILYEILLGKATLYAVL VSALVLMAMVKRKDSRG |
| 96 | R43P3F2 | beta | full-length | MLSPDLPDSAWNTRLLCHVMLCLLGAV SVAAGVIQSPRHLIKEKRETATLKCYPIP RHDTVYWYQQGPGQDPQFLISFYEKM QSDKGSIPDRFSAQQFSDYHSELNMSS LELGDSALYFCASSPTGTSGYNEQFFG PGTRLTVLEDLKNVFPPEVAVFEPSEAE ISHTQKATLVCLATGFYPDHVELSWWV NGKEVHSGVSTDPQPLKEQPALNDSRY CLSSRLRVSATFWQNPRNHFRCQVQF YGLSENDEWTQDRAKPVTQIVSAEAW GRADCGFTSESYQQGVLSATILYEILLG KATLYAVLVSALVLMAMVKRKDSRG |
| 97 | R43P3G5 | alpha | CDR1 | SSNFYA |
| 98 | R43P3G5 | alpha | CDR2 | MTL |
| 99 | R43P3G5 | alpha | CDR3 | CALNRDDKIIF |
| 100 | R43P3G5 | alpha | variable domain | MEKNPLAAPLLILWFHLDCVSSILNVEQ SPQSLHVQEGDSTNFTCSFPSSNFYAL HWYRWETAKSPEALFVMTLNGDEKKK GRISATLNTKEGYSYLYIKGSQPEDSAT YLCALNRDDKIIFGKGTRLHILP |
| 101 | R43P3G5 | alpha | constant domain | NIQNPDPAVYQLRDSKSSDKSVCLFTDF DSQTNVSQSKDSDVYITDKTVLDMRSM DFKSNSAVAWSNKSDFACANAFNNSIIP EDTFFPSPESSCDVKLVEKSFETDTNLN FQNLSVIGFRILLLKVAGFNLLMTLRLWS S |
| 102 | R43P3G5 | alpha | full-length | MEKNPLAAPLLILWFHLDCVSSILNVEQ SPQSLHVQEGDSTNFTCSFPSSNFYAL HWYRWETAKSPEALFVMTLNGDEKKK GRISATLNTKEGYSYLYIKGSQPEDSAT YLCALNRDDKIIFGKGTRLHILPNIQNPD PAVYQLRDSKSSDKSVCLFTDFDSQTN VSQSKDSDVYITDKTVLDMRSMDFKSN SAVAWSNKSDFACANAFNNSIIPEDTFF PSPESSCDVKLVEKSFETDTNLNFQNLS VIGFRILLLKVAGFNLLMTLRLWSS |

TABLE 1-continued

TCR sequences of the invention

| SEQ ID NO: | TCR | Chain | Region | Sequence |
|---|---|---|---|---|
| 103 | R43P3G5 | beta | CDR1 | MDHEN |
| 104 | R43P3G5 | beta | CDR2 | SYDVKM |
| 105 | R43P3G5 | beta | CDR3 | CASRLPSRTYEQYF |
| 106 | R43P3G5 | beta | variable domain | MGIRLLCRVAFCFLAVGLVDVKVTQSSR YLVKRTGEKVFLECVQDMDHENMFWY RQDPGLGLRLIYFSYDVKMKEKGDIPEG YSVSREKKERFSLILESASTNQTSMYLC ASRLPSRTYEQYFGPGTRLTVT |
| 107 | R43P3G5 | beta | constant domain | EDLKNVFPPEVAVFEPSEAEISHTQKAT LVCLATGFYPDHVELSWWVNGKEVHS GVSTDPQPLKEQPALNDSRYCLSSRLR VSATFWQNPRNHFRCQVQFYGLSEND EWTQDRAKPVTQIVSAEAWGRADCGF TSESYQQGVLSATILYEILLGKATLYAVL VSALVLMAMVKRKDSRG |
| 108 | R43P3G5 | beta | full-length | MGIRLLCRVAFCFLAVGLVDVKVTQSSR YLVKRTGEKVFLECVQDMDHENMFWY RQDPGLGLRLIYFSYDVKMKEKGDIPEG YSVSREKKERFSLILESASTNQTSMYLC ASRLPSRTYEQYFGPGTRLTVTEDLKN VFPPEVAVFEPSEAEISHTQKATLVCLA TGFYPDHVELSWWVNGKEVHSGVSTD PQPLKEQPALNDSRYCLSSRLRVSATF WQNPRNHFRCQVQFYGLSENDEWTQ DRAKPVTQIVSAEAWGRADCGFTSESY QQGVLSATILYEILLGKATLYAVLVSALV LMAMVKRKDSRG |
| 109 | R59P2E7 | alpha | CDR1 | DSAIYN |
| 110 | R59P2E7 | alpha | CDR2 | IQS |
| 111 | R59P2E7 | alpha | CDR3 | CAVNSDYKLSF |
| 112 | R59P2E7 | alpha | variable domain | METLLGLLILWLQLQWVSSKQEVTQIPA ALSVPEGENLVLNCSFTDSAIYNLQWFR QDPGKGLTSLLLIQSSREQTSGRLNA SLDKSSGRSTLYIAASQPGDSATYLCAV NSDYKLSFGAGTTVTVRA |
| 113 | R59P2E7 | alpha | constant domain | NIQNPDPAVYQLRDSKSSDKSVCLFTDF DSQTNVSQSKDSDVYITDKTVLDMRSM DFKSNSAVAWSNKSDFACANAFNNSIIP EDTFFPSPESSCDVKLVEKSFETDTNLN FQNLSVIGFRILLLKVAGFNLLMTLRLWS S |
| 114 | R59P2E7 | alpha | full-length | METLLGLLILWLQLQWVSSKQEVTQIPA ALSVPEGENLVLNCSFTDSAIYNLQWFR QDPGKGLTSLLLIQSSREQTSGRLNA SLDKSSGRSTLYIAASQPGDSATYLCAV NSDYKLSFGAGTTVTVRANIQNPDPAV YQLRDSKSSDKSVCLFTDFDSQTNVSQ SKDSDVYITDKTVLDMRSMDFKSNSAV ESSCDVKLVEKSFETDTNLNFQNLSVIG FRILLLKVAGFNLLMTLRLWSS |
| 115 | R59P2E7 | beta | CDR1 | PHRDT |
| 116 | R59P2E7 | beta | CDR2 | FYEKMQ |
| 117 | R59P2E7 | beta | CDR3 | CASSLGLGTGDYGYTF |
| 118 | R59P2E7 | beta | variable domain | MLSPDLPDSAWNTRLLCHVMLCLLGAV SVAAGVIQSPRHLIKEKRETATLKCYPIP RHDTVYWYQQGPGQDPQFLISFYEKM |

TABLE 1-continued

TCR sequences of the invention

| SEQ ID NO: | TCR | Chain | Region | Sequence |
|---|---|---|---|---|
| | | | | QSDKGSIPDRFSAQQFSDYHSELNMSS LELGDSALYFCASSLGLGTGDYGYTFG SGTRLTVV |
| 119 | R59P2E7 | beta | constant domain | EDLNKVFPPEVAVFEPSEAEISHTQKAT LVCLATGFFPDHVELSWWVNGKEVHS GVSTDPQPLKEQPALNDSRYCLSSRLR VSATFWQNPRNHFRCQVQFYGLSEND EWTQDRAKPVTQIVSAEAWGRADCGF TSVSYQQGVLSATILYEILLGKATLYAVL VSALVLMAMVKRKDF |
| 120 | R59P2E7 | beta | full-length | MLSPDLPDSAWNTRLLCHVMLCLLGAV SVAAGVIQSPRHLIKEKRETATLKCYPIP RHDTVYWYQQGPGQDPQFLISFYEKM QSDKGSIPDRFSAQQFSDYHSELNMSS LELGDSALYFCASSLGLGTGDYGYTFG SGTRLTVVEDLNKVFPPEVAVFEPSEAE ISHTQKATLVCLATGFFPDHVELSWWV NGKEVHSGVSTDPQPLKEQPALNDSRY CLSSRLRVSATFWQNPRNHFRCQVQF YGLSENDEWTQDRAKPVTQIVSAEAW GRADCGFTSVSYQQGVLSATILYEILLG KATLYAVLVSALVLMAMVKRKDF |
| 121 | 1G4 | alpha | CDR1 | DSAIYN |
| 122 | 1G4 | alpha | CDR2 | IQS |
| 123 | 1G4 | alpha | CDR3 | CAVRPTSGGSYIPTF |
| 124 | 1G4 | alpha | variable domain | METLLGLLILWLQLQWVSSKQEVTQIPA ALSVPEGENLVLNCSFTDSAIYNLQWFR QDPGKGLTSLLLIQSSREQTSGRLNA SLDKSSGRSTLYIAASQPGDSATYLCAV RPTSGGSYIPTFGRGTSLIVHP |
| 125 | 1G4 | alpha | constant domain | YIQNPDPAVYQLRDSKSSDKSVCLFTDF DSQTNVSQSKDSDVYITDKTVLDMRSM DFKSNSAVAWSNKSDFACANAFNNSIIP EDTFFPSPESSCDVKLVEKSFETDTNLN FQNLSVIGFRILLLKVAGFNLLMTLRLWS S |
| 126 | 1G4 | alpha | full-length | METLLGLLILWLQLQWVSSKQEVTQIPA ALSVPEGENLVLNCSFTDSAIYNLQWFR QDPGKGLTSLLLIQSSREQTSGRLNA SLDKSSGRSTLYIAASQPGDSATYLCAV RPTSGGSYIPTFGRGTSLIVHPYIQNPD PAVYQLRDSKSSDKSVCLFTDFDSQTN VSQSKDSDVYITDKTVLDMRSMDFKSN SAVAWSNKSDFACANAFNNSIIPEDTFF PSPESSCDVKLVEKSFETDTNLNFQNLS VIGFRILLLKVAGFNLLMTLRLWSS |
| 127 | 1G4 | beta | CDR1 | MNHEY |
| 128 | 1G4 | beta | CDR2 | SVGAGI |
| 129 | 1G4 | beta | CDR3 | CASSYVGNTGELFF |
| 130 | 1G4 | beta | variable domain | MSIGLLCCAALSLLWAGPVNAGVTQTP KFQVLKTGQSMTLQCAQDMNHEYMSW YRQDPGMGLRLIHYSVGAGITDQGEVP NGYNVSRSTTEDFPLRLLSAAPSQTSV YFCASSYVGNTGELFFGEGSRLTVL |
| 131 | 1G4 | beta | constant domain | EDLKNVFPPEVAVFEPSEAEISHTQKAT LVCLATGFYPDHVELSWWVNGKEVHS GVSTDPQPLKEQPALNDSRYCLSSRLR VSATFWQNPRNHFRCQVQFYGLSEND EWTQDRAKPVTQIVSAEAWGRADCGF TSESYQQGVLSATILYEILLGKATLYAVL VSALVLMAMVKRKDSRG |

TABLE 1-continued

TCR sequences of the invention

| SEQ ID NO: | TCR | Chain | Region | Sequence |
|---|---|---|---|---|
| 132 | 1G4 | beta | full-length | MSIGLLCCAALSLLWAGPVNAGVTQTP KFQVLKTGQSMTLQCAQDMNHEYMSW YRQDPGMGLRLIHYSVGAGITDQGEVP NGYNVSRSTTEDFPLRLLSAAPSQTSV YFCASSYVGNTGELFFGEGSRLTVLED LKNVFPPEVAVFEPSEAEISHTQKATLV CLATGFYPDHVELSWWVNGKEVHSGV STDPQPLKEQPALNDSRYCLSSRLRVS ATFWQNPRNHFRCQVQFYGLSENDEW TQDRAKPVTQIVSAEAWGRADCGFTSE SYQQGVLSATILYEILLGKATLYAVLVSA LVLMAMVKRKDSRG |

TABLE 2

Peptide sequences of the invention

| Peptide Code | Sequence | SEQ ID NO: |
|---|---|---|
| MAGEA1-003 | KVLEYVIKV | 133 |
| MAGEA1-003_A1 | AVLEYVIKV | 134 |
| MAGEA1-003_A2 | KALEYVIKV | 135 |
| MAGEA1-003_A3 | KVAEYVIKV | 136 |
| MAGEA1-003_A4 | KVLAYVIKV | 137 |
| MAGEA1-003_A5 | KVLEAVIKV | 138 |
| MAGEA1-003_A6 | KVLEYAIKV | 139 |
| MAGEA1-003_A7 | KVLEYVAKV | 140 |
| MAGEA1-003_A8 | KVLEYVIAV | 141 |
| MAGEA1-003_A9 | KVLEYVIKA | 142 |
| TMEM175-001 | ILLPYVSKV | 143 |
| EPAS-001 | KALEGFIAV | 144 |
| PTRF-001 | KLLEKVRKV | 145 |
| GALNTL4-001 | KLTEYVDKV | 146 |
| PSME2-001 | KVLERVNAV | 147 |
| KIAA103-002 | KVLNKVITV | 148 |
| NSD1-001 | KVQEQVHKV | 149 |
| TBC1D9-002 | LLLPDVIKV | 150 |
| TMTC4-001 | NVLEIVQKV | 151 |
| RASAL2-002 | SVLEPVISV | 152 |
| NYESO1-001 | SLLMWITQV | 153 |
| MAGEA1-003_T1 | TVLEYVIKV | 154 |
| MAGEA1-003_T2 | KTLEYVIKV | 155 |
| MAGEA1-003_T3 | KVTEYVIKV | 156 |
| MAGEA1-003_T4 | KVLTYVIKV | 157 |
| MAGEA1-003_T5 | KVLETVIKV | 158 |
| MAGEA1-003_T6 | KVLEYTIKV | 159 |
| MAGEA1-003_T7 | KVLEYVTKV | 160 |
| MAGEA1-003_T8 | KVLEYVITV | 161 |
| MAGEA1-003_T9 | KVLEYVIKT | 162 |

EXAMPLES

Ten MAGEA1-003-specific TCRs (R26P1A9, R26P2A6, R26P3H1, R35P3A4, R37P1C9, R37P1H1, R42P3A9, R43P3F2, R43P3G5 and R59P2E7, see Table 1), each encoding tumor specific TCR-alpha and TCR-beta chains, were isolated and amplified from T-cells of healthy donors. Cells from healthy donors were in vitro stimulated according to a method previously described (Walter et al., 2003 J Immunol., November 15; 171(10):4974-8) and target-specific cells were single-cell sorted using HLA-A*02 multimers and then used for subsequent TCR isolation. TCR sequences were isolated via 5' RACE by standard methods as described by e.g. Molecular Cloning a laboratory manual fourth edition by Green and Sambrook. The alpha and beta variable regions of TCRs R26P1A9, R26P2A6, R26P3H1R42P3A9, R43P3F2, R43P3G5, R59P2E7 35P3A4, R37P1C9 and R37P1H1 were sequenced and expression constructs were generated by gene synthesis for further functional characterization.

R26P1A9, R26P2A6, R26P3H1, R42P3A9, R43P3F2, R43P3G5 and R59P2E7 are derived from HLA-A*02 negative donor (allo-reactive setting) and R35P3A4, R37P1C9 and R37P1H1 are derived from a HLA-A*02 positive donor.

TCRs of interest were expressed in human T cells by transduction, e.g. through mRNA electroporation or lentiviral transduction. For lentiviral transduction, PBMC were thawed and rested overnight, and then activated using immobilized antibodies. Activated cells were transduced using a lentiviral vector encoding the MAGEA1-specific TCR and expanded in the presence of cytokines. T cells were harvested and concentrated by centrifugation, then cryopreserved.

The T cells were assessed for IFN-γ release after co-culture with different target cells, such as T2 cells loaded with different peptides as well as tumor cell lines and primary cells from healthy tissues. T-cell activation data are shown in absolute IFNγ levels or a background subtracted way as indicated below.

Figure 33:
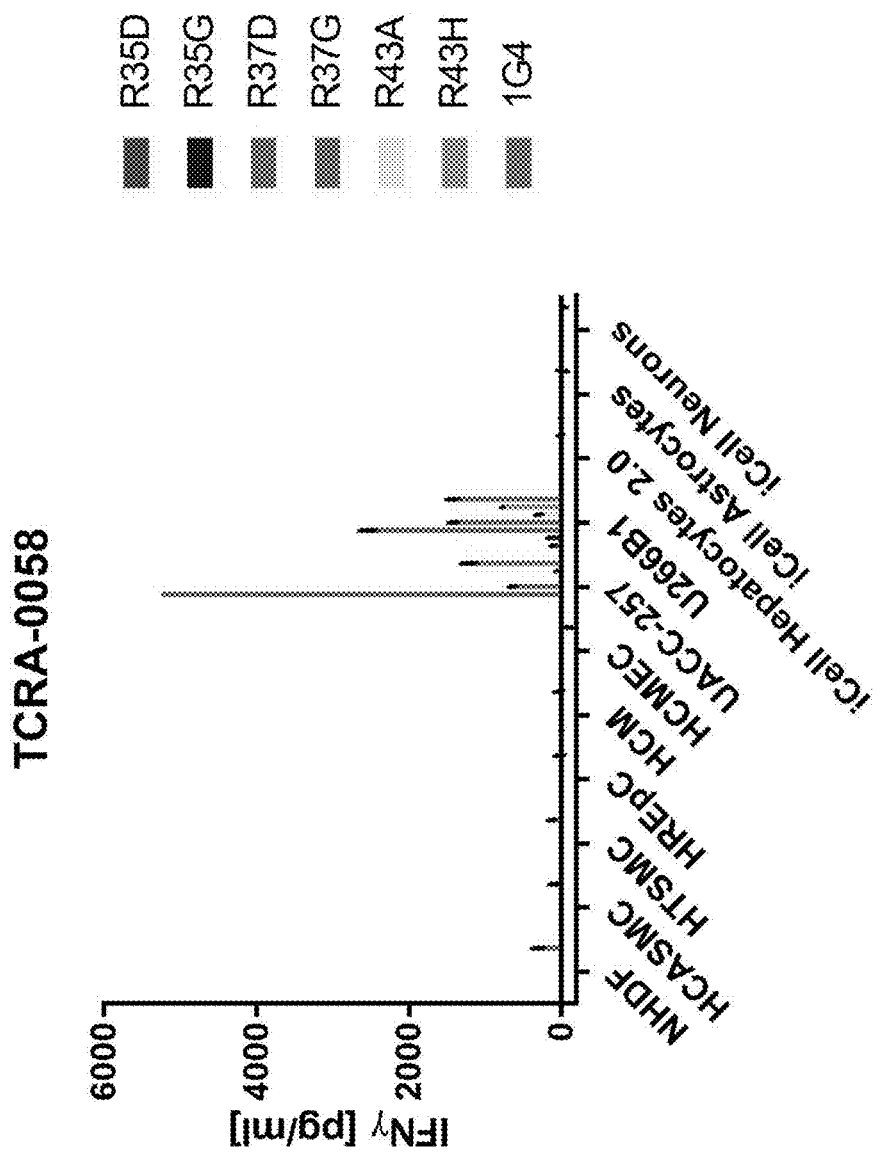

Efficacy of CD8+ T cells expressing TCRs R35P3A4, R37P1C9 and R43P3G5 was determined e.g. by T cell activation studies (IFNγ release) or killing assays using different tumor cell lines as target cells. The characterization of the safety profile of TCRs of interest was approached by testing the potential activation of TCR-expressing T cells upon co-culture with isolated primary cell types from healthy tissues and induced pluripotent stem cell (iPSC)-derived cell types from HLA-A*02-positive donors (FIG. 33). Cell types were selected in a manner to cover critical organs like brain, heart and liver and different cell types as epithelium, endothelium or smooth muscle. Tumor cell lines were analyzed side-by-side as positive and negative controls.

Background subtraction method for IFNγ release:

$$Mean_{bg(TCRoi;\ co)} = [mean_{(TCRoi;\ co)} - mean_{(TCRoi;\ effector\ only)}] - [mean_{(mock;\ co)} - mean_{(mock;\ effector\ only)}]$$

The respective $SD_{bg}$ was calculated:

$$SD_{bg\ (TCRoi;\ co)} = [SD_{(TCRoi;\ co)}^2 + SD_{(TCRoi;\ effector\ only)}^2 + SD_{(mock;co)}^2 + SD_{(mock;\ effector\ only)}^2]^{[1/2]}$$

TCRoi=effector cells expressing TCR of interest
Mock=effector cells without exogenous TCR expression
Co=effector cells co-cultured with target cells
Effector only=effector cells not co-cultured
Mean$_{(bg)}$=mean IFNγ release (background subtracted)
SD$_{(bg)}$=standard deviation (background subtracted)

Example 1: T-Cell Receptor R26P1 A9

Figure 1:
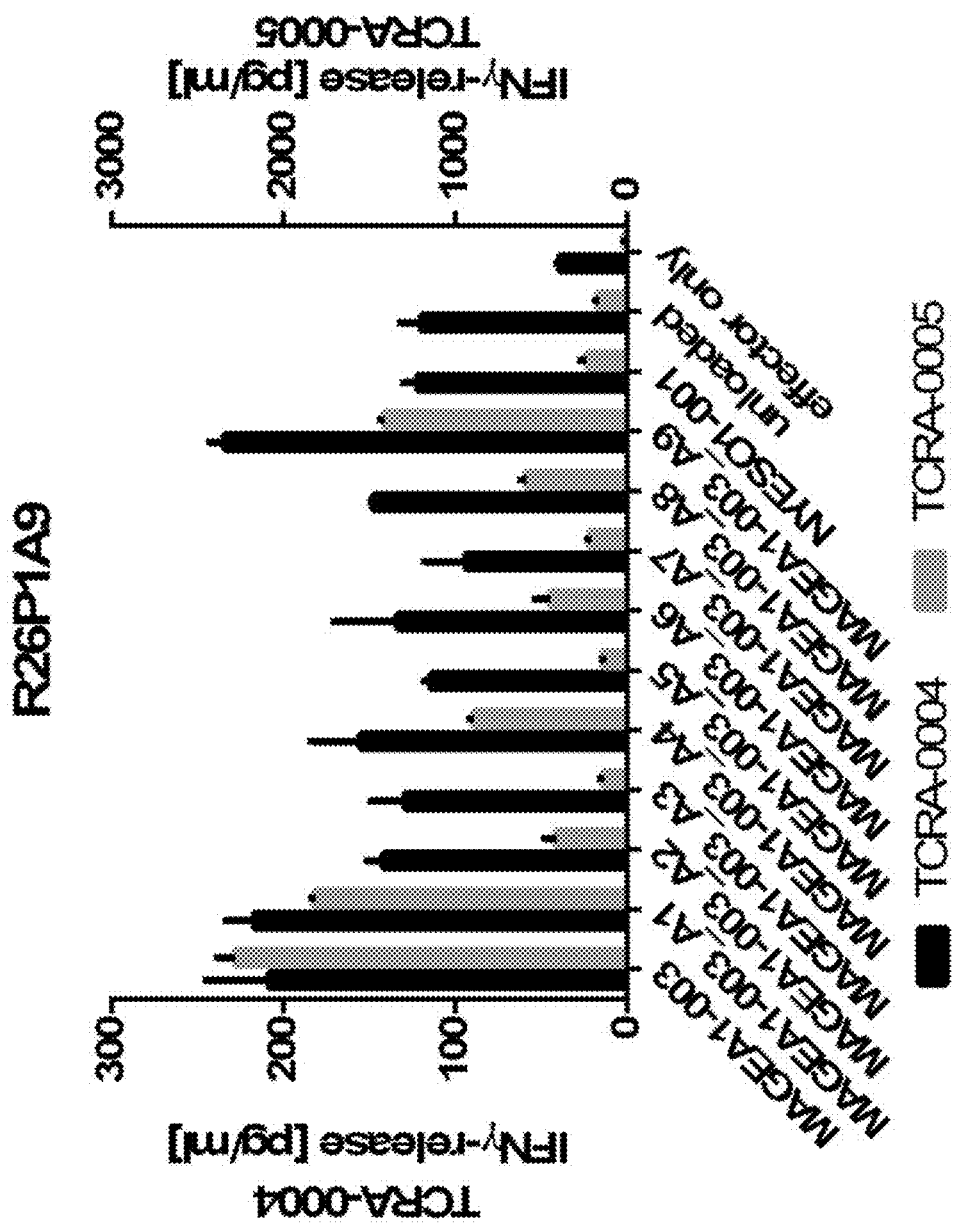
FIGS. 1-44 depict embodiments of the disclosure as described herein.
Figure 11:
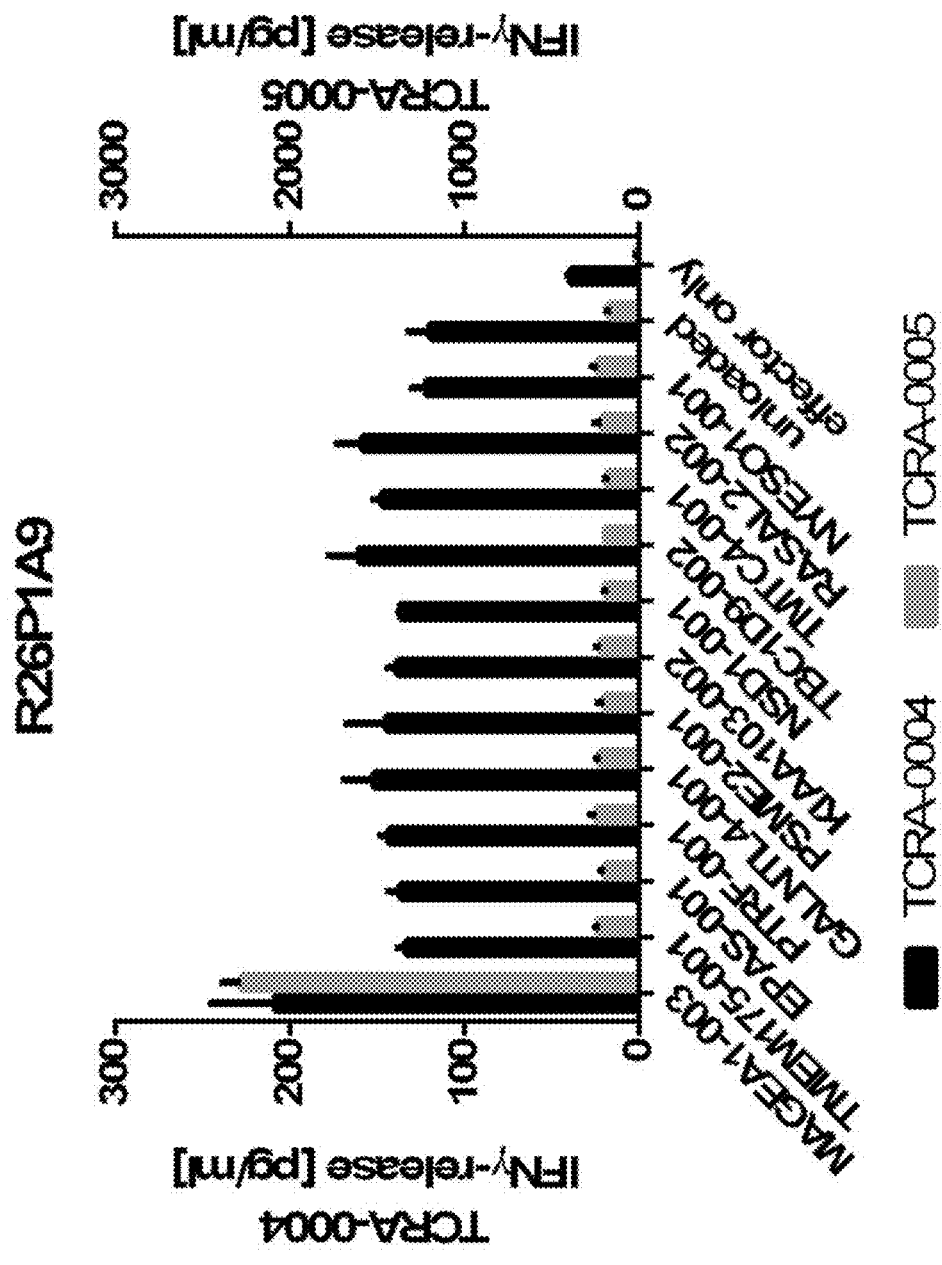
Figure 22:
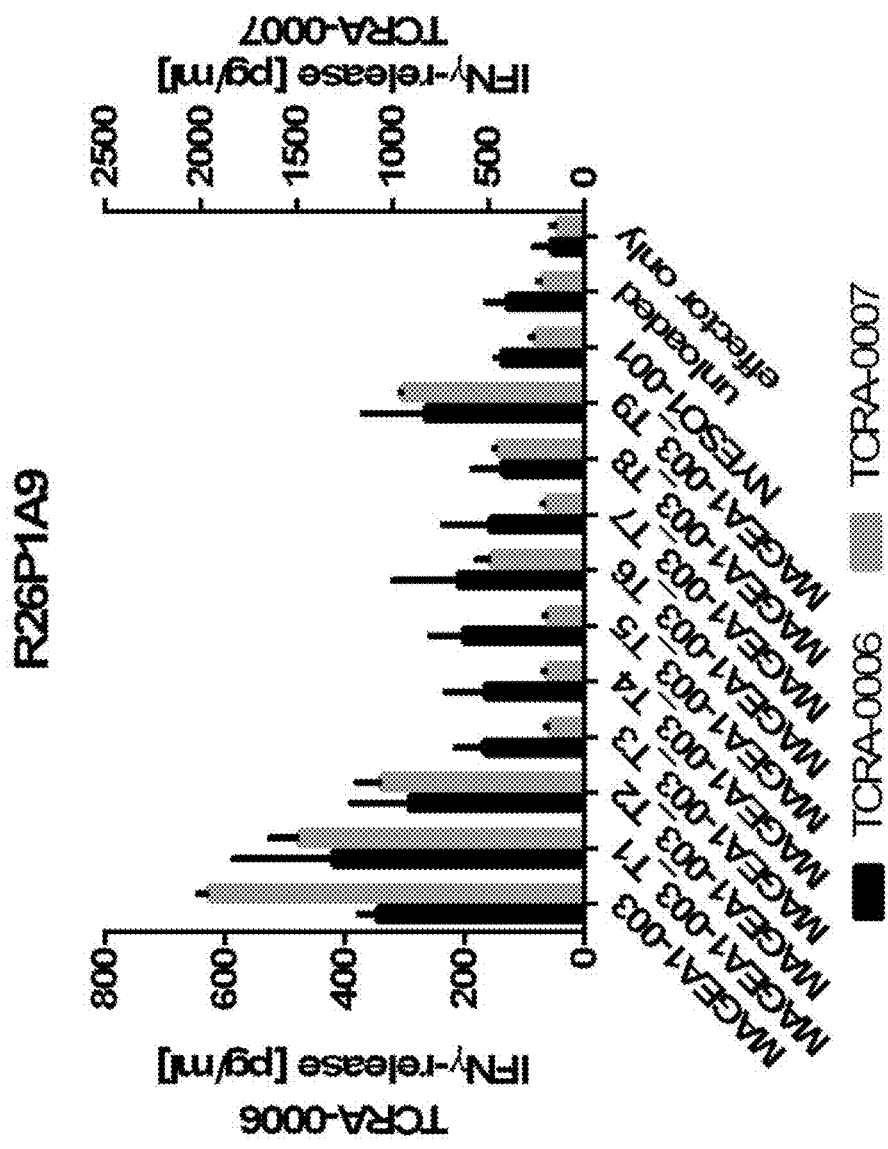

TCR R26P1A9 (SEQ ID NO:1-12) is restricted towards HLA-A*02-presented MAGEA1-003 (SEQ ID NO:133) (see FIG. 11). R26P1A9 specifically recognizes MAGEA1-003 as human primary CD8+ T-cells re-expressing this TCR release IFNγ upon co-incubation with HLA-A*02+ target cells loaded either with MAGEA1-003 peptide or alanine and threonine substitution variants of MAGEA1-003 (FIGS. 1 and 22). TCR R26P1A9 does specifically recognize MAGEA1-003, but not different peptides showing high degree of sequence similarity to MAGEA1-003 (FIG. 11). NYESO1-001 peptide is used as negative control. TCR R26P1A9 has an EC50 of 6 nM (FIG. 36).

Example 2: T-Cell Receptor R26P2A6

Figure 2:
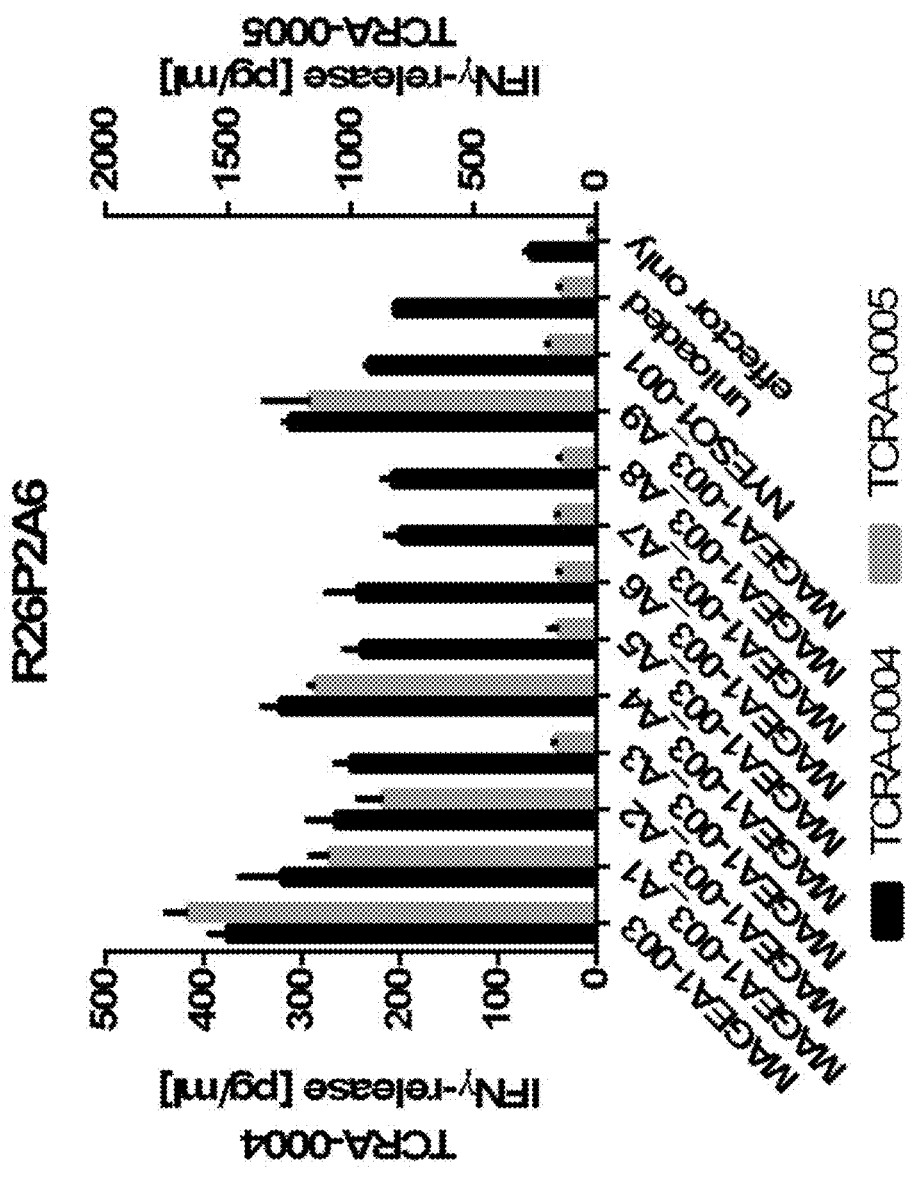
Figure 12:
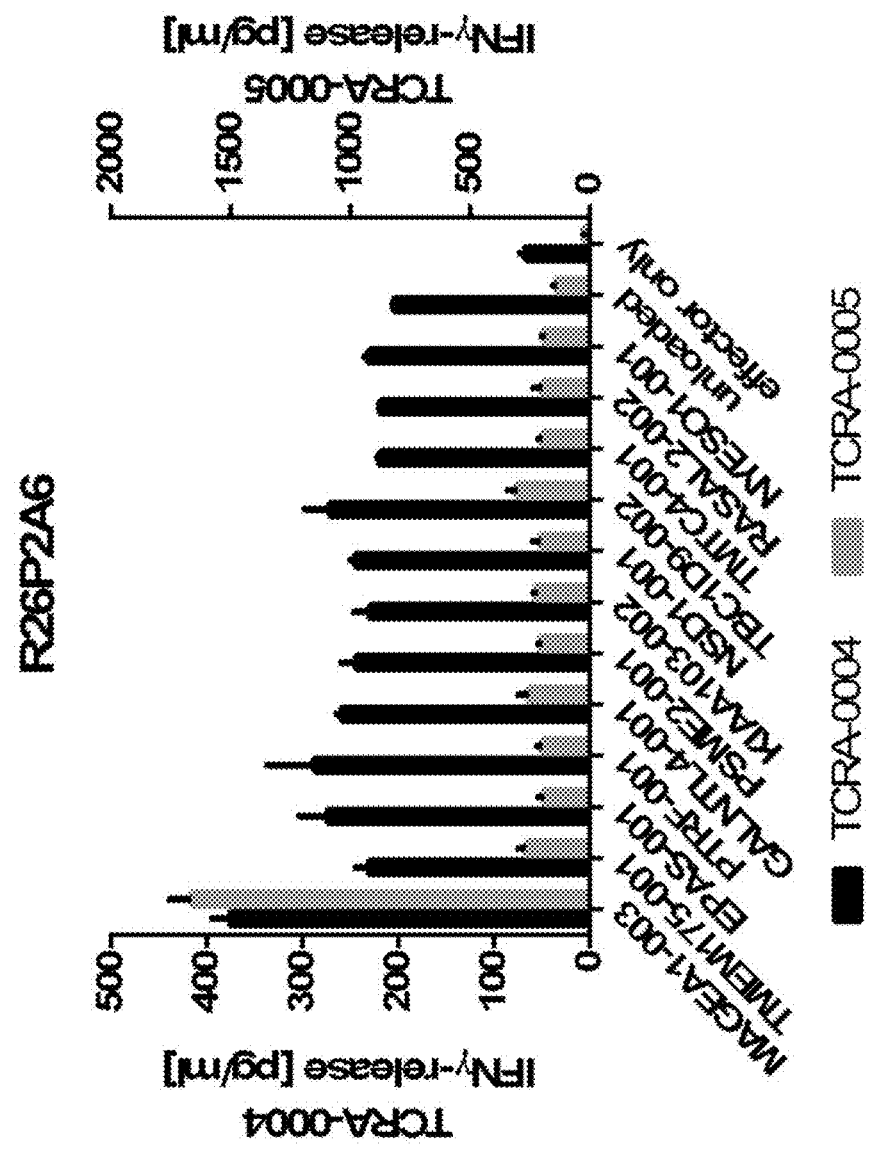
Figure 23:
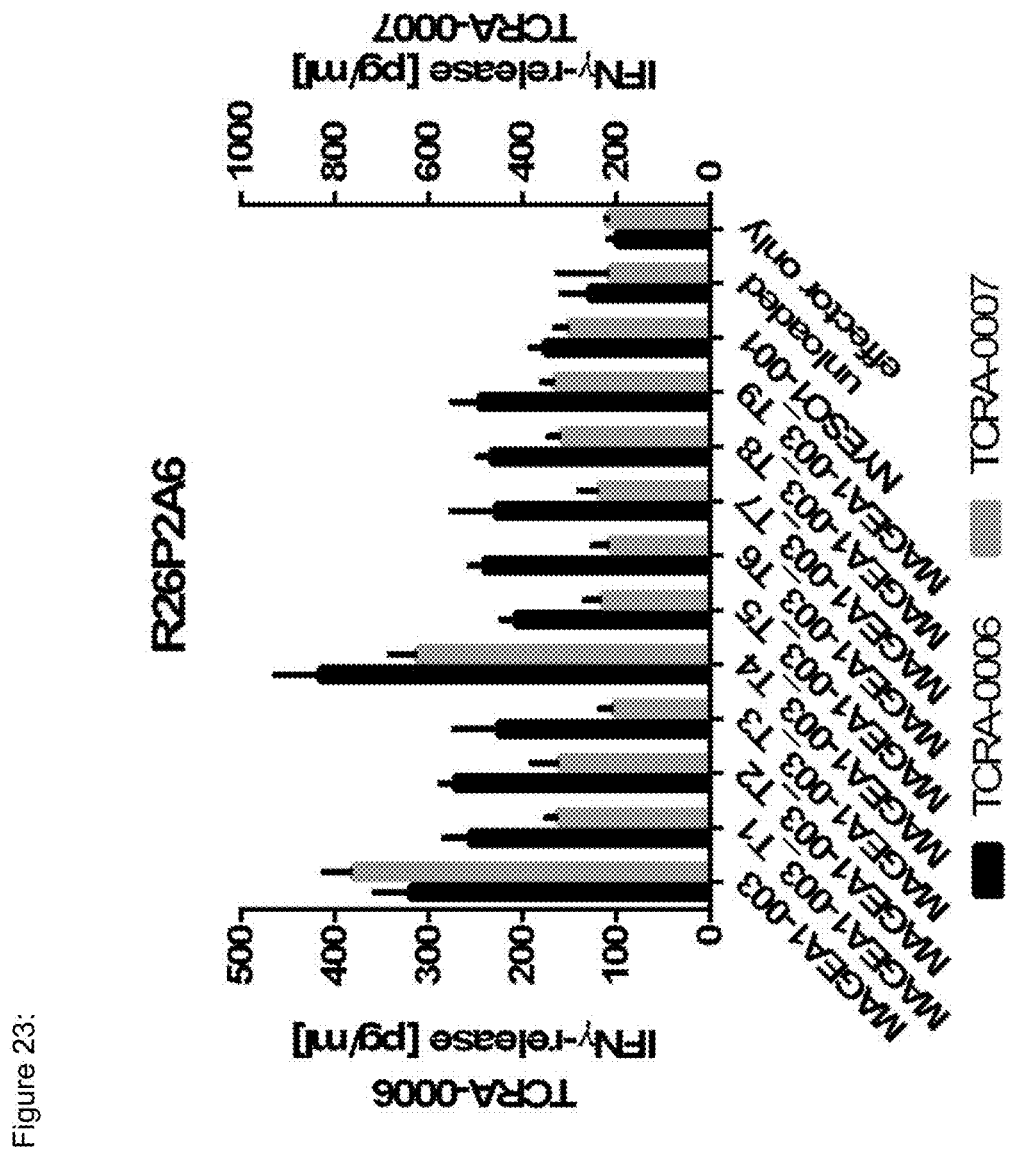

TCR R26P2A6 (SEQ ID NO:13-24) is restricted towards HLA-A*02-presented MAGEA1-003 (SEQ ID NO:133) (see FIG. 12). R26P2A6 specifically recognizes MAGEA1-003 as human primary CD8+ T-cells re-expressing this TCR release IFNγ upon co-incubation with HLA-A*02+ target cells loaded either with MAGEA1-003 peptide or alanine and threonine substitution variants of MAGEA1-003 (FIGS. 2 and 23). TCR R26P2A6 does specifically recognize MAGEA1-003, but not different peptides showing high degree of sequence similarity to MAGEA1-003 (FIG. 12). NYESO1-001 peptide is used as negative control. TCR R26P2A9 has an EC50 of 100 nM (FIG. 37).

Example 3: T-Cell Receptor R26P3H1

Figure 3:
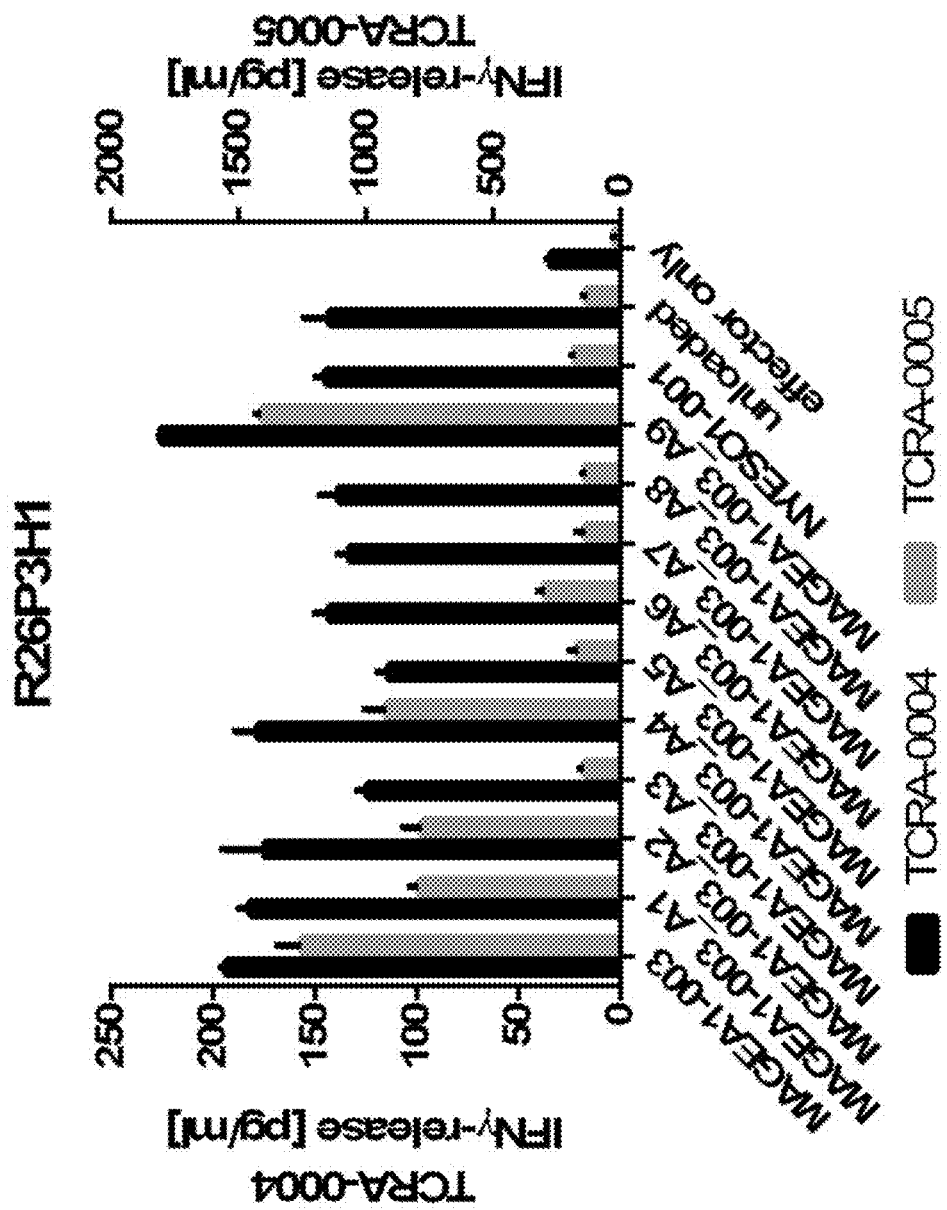
Figure 13:
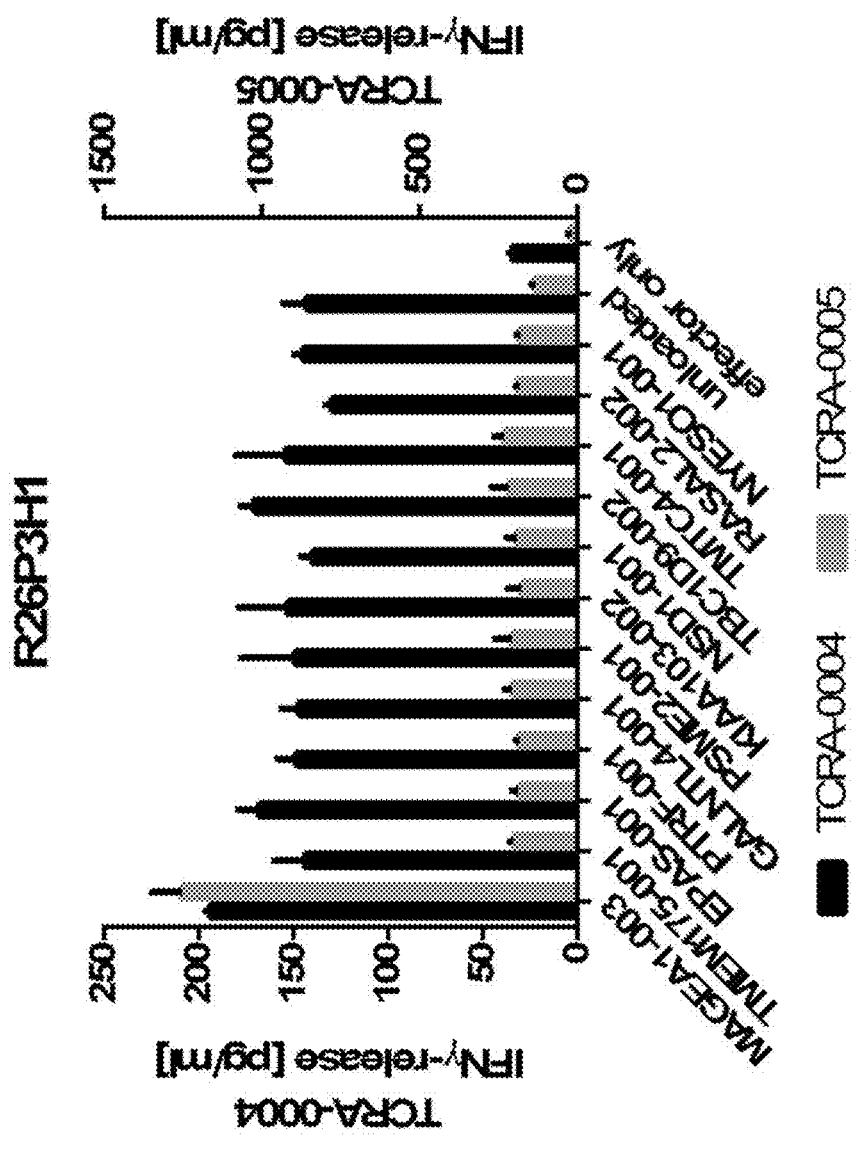
Figure 24:
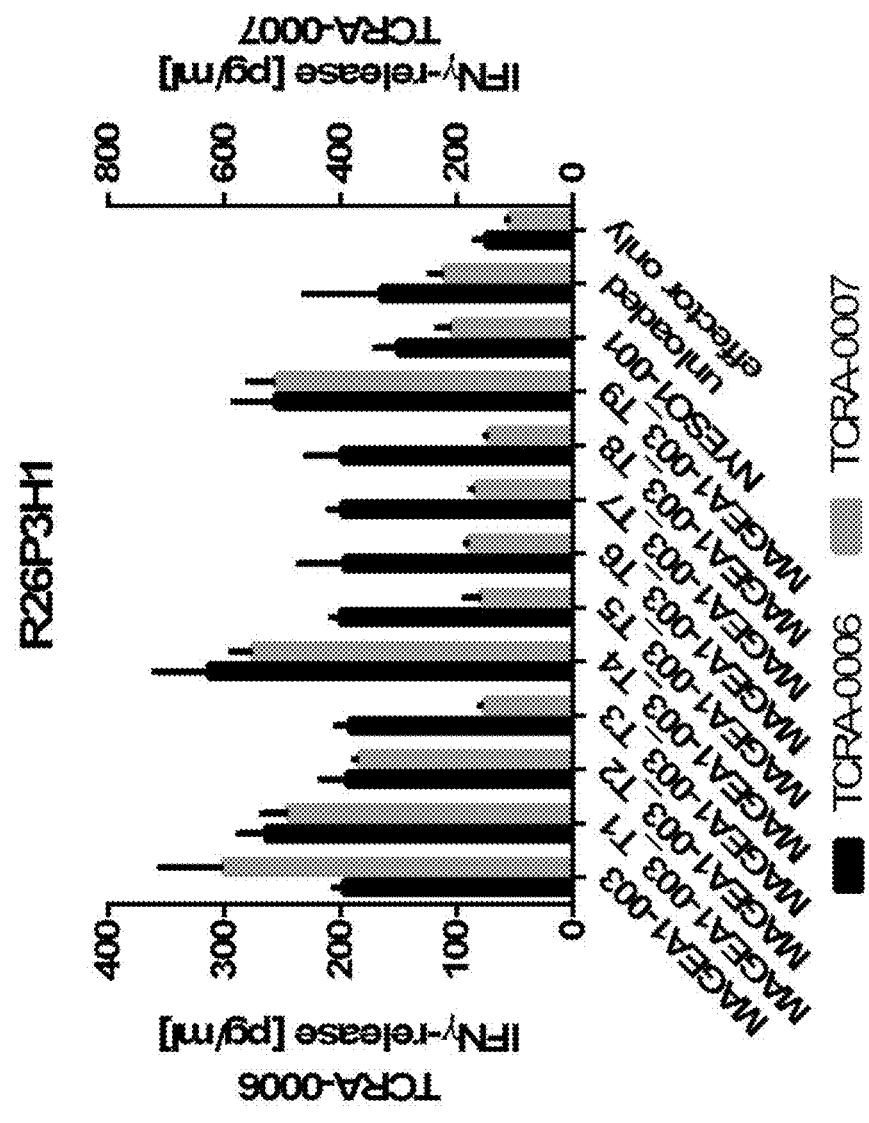

TCR R26P3H1 (SEQ ID NO:25-36) is restricted towards HLA-A*02-presented MAGEA1-003 (SEQ ID NO:133) (see FIG. 13). R26P3H1 specifically recognizes MAGEA1-003 as human primary CD8+ T-cells re-expressing this TCR release IFNγ upon co-incubation with HLA-A*02+ target cells loaded either with MAGEA1-003 peptide or alanine and threonine substitution variants of MAGEA1-003 (FIGS. 3 and 24). This TCR does specifically recognize MAGEA1-003, but not different peptides showing high degree of sequence similarity to MAGEA1-003 (FIG. 13). NYESO1-001 peptide is used as negative control. The TCR has an EC50 of 16 nM.

Example 4: T-Cell Receptor R35P3A4

Figure 4:
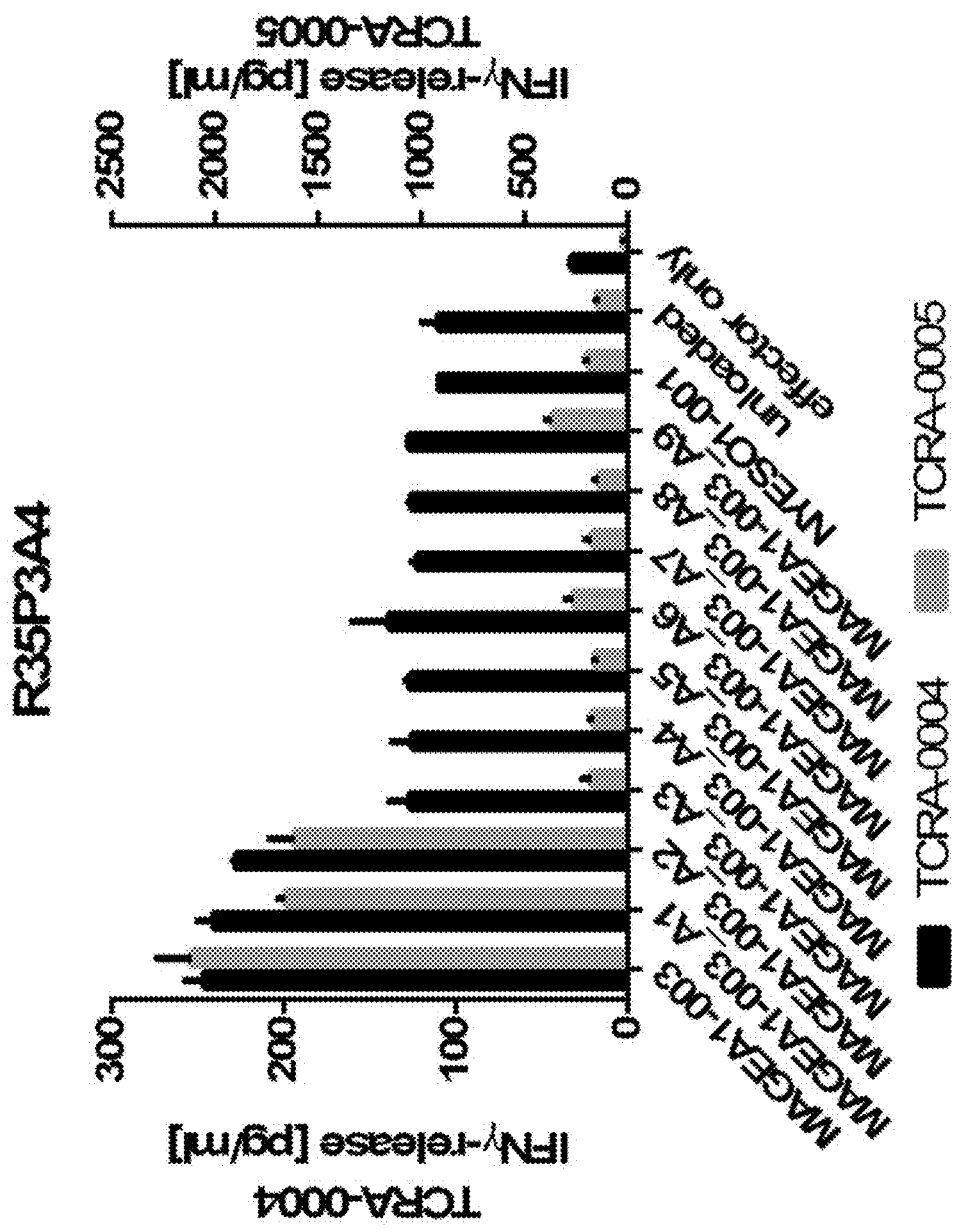
Figure 14:
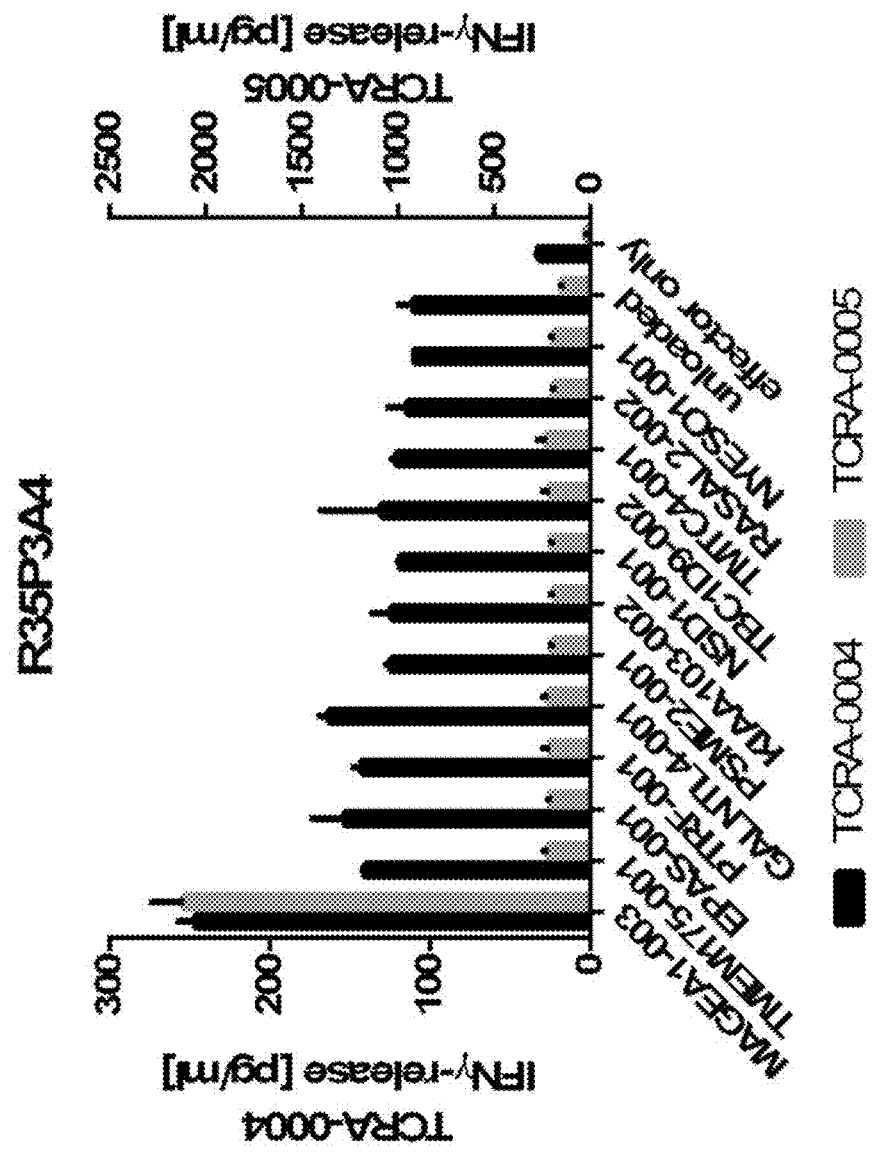
Figure 25:
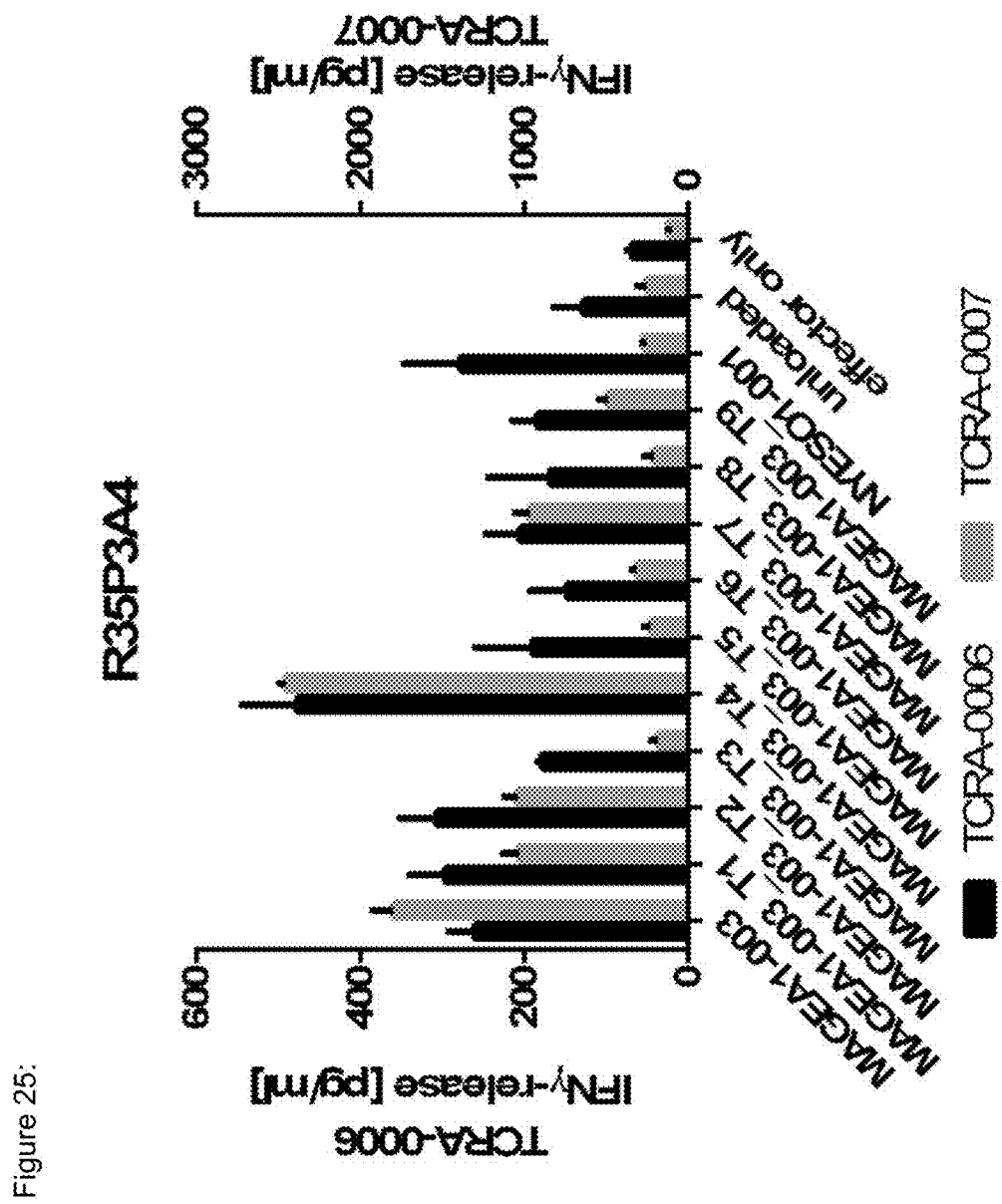

TCR R35P3A4 (SEQ ID NO:37-48) is restricted towards HLA-A*02-presented MAGEA1-003 (SEQ ID NO:133) (see FIG. 14 above). R35P3A4 specifically recognizes MAGEA1-003 as human primary CD8+ T-cells re-expressing this TCR release IFNγ upon co-incubation with HLA-A*02+ target cells and bind HLA-A*02 tetramers, respectively, loaded either with MAGEA1-003 peptide or alanine and threonine substitution variants of MAGEA1-003 (FIGS. 4 and 25). This TCR does specifically recognize MAGEA1-003, but not different peptides showing high degree of sequence similarity to MAGEA1-003 (FIG. 14). NYESO1-001 peptide is used as negative control. The TCR has an EC50 of 16 nM (FIG. 38) and an affinity of 29 µM.

Figure 32:
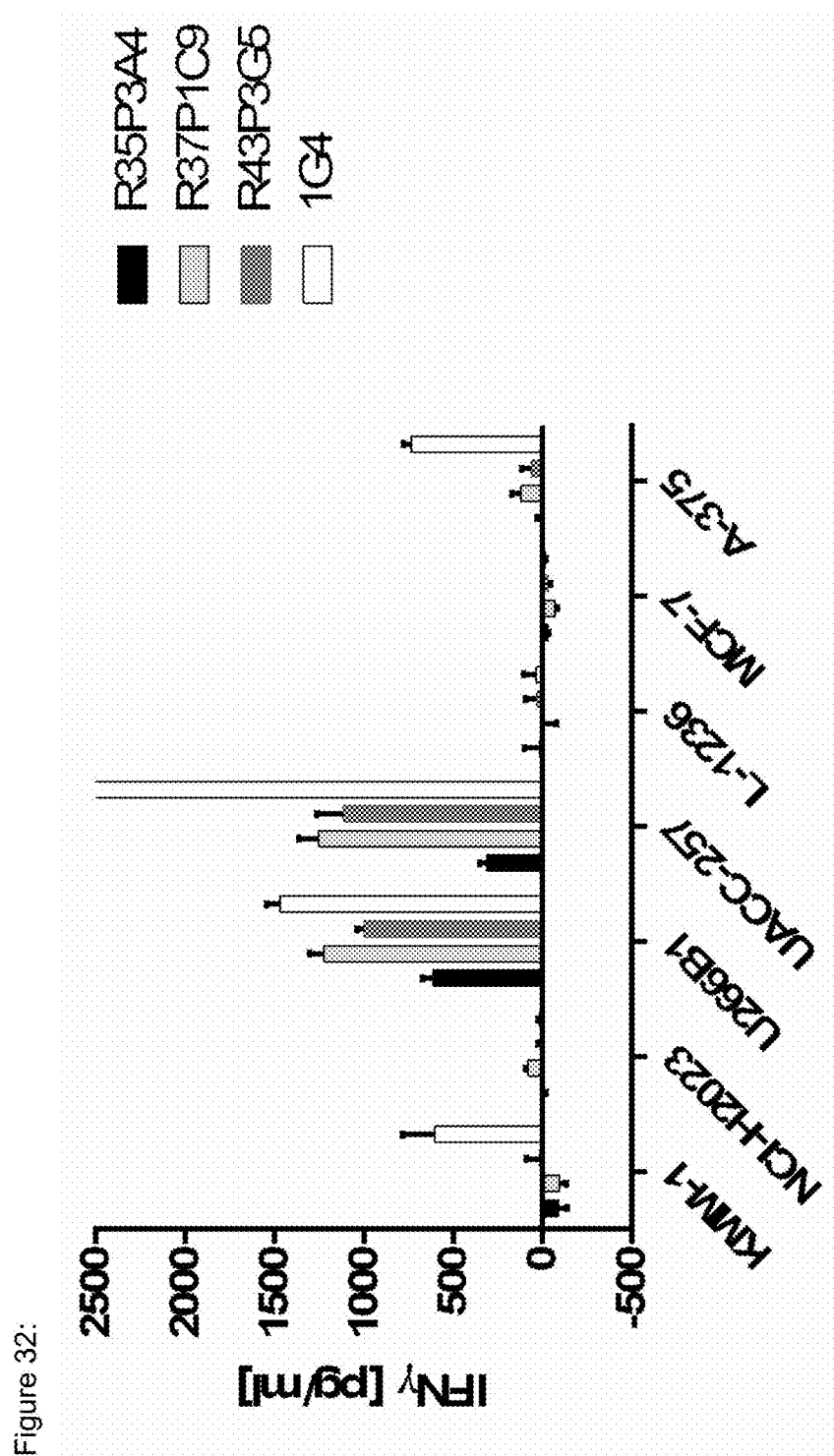

For CD8+ T cells expressing TCR R35P3A4, no activation was observed upon co-culture with HLA-A*02 positive cell types from healthy tissues (see FIG. 33), while there was an activity towards the tumor cell lines UACC-257 and U266B1 expressing HLA-A*02 and MAGEA1 as source gene for MAGEA1-003 peptide (FIGS. 32 and 33). A corresponding pattern of reactivity was observed with CD8+ T cells expressing the NYESO1-specific control TCR 1G4, with reactivity towards NYESO1 expressing HLA-A*02 positive tumor cell lines but not towards the indicated panel of healthy tissue cells.

T-cell activation upon co-culture with cell lines expressing HLA-A*02 and MAGEA1 reflects the recognition of endogenously expressed and presented target pHLA (peptide presented on human leukocyte antigen) by TCRs R35P3A4.

Example 5: T-Cell Receptor R37P1C9

Figure 5:
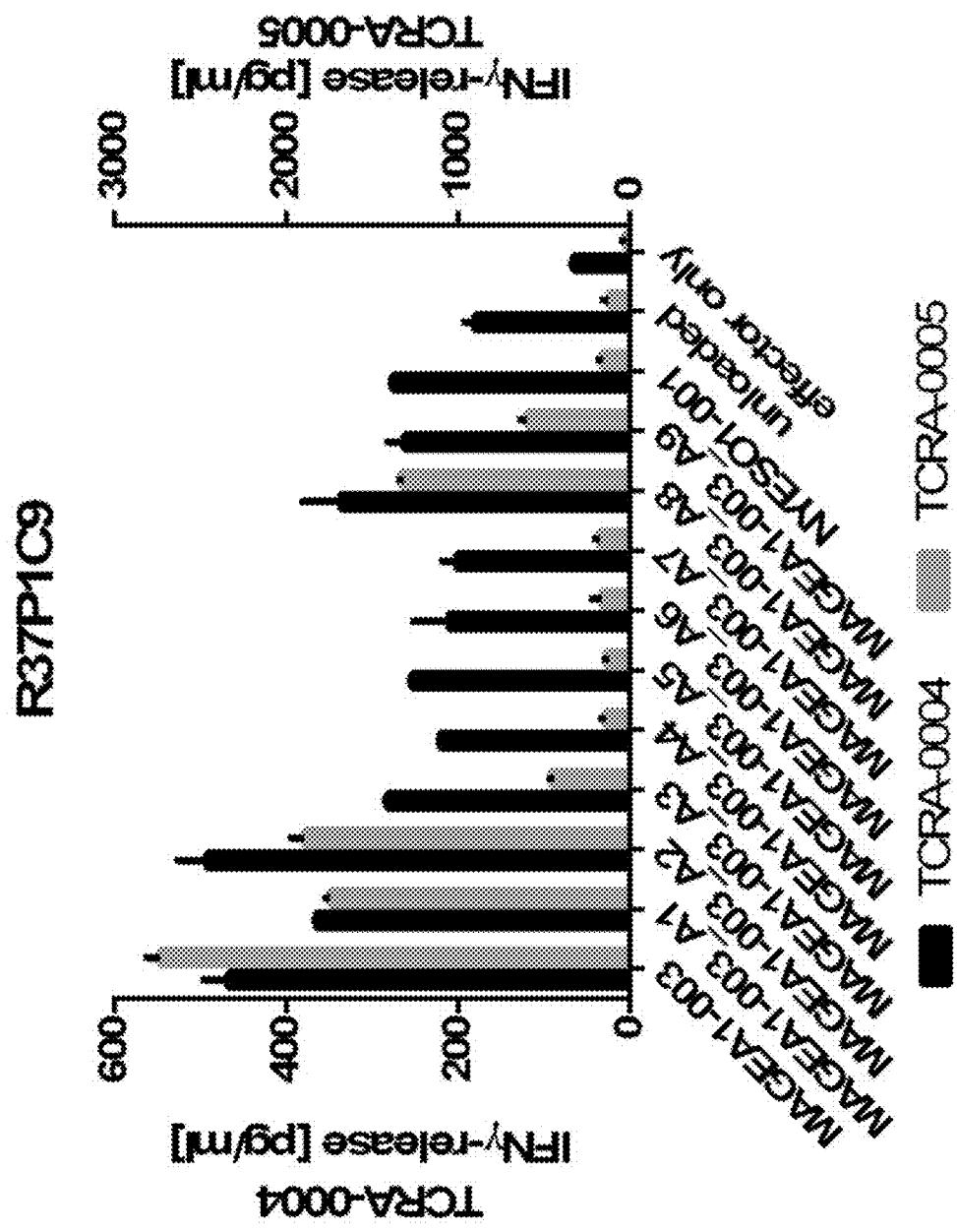
Figure 15:
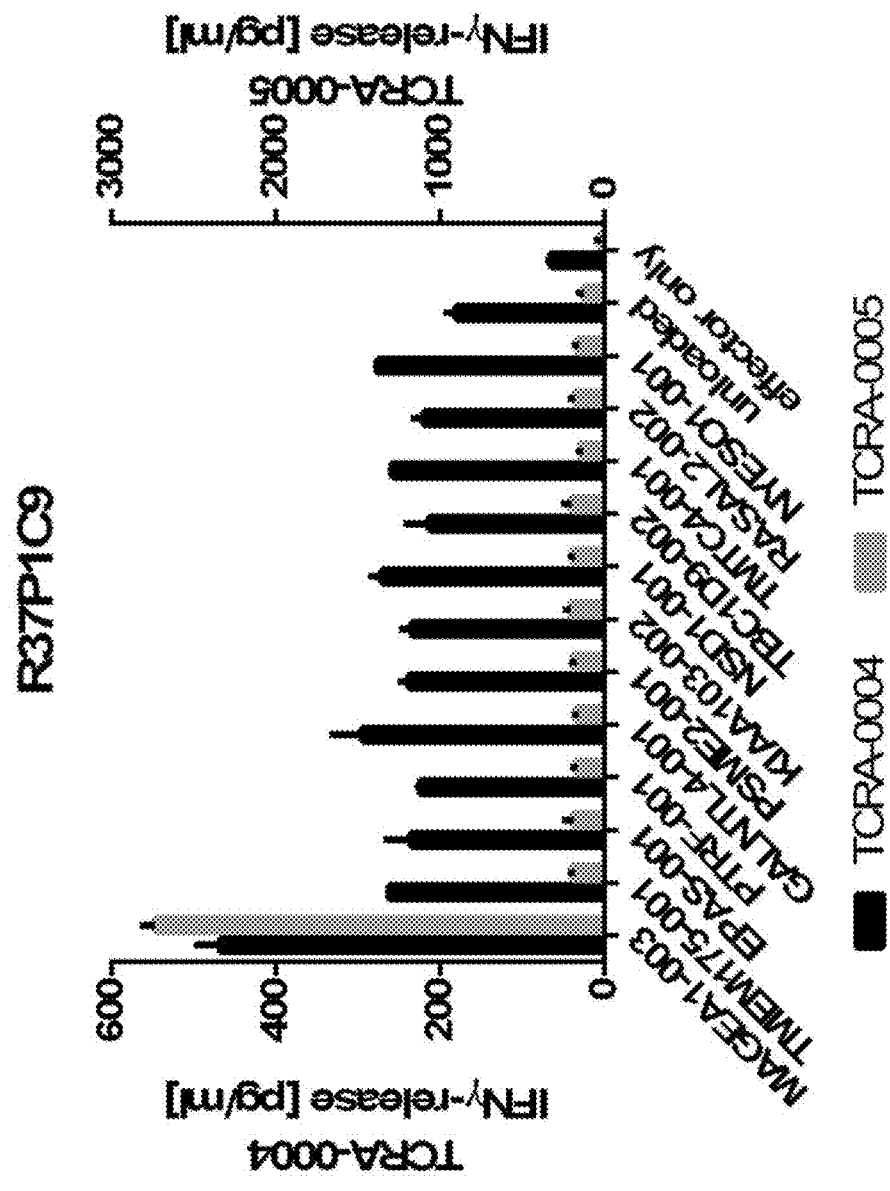
Figure 26:
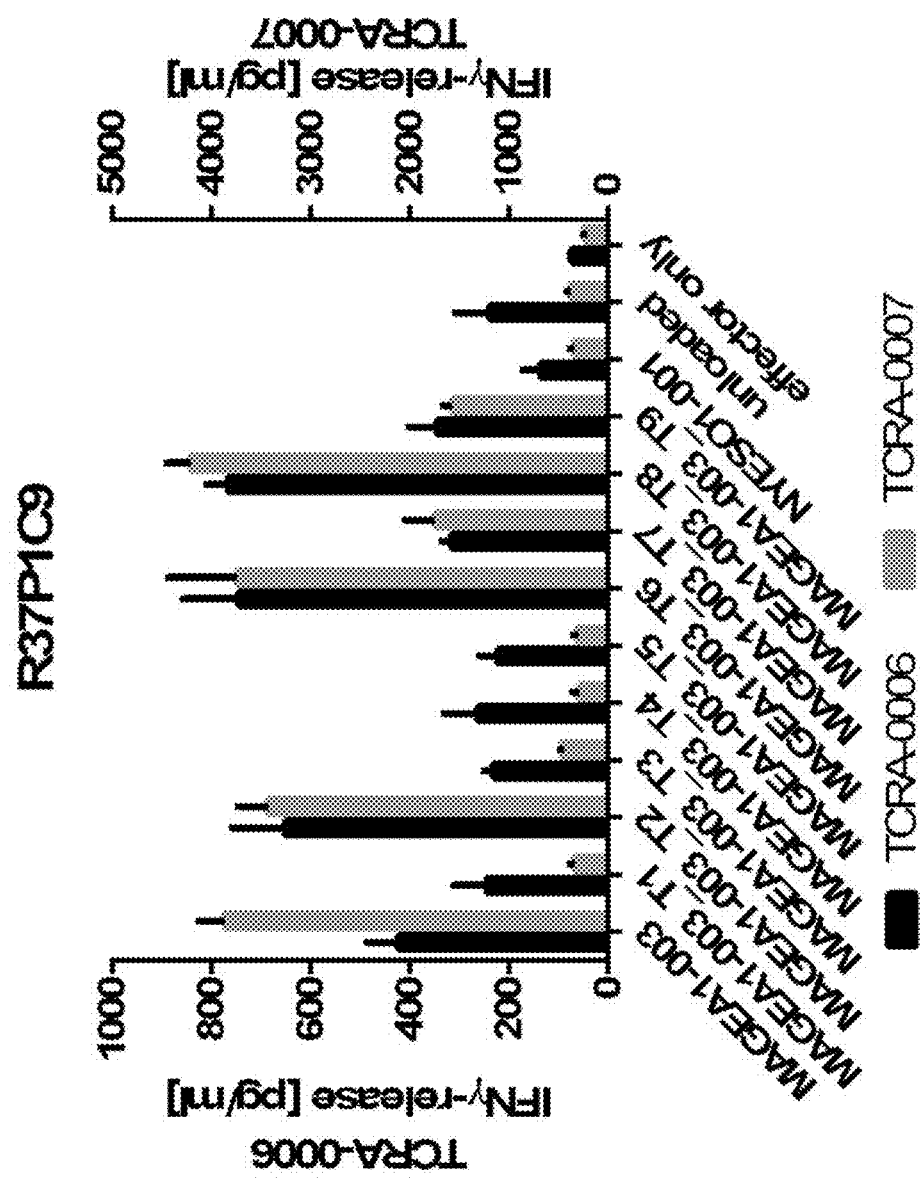

TCR R37P1C9 (SEQ ID NO:49-60) is restricted towards HLA-A*02-presented MAGEA1-003 (SEQ ID NO:133) (see FIG. 15). R37P1C9 specifically recognizes MAGEA1-003 as human primary CD8+ T-cells re-expressing this TCR release IFNγ upon co-incubation with HLA-A*02+ target cells loaded either with MAGEA1-003 peptide or alanine and threonine substitution variants of MAGEA1-003 (FIGS. 5 and 26). This TCR does specifically recognize MAGEA1-003, but not different peptides showing high degree of sequence similarity to MAGEA1-003 (FIG. 15). NYESO1-001 peptide is used as negative control. The TCR has an EC50 of 13 nM (FIGS. 34B and 39) and an affinity of 8.7 µM.

Figure 21:
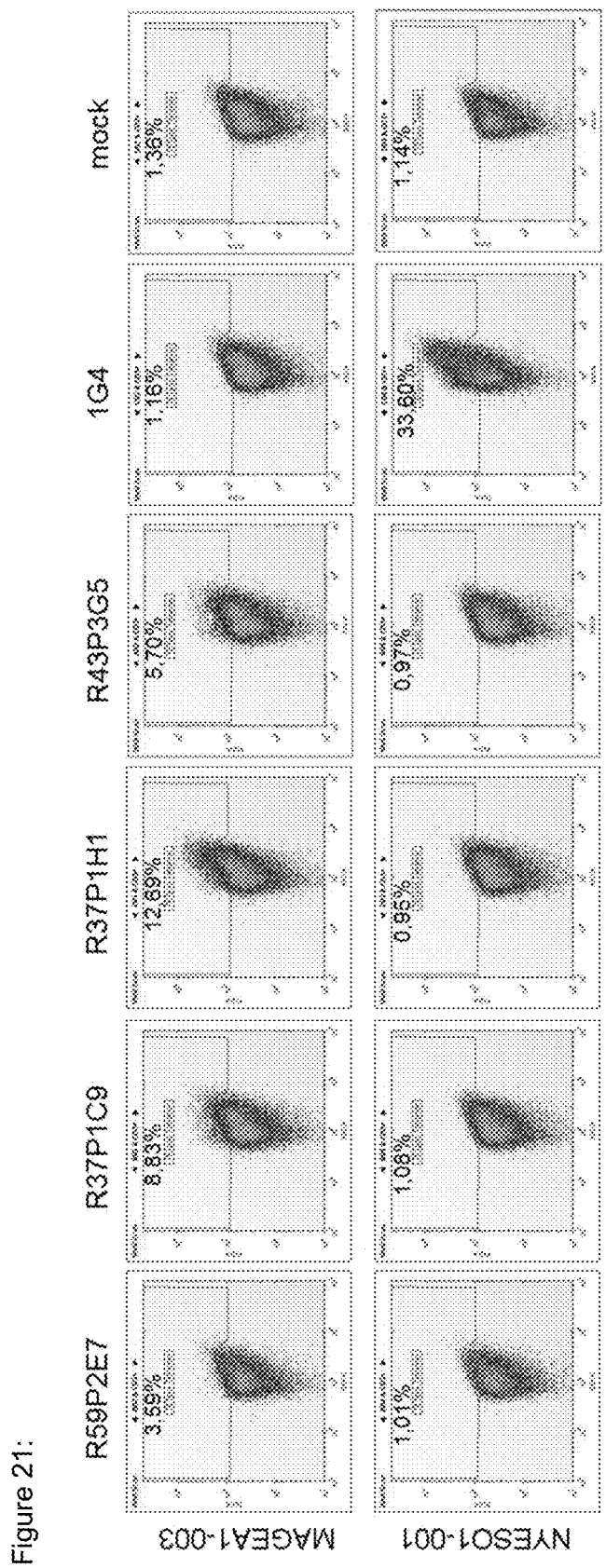

Re-expression of R37P1C9 in human primary CD8+ T-cells leads to selective binding of HLA-A*02/MAGEA1-003 tetramers but not HLA-A*02/NYESO1-001 tetramers (FIG. 21). Re-expression of the NYESO1-001-specific TCR 1G4 and mock expression are used as control.

For CD8+ T cells expressing TCR R37P1C9, no activation was observed upon co-culture with HLA-A*02 positive cell types from healthy tissues (see FIG. 33), while there was an activity towards the tumor cell lines UACC-257 and U266B1 expressing HLA-A*02 and MAGEA1 as source gene for MAGEA1-003 peptide (FIGS. 32 and 33). A corresponding pattern of reactivity was observed with CD8+ T cells expressing the NYESO1-specific control TCR 1G4, with reactivity towards NYESO1 expressing HLA-A*02 positive tumor cell lines but not towards the indicated panel of healthy tissue cells.

T-cell activation upon co-culture with cell lines expressing HLA-A*02 and MAGEA1 reflects the recognition of endogenously expressed and presented target pHLA by TCRs R37P1C9, independently from the gene delivery method e.g. mRNA electroporation, lentiviral transduction, etc. (FIGS. 32 and 34).

Example 6: T-Cell Receptor R37P1H1

Figure 6:
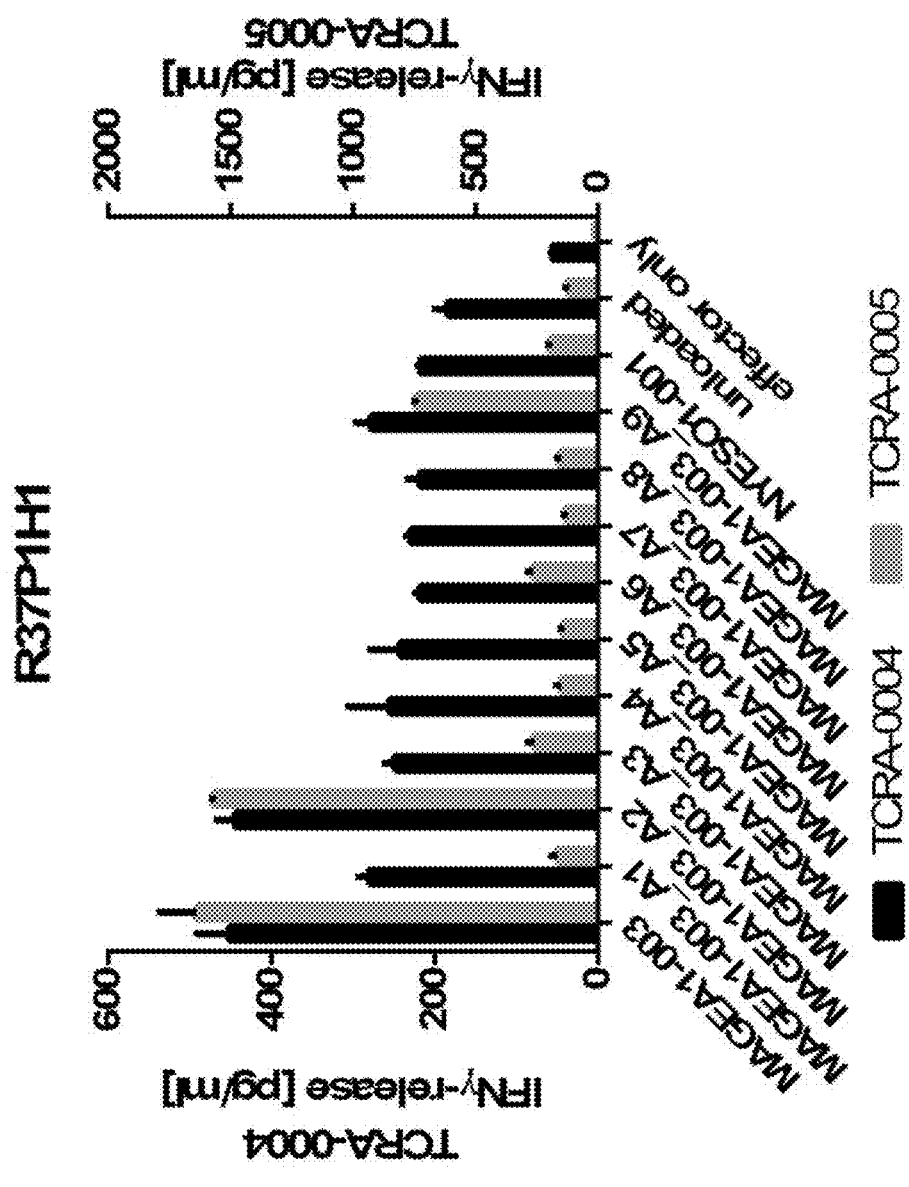
Figure 16:
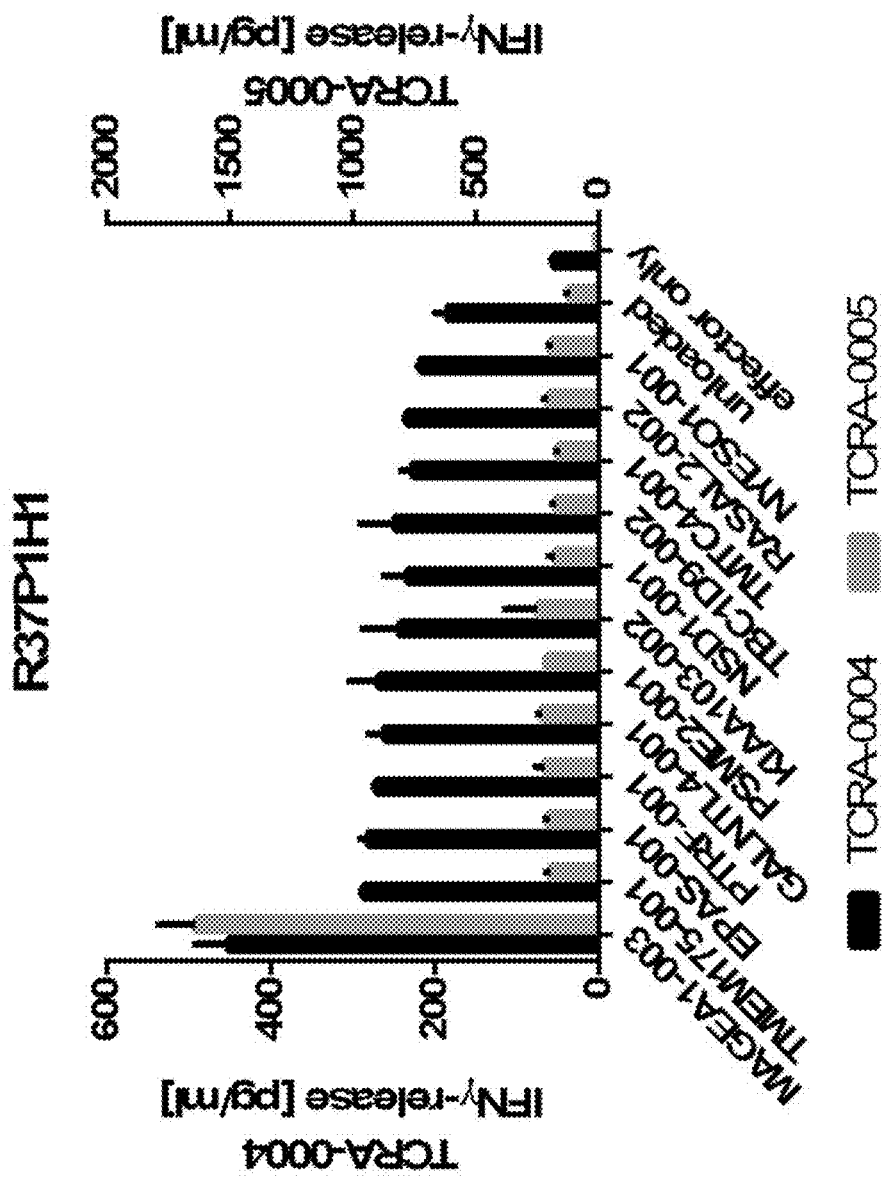
Figure 27:
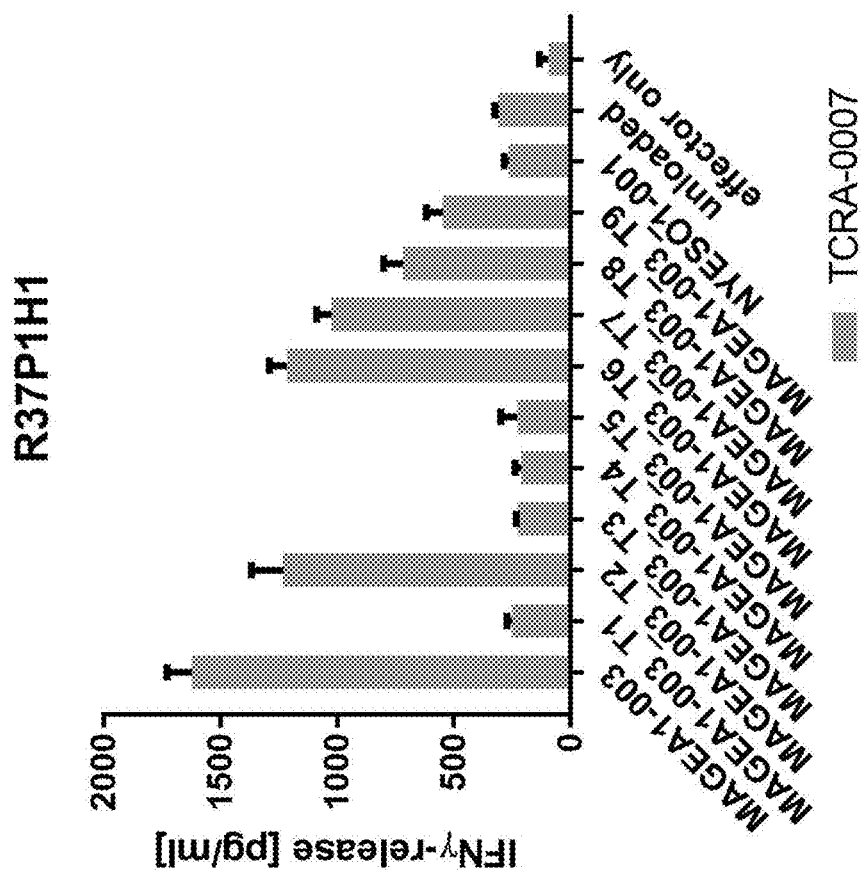

TCR R37P1H1 (SEQ ID NO: 61-72) is restricted towards HLA-A*02-presented MAGEA1-003 (SEQ ID NO: 133) (see FIG. 16). R37P1H1 specifically recognizes MAGEA1-003 as human primary CD8+ T-cells re-expressing this TCR release IFNγ upon co-incubation with HLA-A*02+ target cells loaded either with MAGEA1-003 peptide or alanine and threonine substitution variants of MAGEA1-003 (FIGS. 6 and 27). This TCR does specifically recognize MAGEA1-003, but not different peptides showing high degree of sequence similarity to MAGEA1-003 (FIG. 16). NYESO1-001 peptide is used as negative control. The TCR has an EC50 of 26 nM (FIG. 40).

Re-expression of R37P1H1 in human primary CD8+ T-cells leads to selective binding of HLA-A*02/MAGEA1-003 tetramers but not HLA-A*02/NYESO1-001 tetramers (FIG. 21). Re-expression of the NYESO1-001-specific TCR 1G4 and mock expression are used as control.

Example 7: T-Cell Receptor R42P3A9

Figure 7:
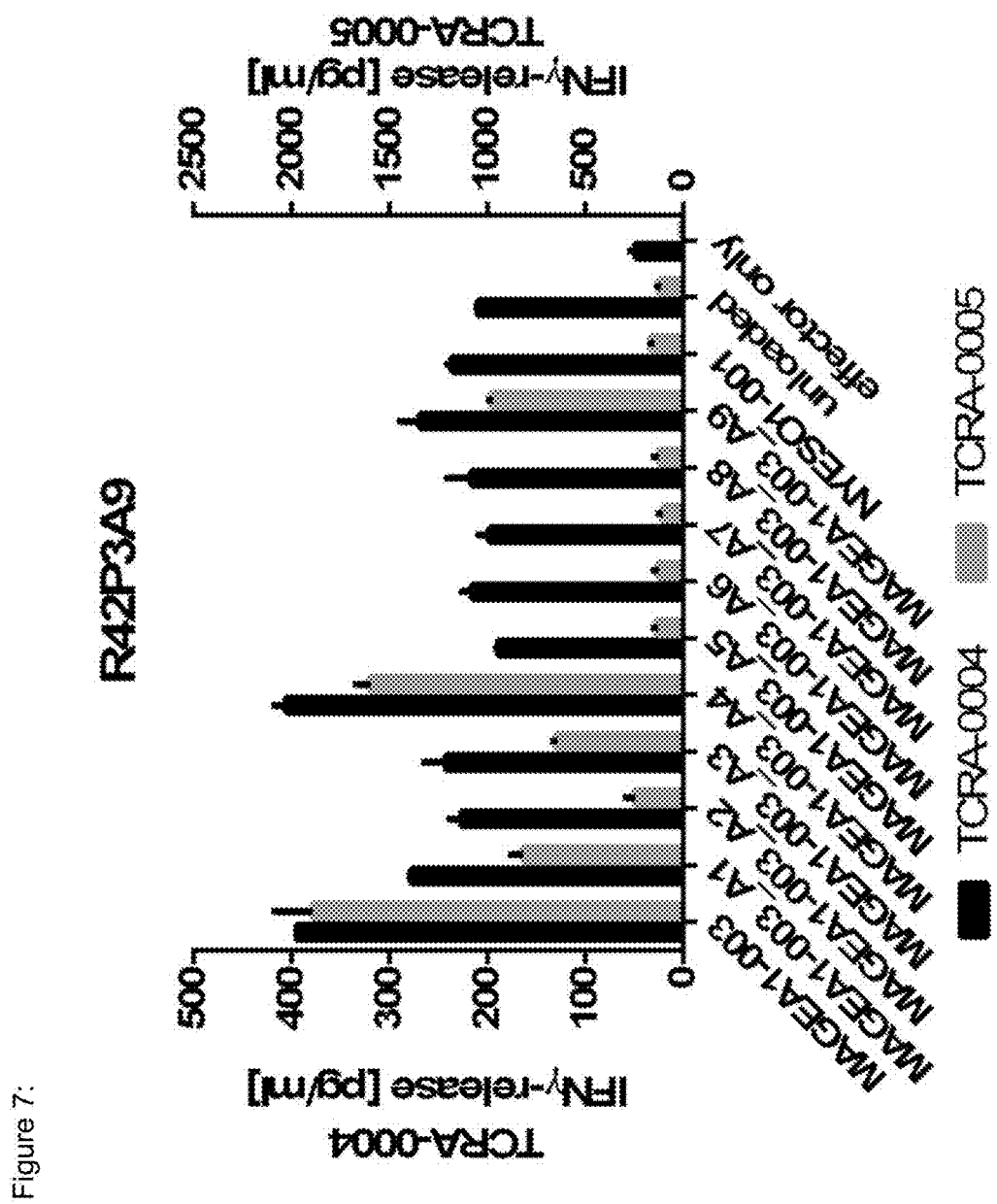
Figure 17:
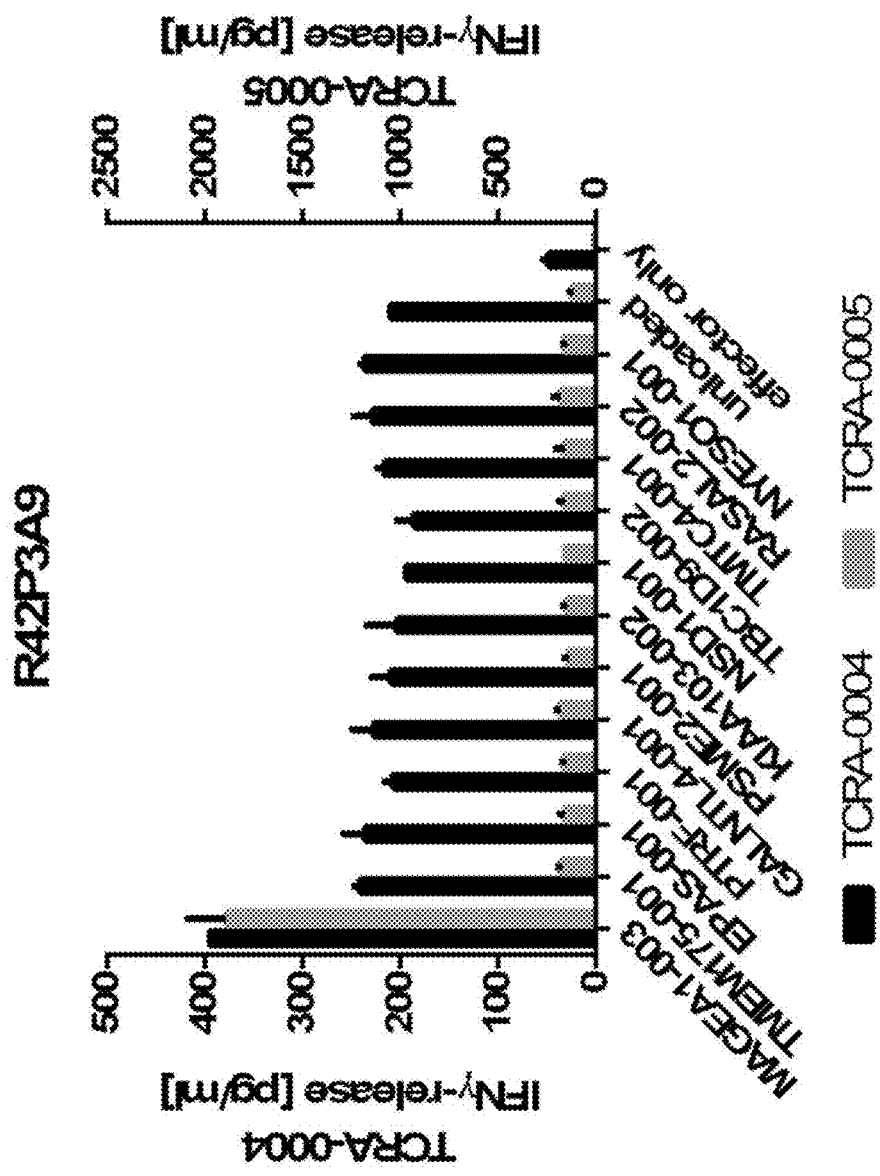
Figure 28:
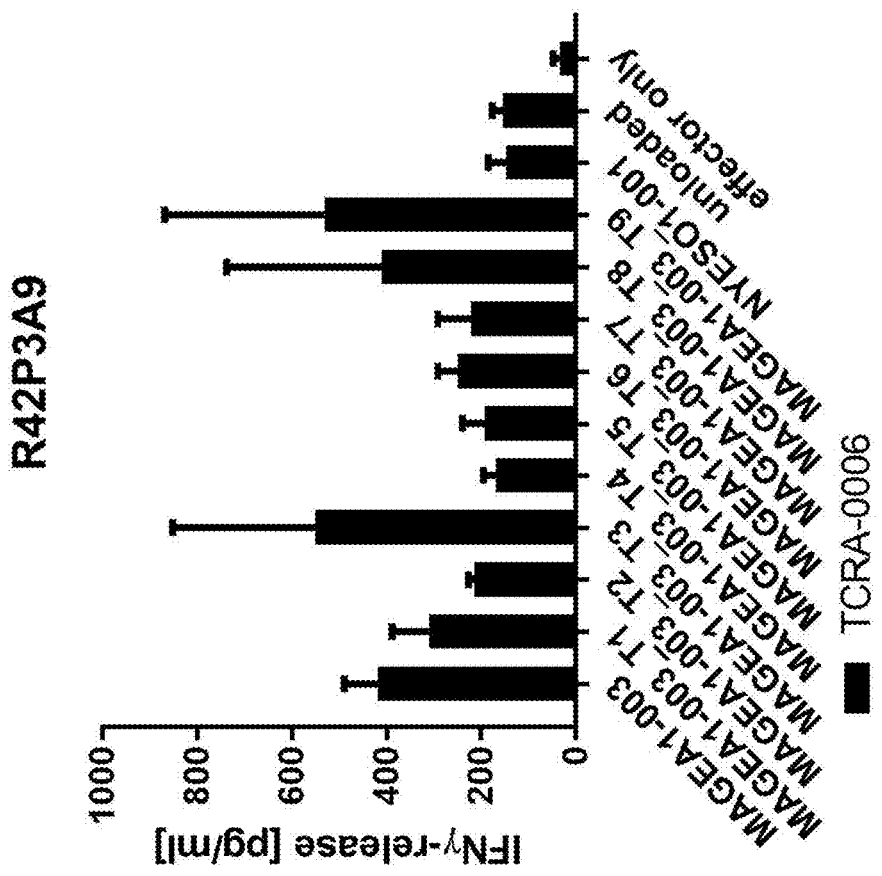

TCR R42P3A9 (SEQ ID NO: 73-84) is restricted towards HLA-A*02-presented MAGEA1-003 (SEQ ID NO: 133) (see FIG. 17). R42P3A9 specifically recognizes MAGEA1-003 as human primary CD8+ T-cells re-expressing this TCR release IFNγ upon co-incubation with HLA-A*02+ target cells loaded either with MAGEA1-003 peptide or alanine and threonine substitution variants of MAGEA1-003 (FIGS. 7 and 28). This TCR does specifically recognize MAGEA1-003, but not different peptides showing high degree of sequence similarity to MAGEA1-003 (FIG. 17). NYESO1-001 peptide is used as negative control. The TCR has an EC50 of 823 nM (FIG. 41).

Example 8: T-Cell Receptor R43P3F2

Figure 8:
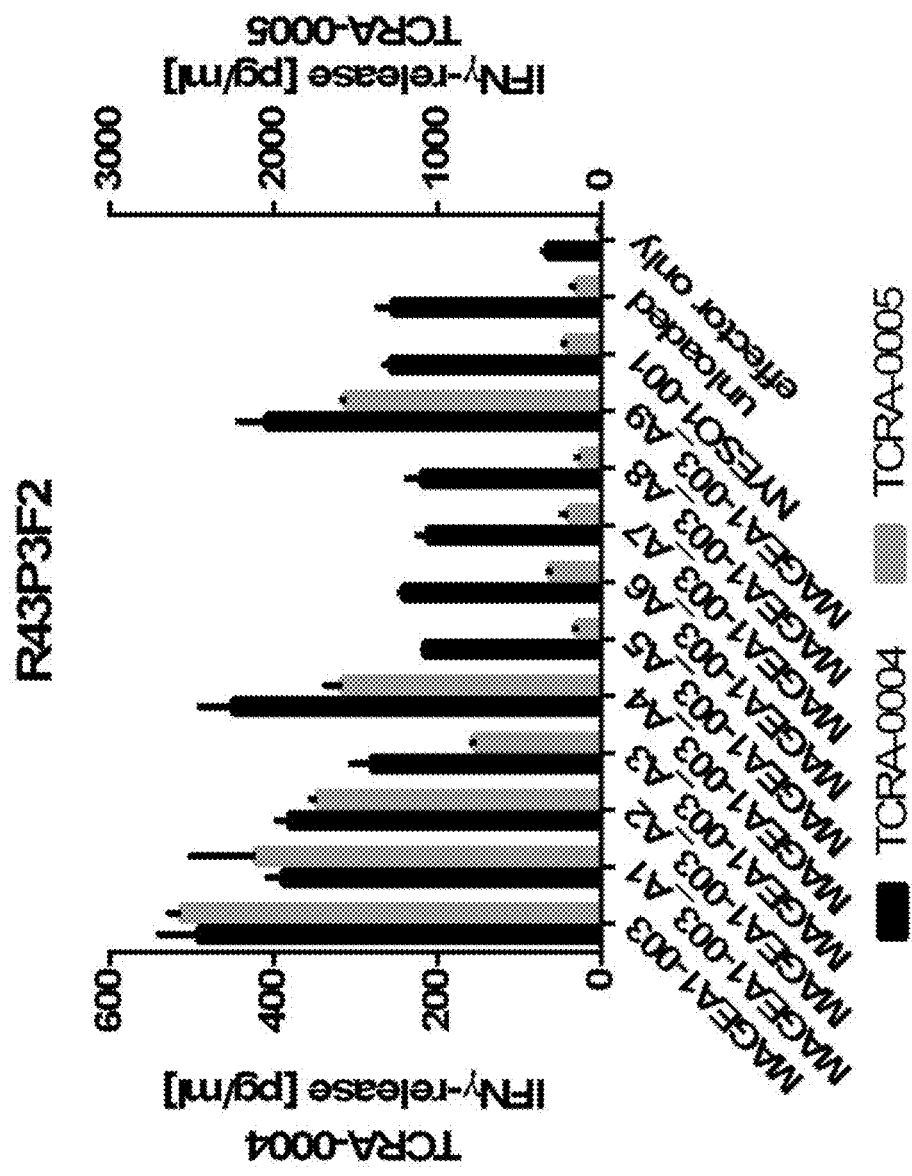
Figure 18:
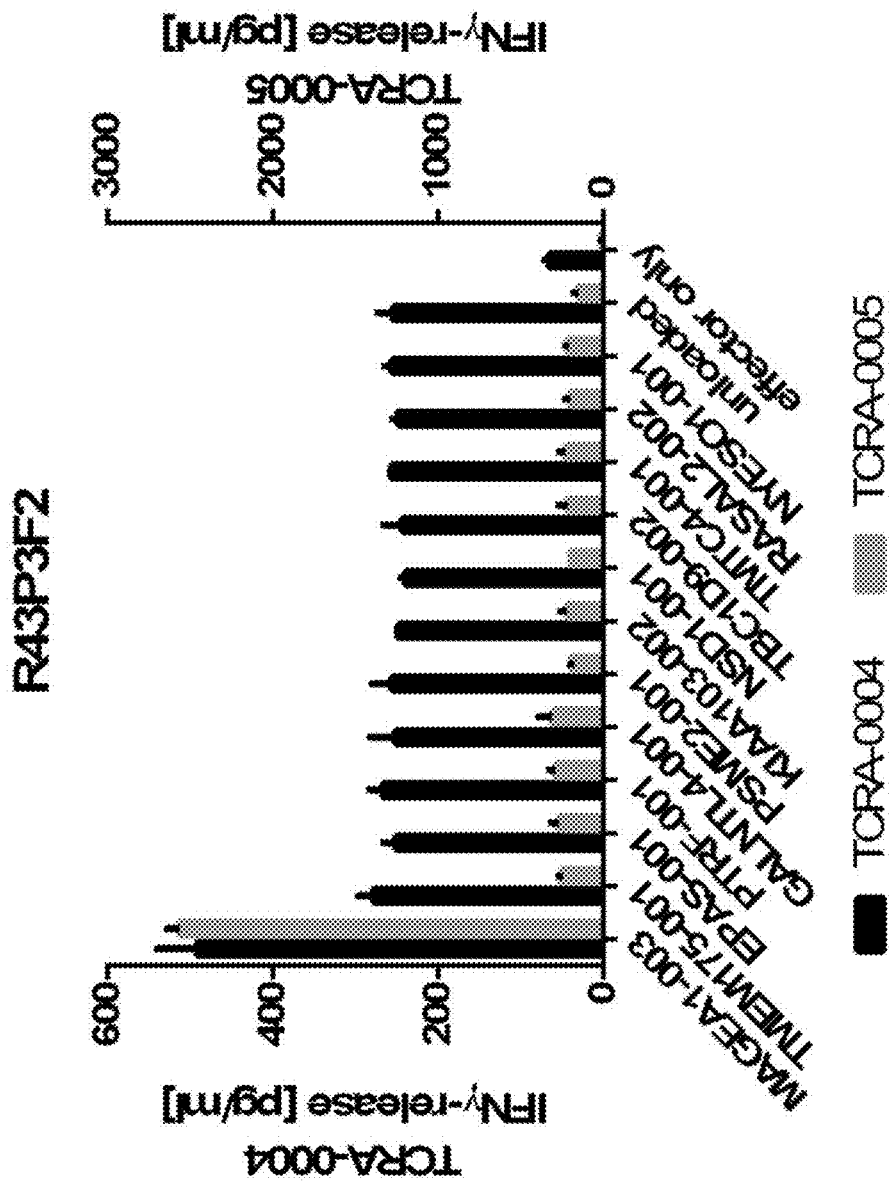
Figure 29:
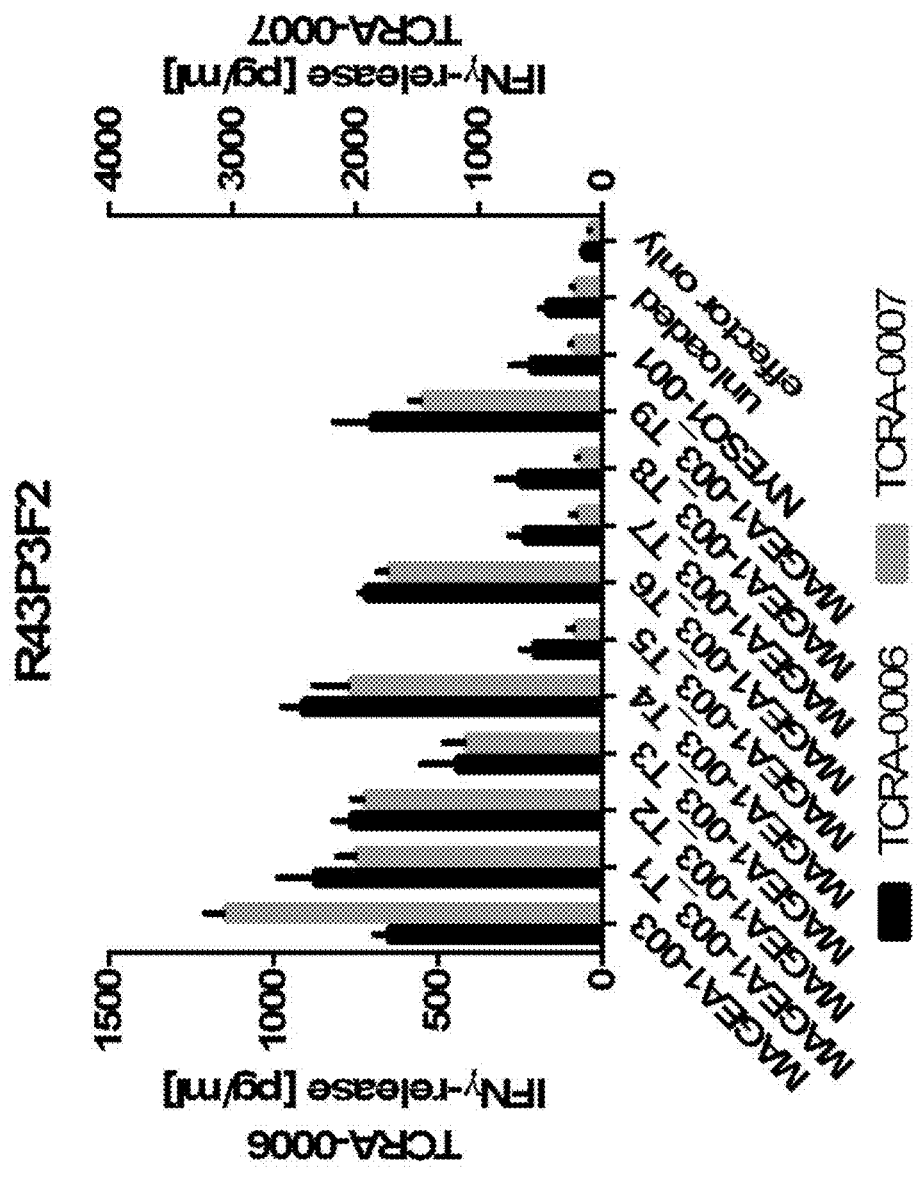

TCR R42P3F2 (SEQ ID NO: 85-96) is restricted towards HLA-A*02-presented MAGEA1-003 (SEQ ID NO: 133) (see FIG. 18). R42P3F2 specifically recognizes MAGEA1-003 as human primary CD8+ T-cells re-expressing this TCR release IFNγ upon co-incubation with HLA-A*02+ target cells loaded either with MAGEA1-003 peptide or alanine and threonine substitution variants of MAGEA1-003 (FIGS. 8 and 29). This TCR does specifically recognize MAGEA1-003, but not different peptides showing high degree of sequence similarity to MAGEA1-003 (FIG. 18). NYESO1-001 peptide is used as negative control. The TCR has an EC50 of 1,7 nM (FIG. 42).

Example 9: T-Cell Receptor R43P3G5

Figure 9:
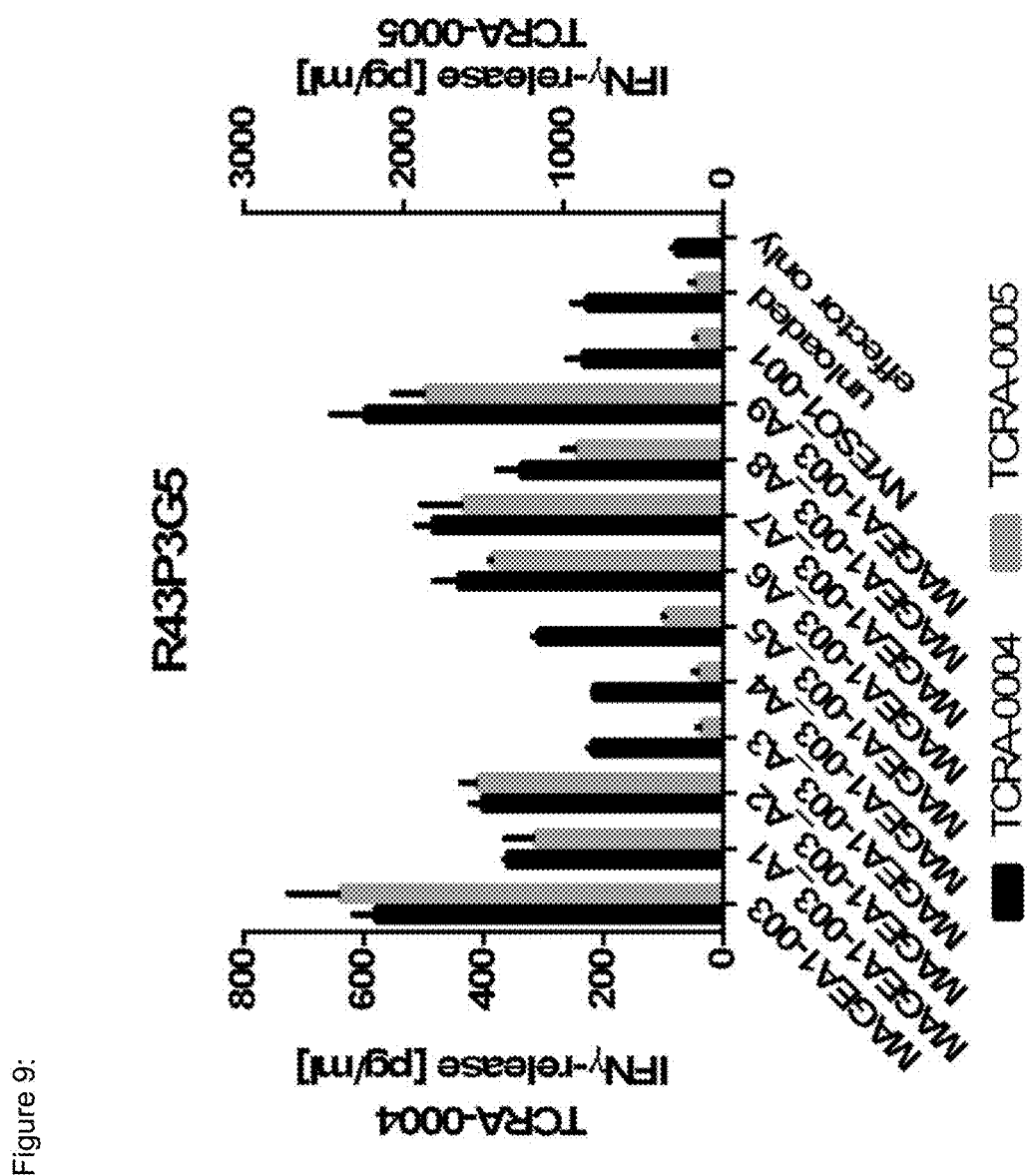
Figure 19:
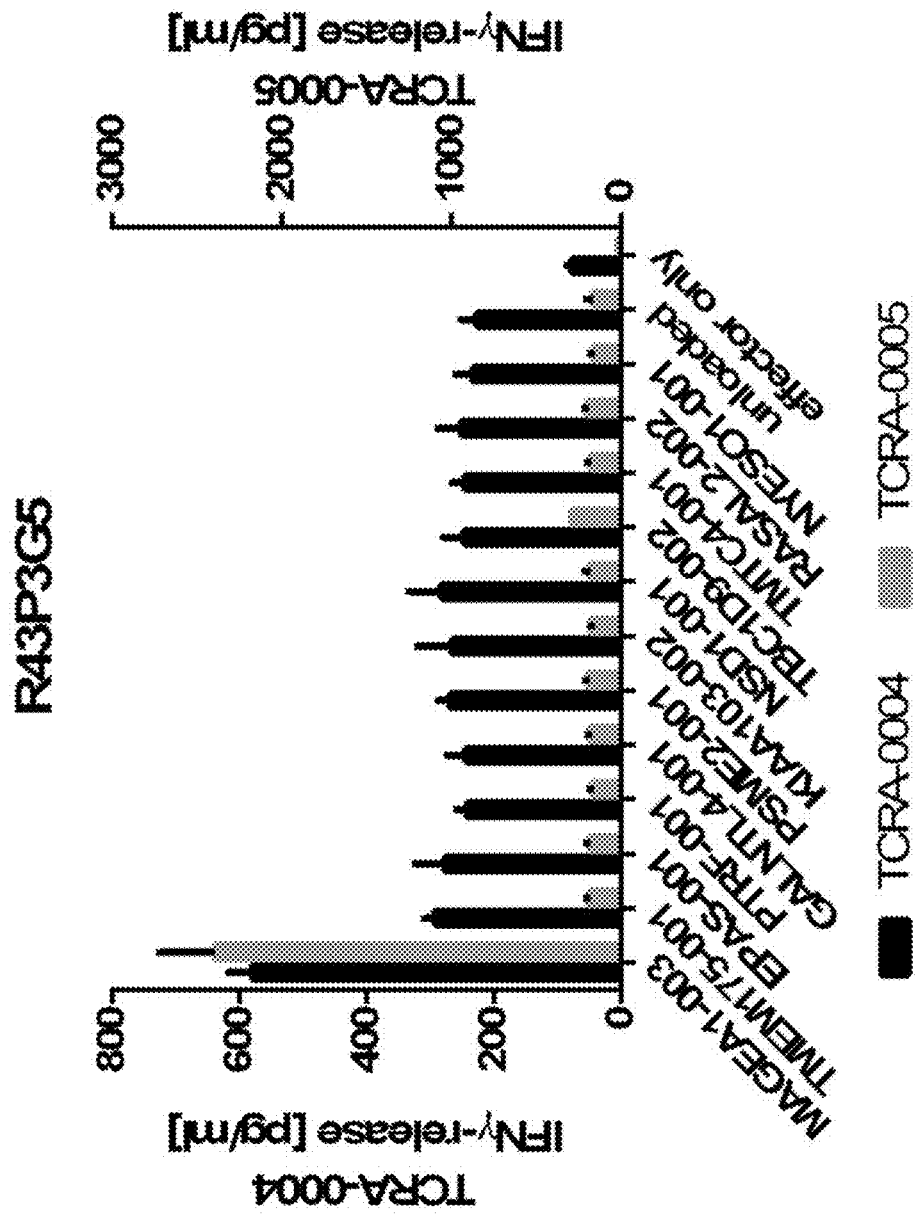
Figure 30:
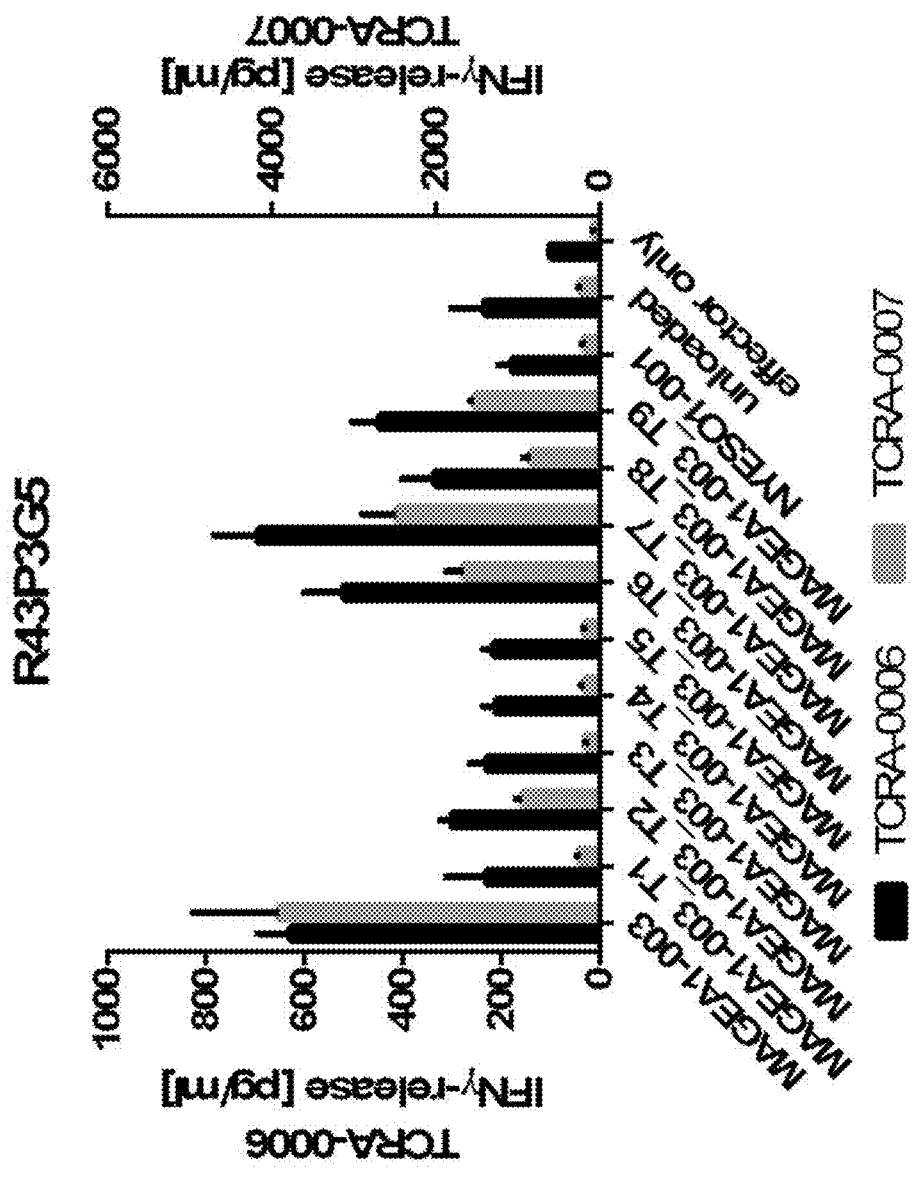

TCR R43P3G5 (SEQ ID NO: 97-108) is restricted towards HLA-A*02-presented MAGEA1-003 (SEQ ID NO: 133) (see FIG. 19). R43P3G5 specifically recognizes MAGEA1-003 as human primary CD8+ T-cells re-expressing this TCR release IFNγ upon co-incubation with HLA-A*02+ target cells loaded either with MAGEA1-003 peptide or alanine and threonine substitution variants of MAGEA1-003 (FIGS. 9 and 30). This TCR does specifically recognize MAGEA1-003, but not different peptides showing high degree of sequence similarity to MAGEA1-003 (FIG. 19). NYESO1-001 peptide is used as negative control. The TCR has an EC50 of 6,6 nM (FIG. 43) and an affinity of 38 μM.

Re-expression of R43P3G5 in human primary CD8+ T-cells leads to selective binding of HLA-A*02/MAGEA1-003 tetramers but not HLA-A*02/NYESO1-001 tetramers (FIG. 21). Re-expression of the NYESO1-001-specific TCR 1G4 and mock expression are used as control.

For CD8+ T cells expressing TCR R43P3G5, no activation was observed upon co-culture with HLA-A*02 positive cell types from healthy tissues (see FIG. 33), while there was an activity towards the tumor cell lines UACC-257 and U266B1 expressing HLA-A*02 and MAGEA1 as source gene for MAGEA1-003 peptide (FIGS. 32 and 33). A corresponding pattern of reactivity was observed with CD8+ T cells expressing the NYESO1-specific control TCR 1G4, with reactivity towards NYESO1 expressing HLA-A*02 positive tumor cell lines but not towards the indicated panel of healthy tissue cells. T-cell activation upon co-culture with cell lines expressing HLA-A*02 and MAGEA1 reflects the recognition of endogenously expressed and presented target pHLA by TCRs R43P3G5.

Example 10: T-Cell Receptor R59P2E7

Figure 10:
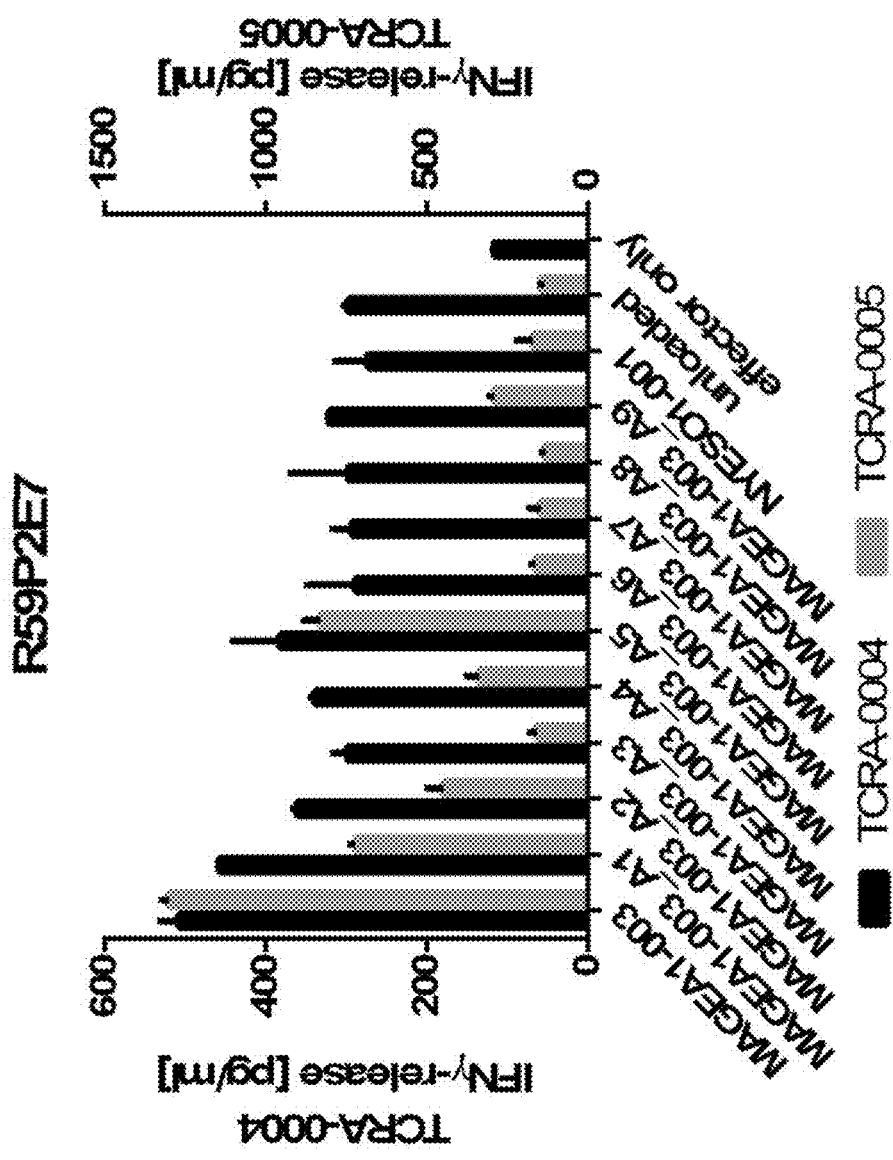
Figure 20:
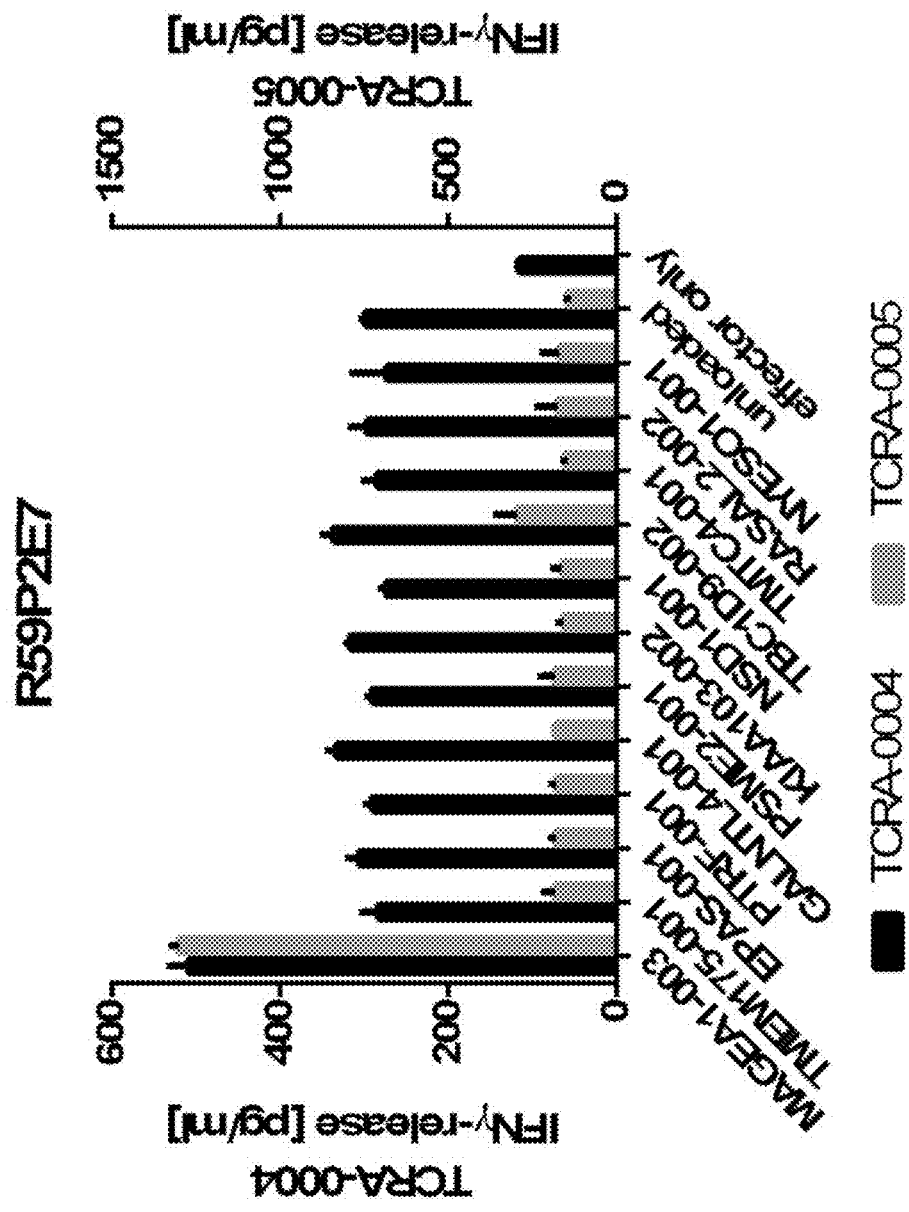
Figure 31:
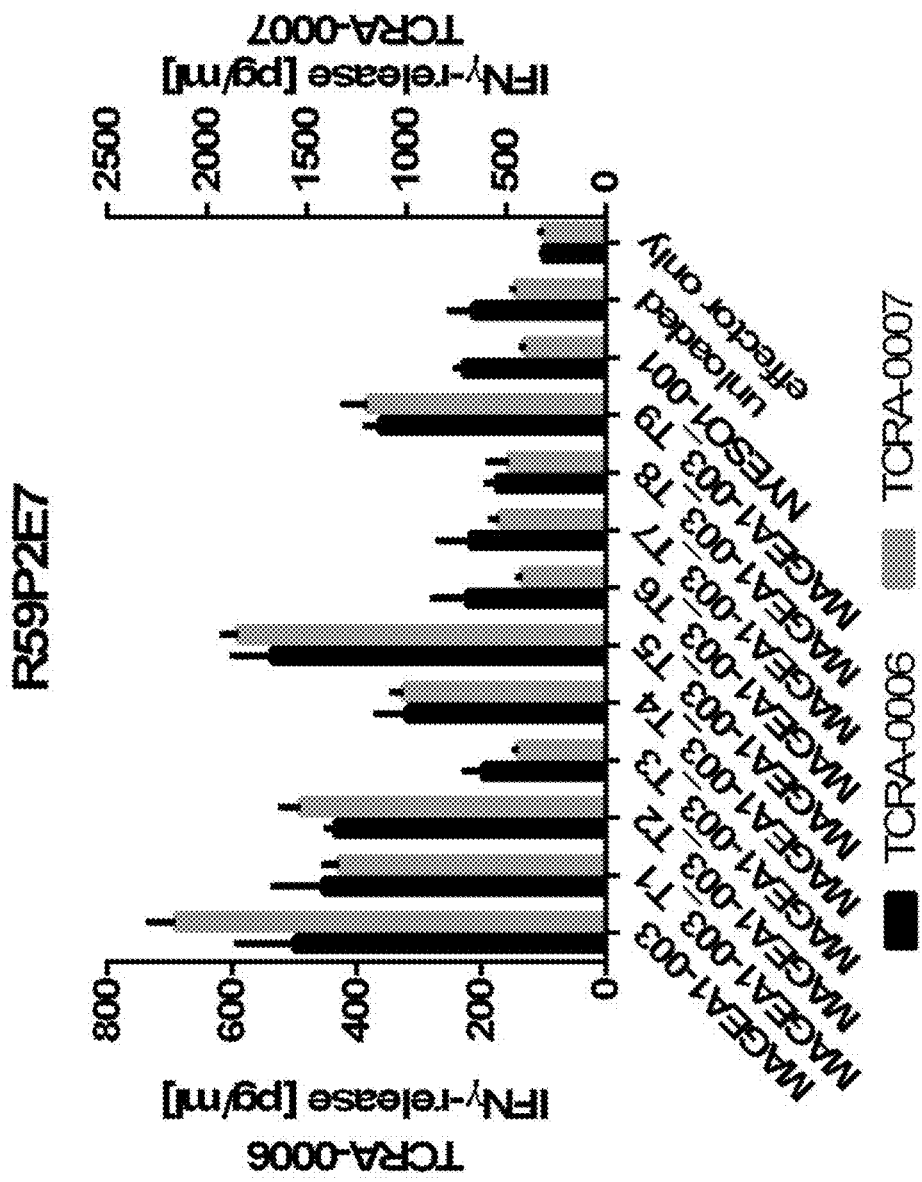

TCR R59P2E7 (SEQ ID NO: 109-120) is restricted towards HLA-A*02-presented MAGEA1-003 (SEQ ID NO: 133) (see FIG. 20). R59P2E7 specifically recognizes MAGEA1-003 as human primary CD8+ T-cells re-expressing this TCR release IFNγ upon co-incubation with HLA-A*02+ target cells loaded either with MAGEA1-003 peptide or alanine and threonine substitution variants of MAGEA1-003 (FIGS. 10 and 31). This TCR does specifically recognize MAGEA1-003, but not different peptides showing high degree of sequence similarity to MAGEA1-003 (FIG. 20). NYESO1-001 peptide is used as negative control. The TCR has an EC50 of 386 nM (FIG. 44).

Re-expression of R59P2E7 in human primary CD8+ T-cells leads to selective binding of HLA-A*02/MAGEA1-003 tetramers but not HLA-A*02/NYESO1-001 tetramers (FIG. 21). Re-expression of the NYESO1-001-specific TCR 1G4 and mock expression are used as control.

The invention claimed is:

1. A single chain T cell receptor (TCR) comprising SEQ ID NO: 49, SEQ ID NO: 51, SEQ ID NO: 55, and SEQ ID NO: 57,
wherein each of SEQ ID NO: 49, SEQ ID NO: 51, SEQ ID NO: 55, and SEQ ID NO: 57 comprise at most one conservative amino acid substitution.

2. The single chain TCR according to claim 1, wherein said single chain TCR specifically and/or selectively binds to SEQ ID NO: 133.

3. The single chain TCR according to claim 1, comprising a TCR α variable chain comprising an amino acid sequence having at least 95% identity to SEQ ID NO: 52 and a TCR β variable chain comprising an amino acid sequence at least having 95% identity to SEQ ID NO: 58.

4. A nucleic acid encoding for the single chain TCR according to claim 1.

5. A vector comprising a nucleic acid according to claim 4.

6. A host cell comprising the single chain TCR according to claim 1.

7. A pharmaceutical composition comprising the single chain TCR according to claim 1.

8. A method of manufacturing the single chain TCR, comprising
   providing a suitable host cell,
   providing a genetic construct comprising a coding sequence encoding the single chain TCR according to claim 1,
   introducing into said suitable host cell said genetic construct,
   expressing said genetic construct by said suitable host cell.

9. The method according to claim 8, further comprising isolation and purification of the single chain TCR from the suitable host cell and, optionally, reconstitution of the single chain TCR in a T-cell.

10. The single chain TCR of claim 1, comprising
   a CDR1α chain comprising the amino acid sequence of SEQ ID NO: 49,
   a CDR2α chain comprising the amino acid sequence of SEQ ID NO: 50,
   a CDR3α chain comprising the amino acid sequence of SEQ ID NO: 51,
   a CDR1β chain comprising the amino acid sequences of SEQ ID NO: 55,
   a CDR2β chain comprising the amino acid sequence of SEQ ID NO: 56, and
   a CDR3β chain comprising the amino acid sequence of SEQ ID NO: 57,
   wherein each of SEQ ID NOs: 49 and 55 comprise at most one conservative amino acid substitution.

11. The single chain TCR of claim 1, comprising
   a CDR1α chain comprising the amino acid sequence of SEQ ID NO: 49,
   a CDR2α chain comprising the amino acid sequence of SEQ ID NO: 50,
   a CDR3α chain comprising the amino acid sequence of SEQ ID NO: 51,
   a CDR1β chain comprising the amino acid sequences of SEQ ID NO: 55,
   a CDR2β chain comprising the amino acid sequence of SEQ ID NO: 56, and
   a CDR3β chain comprising the amino acid sequence of SEQ ID NO: 57,
   wherein each of SEQ ID NOs: 50 and 56 comprise at most one conservative amino acid substitution.

12. The single chain TCR of claim 1, comprising
   a CDR1α chain comprising the amino acid sequence of SEQ ID NO: 49,
   a CDR2α chain comprising the amino acid sequence of SEQ ID NO: 50,
   a CDR3α chain comprising the amino acid sequence of SEQ ID NO: 51,
   a CDR1β chain comprising the amino acid sequences of SEQ ID NO: 55,
   a CDR2β chain comprising the amino acid sequence of SEQ ID NO: 56, and
   a CDR3β chain comprising the amino acid sequence of SEQ ID NO: 57,
   wherein each of SEQ ID NOs: 51 and 57 comprise at most one conservative amino acid substitution.

13. The single chain TCR of claim 1, comprising
   a CDR1α chain comprising the amino acid sequence of SEQ ID NO: 49,
   a CDR2α chain comprising the amino acid sequence of SEQ ID NO: 50,
   a CDR3α chain comprising the amino acid sequence of SEQ ID NO: 51,
   a CDR1β chain comprising the amino acid sequences of SEQ ID NO: 55,
   a CDR2β chain comprising the amino acid sequence of SEQ ID NO: 56, and
   a CDR3β chain comprising the amino acid sequence of SEQ ID NO: 57.

14. The single chain TCR according to claim 13, wherein said single chain TCR specifically binds to SEQ ID NO: 133.

15. The single chain TCR of claim 1, wherein the single chain TCR is a soluble TCR.

* * * * *

SEQUENCE LISTING

```
<160> NUMBER OF SEQ ID NOS: 162

<210> SEQ ID NO 1
<211> LENGTH: 5
<212> TYPE: PRT
```

<213> ORGANISM: Homo sapiens

<400> SEQUENCE: 1

Thr Ser Ile Asn Asn
1               5

<210> SEQ ID NO 2
<211> LENGTH: 3
<212> TYPE: PRT
<213> ORGANISM: Homo sapiens

<400> SEQUENCE: 2

Ile Arg Ser
1

<210> SEQ ID NO 3
<211> LENGTH: 12
<212> TYPE: PRT
<213> ORGANISM: Homo sapiens

<400> SEQUENCE: 3

Cys Leu Ile Gly Ala Ser Gly Ser Arg Leu Thr Phe
1               5                   10

<210> SEQ ID NO 4
<211> LENGTH: 130
<212> TYPE: PRT
<213> ORGANISM: Homo sapiens

<400> SEQUENCE: 4

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Leu Ile Gly
            100                 105                 110

Ala Ser Gly Ser Arg Leu Thr Phe Gly Glu Gly Thr Gln Leu Thr Val
        115                 120                 125

Asn Pro
    130

<210> SEQ ID NO 5
<211> LENGTH: 141
<212> TYPE: PRT
<213> ORGANISM: Homo sapiens

<400> SEQUENCE: 5

Asp Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr

```
                35                  40                  45
Val Leu Asp Met Arg Ser Met Asp Phe Lys Ser Asn Ser Ala Val Ala
 50                  55                  60

Trp Ser Asn Lys Ser Asp Phe Ala Cys Ala Asn Ala Phe Asn Asn Ser
 65                  70                  75                  80

Ile Ile Pro Glu Asp Thr Phe Phe Pro Pro Glu Ser Ser Cys Asp
                 85                  90                  95

Val Lys Leu Val Glu Lys Ser Phe Glu Thr Asp Thr Asn Leu Asn Phe
                100                 105                 110

Gln Asn Leu Ser Val Ile Gly Phe Arg Ile Leu Leu Lys Val Ala
        115                 120                 125

Gly Phe Asn Leu Leu Met Thr Leu Arg Leu Trp Ser Ser
130                 135                 140

<210> SEQ ID NO 6
<211> LENGTH: 271
<212> TYPE: PRT
<213> ORGANISM: Homo sapiens

<400> SEQUENCE: 6

Met Glu Thr Leu Leu Gly Val Ser Leu Val Ile Leu Trp Leu Gln Leu
 1               5                  10                  15

Ala Arg Val Asn Ser Gln Gln Gly Glu Glu Asp Pro Gln Ala Leu Ser
                 20                  25                  30

Ile Gln Glu Gly Glu Asn Ala Thr Met Asn Cys Ser Tyr Lys Thr Ser
             35                  40                  45

Ile Asn Asn Leu Gln Trp Tyr Arg Gln Asn Ser Gly Arg Gly Leu Val
 50                  55                  60

His Leu Ile Leu Ile Arg Ser Asn Glu Arg Glu Lys His Ser Gly Arg
 65                  70                  75                  80

Leu Arg Val Thr Leu Asp Thr Ser Lys Lys Ser Ser Ser Leu Leu Ile
                 85                  90                  95

Thr Ala Ser Arg Ala Ala Asp Thr Ala Ser Tyr Phe Cys Leu Ile Gly
            100                 105                 110

Ala Ser Gly Ser Arg Leu Thr Phe Gly Glu Gly Thr Gln Leu Thr Val
        115                 120                 125

Asn Pro Asp Ile Gln Asn Pro Asp Pro Ala Val Tyr Gln Leu Arg Asp
130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270
```

```
<210> SEQ ID NO 7
<211> LENGTH: 5
<212> TYPE: PRT
<213> ORGANISM: Homo sapiens

<400> SEQUENCE: 7

Ser Gly His Asp Tyr
1               5

<210> SEQ ID NO 8
<211> LENGTH: 6
<212> TYPE: PRT
<213> ORGANISM: Homo sapiens

<400> SEQUENCE: 8

Phe Asn Asn Asn Val Pro
1               5

<210> SEQ ID NO 9
<211> LENGTH: 14
<212> TYPE: PRT
<213> ORGANISM: Homo sapiens

<400> SEQUENCE: 9

Cys Ala Ser Ser Tyr Phe Gly Trp Asn Glu Lys Leu Phe Phe
1               5                   10

<210> SEQ ID NO 10
<211> LENGTH: 133
<212> TYPE: PRT
<213> ORGANISM: Homo sapiens

<400> SEQUENCE: 10

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Tyr Phe Gly Trp Asn Glu Lys Leu Phe Phe Gly Ser Gly Thr
        115                 120                 125

Gln Leu Ser Val Leu
    130

<210> SEQ ID NO 11
<211> LENGTH: 177
<212> TYPE: PRT
<213> ORGANISM: Homo sapiens

<400> SEQUENCE: 11

Glu Asp Leu Asn Lys Val Phe Pro Pro Glu Val Ala Val Phe Glu Pro
1               5                   10                  15
```

```
Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 12
<211> LENGTH: 310
<212> TYPE: PRT
<213> ORGANISM: Homo sapiens

<400> SEQUENCE: 12

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Tyr Phe Gly Trp Asn Glu Lys Leu Phe Phe Gly Ser Gly Thr
        115                 120                 125

Gln Leu Ser Val Leu Glu Asp Leu Asn Lys Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205
```

```
Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
                260                 265                 270

Gln Gly Val Leu Ser Ala Thr Ile Leu Tyr Glu Ile Leu Leu Gly Lys
                275                 280                 285

Ala Thr Leu Tyr Ala Val Leu Val Ser Ala Leu Val Leu Met Ala Met
290                 295                 300

Val Lys Arg Lys Asp Phe
305             310

<210> SEQ ID NO 13
<211> LENGTH: 6
<212> TYPE: PRT
<213> ORGANISM: Homo sapiens

<400> SEQUENCE: 13

Asn Ser Ala Phe Gln Tyr
1               5

<210> SEQ ID NO 14
<211> LENGTH: 2
<212> TYPE: PRT
<213> ORGANISM: Homo sapiens

<400> SEQUENCE: 14

Thr Tyr
1

<210> SEQ ID NO 15
<211> LENGTH: 15
<212> TYPE: PRT
<213> ORGANISM: Homo sapiens

<400> SEQUENCE: 15

Cys Ala Met Ser Asp Val Ser Gly Gly Tyr Asn Lys Leu Ile Phe
1               5                   10                  15

<210> SEQ ID NO 16
<211> LENGTH: 135
<212> TYPE: PRT
<213> ORGANISM: Homo sapiens

<400> SEQUENCE: 16

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
                20                  25                  30

Leu Ser Val Pro Glu Gly Ala Ile Val Ser Leu Asn Cys Thr Tyr Ser
                35                  40                  45

Asn Ser Ala Phe Gln Tyr Phe Met Trp Tyr Arg Gln Tyr Ser Arg Lys
            50                  55                  60

Gly Pro Glu Leu Leu Met Tyr Thr Tyr Ser Ser Gly Asn Lys Glu Asp
65              70                  75                  80

Gly Arg Phe Thr Ala Gln Val Asp Lys Ser Ser Lys Tyr Ile Ser Leu
                85                  90                  95
```

```
Phe Ile Arg Asp Ser Gln Pro Ser Asp Ser Ala Thr Tyr Leu Cys Ala
            100                 105                 110

Met Ser Asp Val Ser Gly Gly Tyr Asn Lys Leu Ile Phe Gly Ala Gly
        115                 120                 125

Thr Arg Leu Ala Val His Pro
130                 135

<210> SEQ ID NO 17
<211> LENGTH: 141
<212> TYPE: PRT
<213> ORGANISM: Homo sapiens

<400> SEQUENCE: 17

Tyr Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 18
<211> LENGTH: 276
<212> TYPE: PRT
<213> ORGANISM: Homo sapiens

<400> SEQUENCE: 18

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Ser Asp Val Ser Gly Gly Tyr Asn Lys Leu Ile Phe Gly Ala Gly
        115                 120                 125

Thr Arg Leu Ala Val His Pro Tyr Ile Gln Asn Pro Asp Pro Ala Val
    130                 135                 140
```

Tyr Gln Leu Arg Asp Ser Lys Ser Asp Lys Ser Val Cys Leu Phe
145                 150                 155                 160

Thr Asp Phe Asp Ser Gln Thr Asn Val Ser Gln Ser Lys Asp Ser Asp
            165                 170                 175

Val Tyr Ile Thr Asp Lys Thr Val Leu Asp Met Arg Ser Met Asp Phe
        180                 185                 190

Lys Ser Asn Ser Ala Val Ala Trp Ser Asn Lys Ser Asp Phe Ala Cys
            195                 200                 205

Ala Asn Ala Phe Asn Asn Ser Ile Ile Pro Glu Asp Thr Phe Phe Pro
        210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
            245                 250                 255

Ile Leu Leu Leu Lys Val Ala Gly Phe Asn Leu Leu Met Thr Leu Arg
        260                 265                 270

Leu Trp Ser Ser
        275

<210> SEQ ID NO 19
<211> LENGTH: 5
<212> TYPE: PRT
<213> ORGANISM: Homo sapiens

<400> SEQUENCE: 19

Met Asn His Glu Tyr
1               5

<210> SEQ ID NO 20
<211> LENGTH: 6
<212> TYPE: PRT
<213> ORGANISM: Homo sapiens

<400> SEQUENCE: 20

Ser Met Asn Val Glu Val
1               5

<210> SEQ ID NO 21
<211> LENGTH: 14
<212> TYPE: PRT
<213> ORGANISM: Homo sapiens

<400> SEQUENCE: 21

Cys Ala Ser Thr Thr Pro Asp Gly Thr Asp Glu Gln Phe Phe
1               5                   10

<210> SEQ ID NO 22
<211> LENGTH: 132
<212> TYPE: PRT
<213> ORGANISM: Homo sapiens

<400> SEQUENCE: 22

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln

```
                 50                  55                  60

Ile Tyr Tyr Ser Met Asn Val Glu Val Thr Asp Lys Gly Asp Val Pro
 65                  70                  75                  80

Glu Gly Tyr Lys Val Ser Arg Lys Glu Lys Arg Asn Phe Pro Leu Ile
                 85                  90                  95

Leu Glu Ser Pro Ser Pro Asn Gln Thr Ser Leu Tyr Phe Cys Ala Ser
                100                 105                 110

Thr Thr Pro Asp Gly Thr Asp Glu Gln Phe Phe Gly Pro Gly Thr Arg
            115                 120                 125

Leu Thr Val Leu
            130

<210> SEQ ID NO 23
<211> LENGTH: 179
<212> TYPE: PRT
<213> ORGANISM: Homo sapiens

<400> SEQUENCE: 23

Glu Asp Leu Lys Asn Val Phe Pro Pro Glu Val Ala Val Phe Glu Pro
 1               5                  10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
            35                  40                  45

Gly Lys Glu Val His Ser Gly Val Ser Thr Asp Pro Gln Pro Leu Lys
     50                  55                  60

Glu Gln Pro Ala Leu Asn Asp Ser Arg Tyr Cys Leu Ser Ser Arg Leu
 65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Glu Ser Tyr Gln Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 24
<211> LENGTH: 311
<212> TYPE: PRT
<213> ORGANISM: Homo sapiens

<400> SEQUENCE: 24

Met Gly Pro Gln Leu Leu Gly Tyr Val Val Leu Cys Leu Leu Gly Ala
 1               5                  10                  15

Gly Pro Leu Glu Ala Gln Val Thr Gln Asn Pro Arg Tyr Leu Ile Thr
                20                  25                  30

Val Thr Gly Lys Lys Leu Thr Val Thr Cys Ser Gln Asn Met Asn His
            35                  40                  45

Glu Tyr Met Ser Trp Tyr Arg Gln Asp Pro Gly Leu Gly Leu Arg Gln
     50                  55                  60
```

```
Ile Tyr Tyr Ser Met Asn Val Glu Val Thr Asp Lys Gly Asp Val Pro
 65                  70                  75                  80

Glu Gly Tyr Lys Val Ser Arg Lys Glu Lys Arg Asn Phe Pro Leu Ile
             85                  90                  95

Leu Glu Ser Pro Ser Pro Asn Gln Thr Ser Leu Tyr Phe Cys Ala Ser
            100                 105                 110

Thr Thr Pro Asp Gly Thr Asp Glu Gln Phe Phe Gly Pro Gly Thr Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 25
<211> LENGTH: 6
<212> TYPE: PRT
<213> ORGANISM: Homo sapiens

<400> SEQUENCE: 25

Val Ser Gly Asn Pro Tyr
1               5

<210> SEQ ID NO 26
<211> LENGTH: 4
<212> TYPE: PRT
<213> ORGANISM: Homo sapiens

<400> SEQUENCE: 26

Tyr Ile Thr Gly
1

<210> SEQ ID NO 27
<211> LENGTH: 14
<212> TYPE: PRT
<213> ORGANISM: Homo sapiens

<400> SEQUENCE: 27
```

```
Cys Ala Val Arg Asp Met Asn Arg Asp Asp Lys Ile Ile Phe
1               5                   10
```

<210> SEQ ID NO 28
<211> LENGTH: 133
<212> TYPE: PRT
<213> ORGANISM: Homo sapiens

<400> SEQUENCE: 28

```
Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Met Asn Arg Asp Asp Lys Ile Ile Phe Gly Lys Gly Thr Arg
        115                 120                 125

Leu His Ile Leu Pro
        130
```

<210> SEQ ID NO 29
<211> LENGTH: 141
<212> TYPE: PRT
<213> ORGANISM: Homo sapiens

<400> SEQUENCE: 29

```
Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140
```

<210> SEQ ID NO 30
<211> LENGTH: 274
<212> TYPE: PRT
<213> ORGANISM: Homo sapiens

<400> SEQUENCE: 30

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Met Asn Arg Asp Asp Lys Ile Ile Phe Gly Lys Gly Thr Arg
        115                 120                 125

Leu His Ile Leu Pro Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 31
<211> LENGTH: 5
<212> TYPE: PRT
<213> ORGANISM: Homo sapiens

<400> SEQUENCE: 31

Leu Asn His Asp Ala
1               5

<210> SEQ ID NO 32
<211> LENGTH: 6
<212> TYPE: PRT
<213> ORGANISM: Homo sapiens

<400> SEQUENCE: 32

Ser Gln Ile Val Asn Asp
1               5

<210> SEQ ID NO 33

```
<211> LENGTH: 13
<212> TYPE: PRT
<213> ORGANISM: Homo sapiens

<400> SEQUENCE: 33

Cys Ala Ser Ser Arg Ala Glu Gly Gly Glu Gln Tyr Phe
1               5                   10

<210> SEQ ID NO 34
<211> LENGTH: 131
<212> TYPE: PRT
<213> ORGANISM: Homo sapiens

<400> SEQUENCE: 34

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Arg Ala Glu Gly Gly Glu Gln Tyr Phe Gly Pro Gly Thr Arg Leu
        115                 120                 125

Thr Val Thr
    130

<210> SEQ ID NO 35
<211> LENGTH: 179
<212> TYPE: PRT
<213> ORGANISM: Homo sapiens

<400> SEQUENCE: 35

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140
```

```
Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 36
<211> LENGTH: 310
<212> TYPE: PRT
<213> ORGANISM: Homo sapiens

<400> SEQUENCE: 36

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
                20                  25                  30

Lys Glu Gly Gln Asn Val Thr Leu Ser Cys Glu Gln Asn Leu Asn His
            35                  40                  45

Asp Ala Met Tyr Trp Tyr Arg Gln Asp Pro Gly Gln Gly Leu Arg Leu
        50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
                100                 105                 110

Ser Arg Ala Glu Gly Gly Glu Gln Tyr Phe Gly Pro Gly Thr Arg Leu
            115                 120                 125

Thr Val Thr Glu Asp Leu Lys Asn Val Phe Pro Pro Glu Val Ala Val
        130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
                180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
        210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
                260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
        290                 295                 300

Arg Lys Asp Ser Arg Gly
305                 310

<210> SEQ ID NO 37
<211> LENGTH: 6
```

```
<212> TYPE: PRT
<213> ORGANISM: Homo sapiens

<400> SEQUENCE: 37

Asp Ser Ala Ser Asn Tyr
1               5

<210> SEQ ID NO 38
<211> LENGTH: 3
<212> TYPE: PRT
<213> ORGANISM: Homo sapiens

<400> SEQUENCE: 38

Ile Arg Ser
1

<210> SEQ ID NO 39
<211> LENGTH: 14
<212> TYPE: PRT
<213> ORGANISM: Homo sapiens

<400> SEQUENCE: 39

Cys Ala Ala Ser Pro Thr Gly Gly Tyr Asn Lys Leu Ile Phe
1               5                   10

<210> SEQ ID NO 40
<211> LENGTH: 132
<212> TYPE: PRT
<213> ORGANISM: Homo sapiens

<400> SEQUENCE: 40

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Pro Thr Gly Gly Tyr Asn Lys Leu Ile Phe Gly Ala Gly Thr Arg Leu
        115                 120                 125

Ala Val His Pro
        130

<210> SEQ ID NO 41
<211> LENGTH: 141
<212> TYPE: PRT
<213> ORGANISM: Homo sapiens

<400> SEQUENCE: 41

Tyr Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30
```

```
Asn Val Ser Gln Ser Lys Asp Ser Asp Val Tyr Ile Thr Asp Lys Thr
            35                  40                  45

Val Leu Asp Met Arg Ser Met Asp Phe Lys Ser Asn Ser Ala Val Ala
 50                  55                  60

Trp Ser Asn Lys Ser Asp Phe Ala Cys Ala Asn Ala Phe Asn Asn Ser
 65                  70                  75                  80

Ile Ile Pro Glu Asp Thr Phe Phe Pro Ser Pro Glu Ser Ser Cys Asp
                 85                  90                  95

Val Lys Leu Val Glu Lys Ser Phe Glu Thr Asp Thr Asn Leu Asn Phe
                100                 105                 110

Gln Asn Leu Ser Val Ile Gly Phe Arg Ile Leu Leu Leu Lys Val Ala
            115                 120                 125

Gly Phe Asn Leu Leu Met Thr Leu Arg Leu Trp Ser Ser
            130                 135                 140

<210> SEQ ID NO 42
<211> LENGTH: 273
<212> TYPE: PRT
<213> ORGANISM: Homo sapiens

<400> SEQUENCE: 42

Met Thr Ser Ile Arg Ala Val Phe Ile Phe Leu Trp Leu Gln Leu Asp
  1               5                  10                  15

Leu Val Asn Gly Glu Asn Val Glu Gln His Pro Ser Thr Leu Ser Val
                 20                  25                  30

Gln Glu Gly Asp Ser Ala Val Ile Lys Cys Thr Tyr Ser Asp Ser Ala
             35                  40                  45

Ser Asn Tyr Phe Pro Trp Tyr Lys Gln Glu Leu Gly Lys Arg Pro Gln
 50                  55                  60

Leu Ile Ile Asp Ile Arg Ser Asn Val Gly Glu Lys Lys Asp Gln Arg
 65                  70                  75                  80

Ile Ala Val Thr Leu Asn Lys Thr Ala Lys His Phe Ser Leu His Ile
                 85                  90                  95

Thr Glu Thr Gln Pro Glu Asp Ser Ala Val Tyr Phe Cys Ala Ala Ser
                100                 105                 110

Pro Thr Gly Gly Tyr Asn Lys Leu Ile Phe Gly Ala Gly Thr Arg Leu
            115                 120                 125

Ala Val His Pro Tyr Ile Gln Asn Pro Asp Pro Ala Val Tyr Gln Leu
            130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
            195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270
```

Ser

<210> SEQ ID NO 43
<211> LENGTH: 5
<212> TYPE: PRT
<213> ORGANISM: Homo sapiens

<400> SEQUENCE: 43

Met Asn His Glu Tyr
1               5

<210> SEQ ID NO 44
<211> LENGTH: 6
<212> TYPE: PRT
<213> ORGANISM: Homo sapiens

<400> SEQUENCE: 44

Ser Val Gly Ala Gly Ile
1               5

<210> SEQ ID NO 45
<211> LENGTH: 14
<212> TYPE: PRT
<213> ORGANISM: Homo sapiens

<400> SEQUENCE: 45

Cys Ala Ser Ser Leu Gly Gly Ala Ser Gln Glu Gln Tyr Phe
1               5                   10

<210> SEQ ID NO 46
<211> LENGTH: 132
<212> TYPE: PRT
<213> ORGANISM: Homo sapiens

<400> SEQUENCE: 46

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
                20                  25                  30

Lys Thr Gly Gln Ser Met Thr Leu Gln Cys Ala Gln Asp Met Asn His
            35                  40                  45

Glu Tyr Met Ser Trp Tyr Arg Gln Asp Pro Gly Met Gly Leu Arg Leu
        50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Leu Gly Gly Ala Ser Gln Glu Gln Tyr Phe Gly Pro Gly Thr Arg
        115                 120                 125

Leu Thr Val Thr
    130

<210> SEQ ID NO 47
<211> LENGTH: 179
<212> TYPE: PRT
<213> ORGANISM: Homo sapiens

<400> SEQUENCE: 47

```
Glu Asp Leu Lys Asn Val Phe Pro Pro Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
            35                  40                  45

Gly Lys Glu Val His Ser Gly Val Ser Thr Asp Pro Gln Pro Leu Lys
50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
                115                 120                 125

Ala Asp Cys Gly Phe Thr Ser Glu Ser Tyr Gln Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 48
<211> LENGTH: 311
<212> TYPE: PRT
<213> ORGANISM: Homo sapiens

<400> SEQUENCE: 48

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
            35                  40                  45

Glu Tyr Met Ser Trp Tyr Arg Gln Asp Pro Gly Met Gly Leu Arg Leu
50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
                100                 105                 110

Ser Leu Gly Gly Ala Ser Gln Glu Gln Tyr Phe Gly Pro Gly Thr Arg
                115                 120                 125

Leu Thr Val Thr Glu Asp Leu Lys Asn Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
                180                 185                 190
```

```
Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
            290                 295                 300

Lys Arg Lys Asp Ser Arg Gly
305                 310
```

<210> SEQ ID NO 49
<211> LENGTH: 7
<212> TYPE: PRT
<213> ORGANISM: Homo sapiens

<400> SEQUENCE: 49

```
Thr Ile Ser Gly Thr Asp Tyr
1               5
```

<210> SEQ ID NO 50
<211> LENGTH: 1
<212> TYPE: PRT
<213> ORGANISM: Homo sapiens

<400> SEQUENCE: 50

```
Gly
1
```

<210> SEQ ID NO 51
<211> LENGTH: 11
<212> TYPE: PRT
<213> ORGANISM: Homo sapiens

<400> SEQUENCE: 51

```
Cys Ile Leu Phe Asn Phe Asn Lys Phe Tyr Phe
1               5                   10
```

<210> SEQ ID NO 52
<211> LENGTH: 125
<212> TYPE: PRT
<213> ORGANISM: Homo sapiens

<400> SEQUENCE: 52

```
Met Lys Leu Val Thr Ser Ile Thr Val Leu Leu Ser Leu Gly Ile Met
1               5                   10                  15

Gly Asp Ala Lys Thr Thr Gln Pro Asn Ser Met Glu Ser Asn Glu Glu
                20                  25                  30

Glu Pro Val His Leu Pro Cys Asn His Ser Thr Ile Ser Gly Thr Asp
            35                  40                  45

Tyr Ile His Trp Tyr Arg Gln Leu Pro Ser Gln Gly Pro Glu Tyr Val
        50                  55                  60

Ile His Gly Leu Thr Ser Asn Val Asn Asn Arg Met Ala Ser Leu Ala
65                  70                  75                  80
```

Ile Ala Glu Asp Arg Lys Ser Ser Thr Leu Ile Leu His Arg Ala Thr
                85                  90                  95

Leu Arg Asp Ala Ala Val Tyr Tyr Cys Ile Leu Phe Asn Phe Asn Lys
                100                 105                 110

Phe Tyr Phe Gly Ser Gly Thr Lys Leu Asn Val Lys Pro
            115                 120                 125

<210> SEQ ID NO 53
<211> LENGTH: 141
<212> TYPE: PRT
<213> ORGANISM: Homo sapiens

<400> SEQUENCE: 53

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
                20                  25                  30

Asn Val Ser Gln Ser Lys Asp Ser Asp Val Tyr Ile Thr Asp Lys Thr
                35                  40                  45

Val Leu Asp Met Arg Ser Met Asp Phe Lys Ser Asn Ser Ala Val Ala
        50                  55                  60

Trp Ser Asn Lys Ser Asp Phe Ala Cys Ala Asn Ala Phe Asn Asn Ser
65              70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
                100                 105                 110

Gln Asn Leu Ser Val Ile Gly Phe Arg Ile Leu Leu Leu Lys Val Ala
                115                 120                 125

Gly Phe Asn Leu Leu Met Thr Leu Arg Leu Trp Ser Ser
            130                 135                 140

<210> SEQ ID NO 54
<211> LENGTH: 266
<212> TYPE: PRT
<213> ORGANISM: Homo sapiens

<400> SEQUENCE: 54

Met Lys Leu Val Thr Ser Ile Thr Val Leu Leu Ser Leu Gly Ile Met
1               5                   10                  15

Gly Asp Ala Lys Thr Thr Gln Pro Asn Ser Met Glu Ser Asn Glu Glu
                20                  25                  30

Glu Pro Val His Leu Pro Cys Asn His Ser Thr Ile Ser Gly Thr Asp
                35                  40                  45

Tyr Ile His Trp Tyr Arg Gln Leu Pro Ser Gln Gly Pro Glu Tyr Val
        50                  55                  60

Ile His Gly Leu Thr Ser Asn Val Asn Asn Arg Met Ala Ser Leu Ala
65              70                  75                  80

Ile Ala Glu Asp Arg Lys Ser Ser Thr Leu Ile Leu His Arg Ala Thr
                85                  90                  95

Leu Arg Asp Ala Ala Val Tyr Tyr Cys Ile Leu Phe Asn Phe Asn Lys
                100                 105                 110

Phe Tyr Phe Gly Ser Gly Thr Lys Leu Asn Val Lys Pro Asn Ile Gln
            115                 120                 125

Asn Pro Asp Pro Ala Val Tyr Gln Leu Arg Asp Ser Lys Ser Ser Asp
        130                 135                 140

Lys Ser Val Cys Leu Phe Thr Asp Phe Asp Ser Gln Thr Asn Val Ser
145                 150                 155                 160

Gln Ser Lys Asp Ser Asp Val Tyr Ile Thr Asp Lys Thr Val Leu Asp
            165                 170                 175

Met Arg Ser Met Asp Phe Lys Ser Asn Ser Ala Val Ala Trp Ser Asn
        180                 185                 190

Lys Ser Asp Phe Ala Cys Ala Asn Ala Phe Asn Asn Ser Ile Ile Pro
            195                 200                 205

Glu Asp Thr Phe Phe Pro Ser Pro Glu Ser Ser Cys Asp Val Lys Leu
        210                 215                 220

Val Glu Lys Ser Phe Glu Thr Asp Thr Asn Leu Asn Phe Gln Asn Leu
225                 230                 235                 240

Ser Val Ile Gly Phe Arg Ile Leu Leu Leu Lys Val Ala Gly Phe Asn
                245                 250                 255

Leu Leu Met Thr Leu Arg Leu Trp Ser Ser
            260                 265

<210> SEQ ID NO 55
<211> LENGTH: 5
<212> TYPE: PRT
<213> ORGANISM: Homo sapiens

<400> SEQUENCE: 55

Leu Asn His Asn Val
1               5

<210> SEQ ID NO 56
<211> LENGTH: 6
<212> TYPE: PRT
<213> ORGANISM: Homo sapiens

<400> SEQUENCE: 56

Tyr Tyr Asp Lys Asp Phe
1               5

<210> SEQ ID NO 57
<211> LENGTH: 14
<212> TYPE: PRT
<213> ORGANISM: Homo sapiens

<400> SEQUENCE: 57

Cys Ala Thr Ser Ser Gly Glu Thr Asn Glu Lys Leu Phe Phe
1               5                   10

<210> SEQ ID NO 58
<211> LENGTH: 132
<212> TYPE: PRT
<213> ORGANISM: Homo sapiens

<400> SEQUENCE: 58

Met Gly Pro Gly Leu Leu His Trp Met Ala Leu Cys Leu Leu Gly Thr
1               5                   10                  15

Gly His Gly Asp Ala Met Val Ile Gln Asn Pro Arg Tyr Gln Val Thr
            20                  25                  30

Gln Phe Gly Lys Pro Val Thr Leu Ser Cys Ser Gln Thr Leu Asn His
        35                  40                  45

Asn Val Met Tyr Trp Tyr Gln Gln Lys Ser Ser Gln Ala Pro Lys Leu
    50                  55                  60

Leu Phe His Tyr Tyr Asp Lys Asp Phe Asn Asn Glu Ala Asp Thr Pro

```
                65                  70                  75                  80

Asp Asn Phe Gln Ser Arg Arg Pro Asn Thr Ser Phe Cys Phe Leu Asp
                    85                  90                  95

Ile Arg Ser Pro Gly Leu Gly Asp Ala Ala Met Tyr Leu Cys Ala Thr
                100                 105                 110

Ser Ser Gly Glu Thr Asn Glu Lys Leu Phe Phe Gly Ser Gly Thr Gln
                115                 120                 125

Leu Ser Val Leu
            130

<210> SEQ ID NO 59
<211> LENGTH: 177
<212> TYPE: PRT
<213> ORGANISM: Homo sapiens

<400> SEQUENCE: 59

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Phe Pro Asp His Val Glu Leu Ser Trp Trp Val Asn
                35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
                115                 120                 125

Ala Asp Cys Gly Phe Thr Ser Val Ser Tyr Gln Gln Gly Val Leu Ser
            130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 60
<211> LENGTH: 309
<212> TYPE: PRT
<213> ORGANISM: Homo sapiens

<400> SEQUENCE: 60

Met Gly Pro Gly Leu Leu His Trp Met Ala Leu Cys Leu Leu Gly Thr
1               5                   10                  15

Gly His Gly Asp Ala Met Val Ile Gln Asn Pro Arg Tyr Gln Val Thr
                20                  25                  30

Gln Phe Gly Lys Pro Val Thr Leu Ser Cys Ser Gln Thr Leu Asn His
                35                  40                  45

Asn Val Met Tyr Trp Tyr Gln Gln Lys Ser Ser Gln Ala Pro Lys Leu
    50                  55                  60

Leu Phe His Tyr Tyr Asp Lys Asp Phe Asn Asn Glu Ala Asp Thr Pro
65                  70                  75                  80
```

Asp Asn Phe Gln Ser Arg Arg Pro Asn Thr Ser Phe Cys Phe Leu Asp
                85                  90                  95

Ile Arg Ser Pro Gly Leu Gly Asp Ala Ala Met Tyr Leu Cys Ala Thr
            100                 105                 110

Ser Ser Gly Glu Thr Asn Glu Lys Leu Phe Gly Ser Gly Thr Gln
        115                 120                 125

Leu Ser Val Leu Glu Asp Leu Asn Lys Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
            165                 170                 175

Trp Trp Val Asn Gly Lys Glu Val His Ser Gly Val Ser Thr Asp Pro
                180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
        290                 295                 300

Lys Arg Lys Asp Phe
305

<210> SEQ ID NO 61
<211> LENGTH: 7
<212> TYPE: PRT
<213> ORGANISM: Homo sapiens

<400> SEQUENCE: 61

Thr Ser Glu Ser Asn Tyr Tyr
1               5

<210> SEQ ID NO 62
<211> LENGTH: 4
<212> TYPE: PRT
<213> ORGANISM: Homo sapiens

<400> SEQUENCE: 62

Gln Glu Ala Tyr
1

<210> SEQ ID NO 63
<211> LENGTH: 15
<212> TYPE: PRT
<213> ORGANISM: Homo sapiens

<400> SEQUENCE: 63

Cys Ala Phe Gly Tyr Ser Gly Gly Gly Ala Asp Gly Leu Thr Phe
1               5                   10                  15

<210> SEQ ID NO 64
<211> LENGTH: 136
<212> TYPE: PRT
<213> ORGANISM: Homo sapiens

<400> SEQUENCE: 64

Met Thr Arg Val Ser Leu Leu Trp Ala Val Val Ser Thr Cys Leu
1               5                   10                  15

Glu Ser Gly Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asn Tyr Tyr Leu Phe Trp Tyr Lys Gln Pro Pro Ser Arg Gln
    50                  55                  60

Met Ile Leu Val Ile Arg Gln Glu Ala Tyr Lys Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Thr Ala Met Tyr Phe Cys
            100                 105                 110

Ala Phe Gly Tyr Ser Gly Gly Gly Ala Asp Gly Leu Thr Phe Gly Lys
        115                 120                 125

Gly Thr His Leu Ile Ile Gln Pro
    130                 135

<210> SEQ ID NO 65
<211> LENGTH: 141
<212> TYPE: PRT
<213> ORGANISM: Homo sapiens

<400> SEQUENCE: 65

Tyr Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 66
<211> LENGTH: 277
<212> TYPE: PRT
<213> ORGANISM: Homo sapiens

<400> SEQUENCE: 66

Met Thr Arg Val Ser Leu Leu Trp Ala Val Val Val Ser Thr Cys Leu

```
               1               5              10              15
            Glu Ser Gly Met Ala Gln Thr Val Thr Gln Ser Gln Pro Glu Met Ser
                           20                  25                  30

Val Gln Glu Ala Glu Thr Val Thr Leu Ser Cys Thr Tyr Asp Thr Ser
                           35                  40                  45

Glu Ser Asn Tyr Tyr Leu Phe Trp Tyr Lys Gln Pro Ser Arg Gln
                           50                  55              60

Met Ile Leu Val Ile Arg Gln Glu Ala Tyr Lys Gln Asn Ala Thr
             65                  70                  75                  80

Glu Asn Arg Phe Ser Val Asn Phe Gln Lys Ala Ala Lys Ser Phe Ser
                               85                  90                  95

Leu Lys Ile Ser Asp Ser Gln Leu Gly Asp Thr Ala Met Tyr Phe Cys
                           100                 105                 110

Ala Phe Gly Tyr Ser Gly Gly Ala Asp Gly Leu Thr Phe Gly Lys
                           115                 120                 125

Gly Thr His Leu Ile Ile Gln Pro Tyr Ile Gln Asn Pro Asp Pro Ala
                130                 135                 140

Val Tyr Gln Leu Arg Asp Ser Lys Ser Ser Asp Lys Ser Val Cys Leu
            145                 150                 155                 160

Phe Thr Asp Phe Asp Ser Gln Thr Asn Val Ser Gln Ser Lys Asp Ser
                               165                 170                 175

Asp Val Tyr Ile Thr Asp Lys Thr Val Leu Asp Met Arg Ser Met Asp
                           180                 185                 190

Phe Lys Ser Asn Ser Ala Val Ala Trp Ser Asn Lys Ser Asp Phe Ala
                           195                 200                 205

Cys Ala Asn Ala Phe Asn Asn Ser Ile Ile Pro Glu Asp Thr Phe Phe
                           210                 215                 220

Pro Ser Pro Glu Ser Ser Cys Asp Val Lys Leu Val Glu Lys Ser Phe
            225                 230                 235                 240

Glu Thr Asp Thr Asn Leu Asn Phe Gln Asn Leu Ser Val Ile Gly Phe
                               245                 250                 255

Arg Ile Leu Leu Leu Lys Val Ala Gly Phe Asn Leu Leu Met Thr Leu
                           260                 265                 270

Arg Leu Trp Ser Ser
                           275

<210> SEQ ID NO 67
<211> LENGTH: 5
<212> TYPE: PRT
<213> ORGANISM: Homo sapiens

<400> SEQUENCE: 67

Ser Gly His Asp Thr
1               5

<210> SEQ ID NO 68
<211> LENGTH: 6
<212> TYPE: PRT
<213> ORGANISM: Homo sapiens

<400> SEQUENCE: 68

Tyr Tyr Glu Glu Glu Glu
1               5

<210> SEQ ID NO 69
<211> LENGTH: 16
<212> TYPE: PRT
```

<213> ORGANISM: Homo sapiens

<400> SEQUENCE: 69

Cys Ala Ser Ser Asn Glu Gly Gln Gly Trp Glu Ala Glu Ala Phe Phe
1               5                   10                  15

<210> SEQ ID NO 70
<211> LENGTH: 134
<212> TYPE: PRT
<213> ORGANISM: Homo sapiens

<400> SEQUENCE: 70

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Asn Glu Gly Gln Gly Trp Glu Ala Glu Ala Phe Phe Gly Gln Gly
        115                 120                 125

Thr Arg Leu Thr Val Val
    130

<210> SEQ ID NO 71
<211> LENGTH: 177
<212> TYPE: PRT
<213> ORGANISM: Homo sapiens

<400> SEQUENCE: 71

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
            165                 170                 175
Phe

<210> SEQ ID NO 72
<211> LENGTH: 311
<212> TYPE: PRT
<213> ORGANISM: Homo sapiens

<400> SEQUENCE: 72

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Asn Glu Gly Gln Gly Trp Glu Ala Glu Ala Phe Phe Gly Gln Gly
        115                 120                 125

Thr Arg Leu Thr Val Val Glu Asp Leu Asn Lys Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Val Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp Phe
305                 310

<210> SEQ ID NO 73
<211> LENGTH: 5
<212> TYPE: PRT
<213> ORGANISM: Homo sapiens

-continued

<400> SEQUENCE: 73

Asp Ser Val Asn Asn
1               5

<210> SEQ ID NO 74
<211> LENGTH: 1
<212> TYPE: PRT
<213> ORGANISM: Homo sapiens

<400> SEQUENCE: 74

Ile
1

<210> SEQ ID NO 75
<211> LENGTH: 11
<212> TYPE: PRT
<213> ORGANISM: Homo sapiens

<400> SEQUENCE: 75

Cys Ala Val His Asn Phe Asn Lys Phe Tyr Phe
1               5                   10

<210> SEQ ID NO 76
<211> LENGTH: 127
<212> TYPE: PRT
<213> ORGANISM: Homo sapiens

<400> SEQUENCE: 76

Met Lys Arg Ile Leu Gly Ala Leu Leu Gly Leu Leu Ser Ala Gln Val
1               5                   10                  15

Cys Cys Val Arg Gly Ile Gln Val Glu Gln Ser Pro Pro Asp Leu Ile
            20                  25                  30

Leu Gln Glu Gly Ala Asn Ser Thr Leu Arg Cys Asn Phe Ser Asp Ser
        35                  40                  45

Val Asn Asn Leu Gln Trp Phe His Gln Asn Pro Trp Gly Gln Leu Ile
    50                  55                  60

Asn Leu Phe Tyr Ile Pro Ser Gly Thr Lys Gln Asn Gly Arg Leu Ser
65                  70                  75                  80

Ala Thr Thr Val Ala Thr Glu Arg Tyr Ser Leu Leu Tyr Ile Ser Ser
                85                  90                  95

Ser Gln Thr Thr Asp Ser Gly Val Tyr Phe Cys Ala Val His Asn Phe
            100                 105                 110

Asn Lys Phe Tyr Phe Gly Ser Gly Thr Lys Leu Asn Val Lys Pro
        115                 120                 125

<210> SEQ ID NO 77
<211> LENGTH: 141
<212> TYPE: PRT
<213> ORGANISM: Homo sapiens

<400> SEQUENCE: 77

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

```
Trp Ser Asn Lys Ser Asp Phe Ala Cys Ala Asn Ala Phe Asn Asn Ser
 65                  70                  75                  80

Ile Ile Pro Glu Asp Thr Phe Phe Pro Ser Pro Glu Ser Ser Cys Asp
                 85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
130                 135                 140
```

<210> SEQ ID NO 78
<211> LENGTH: 268
<212> TYPE: PRT
<213> ORGANISM: Homo sapiens

<400> SEQUENCE: 78

```
Met Lys Arg Ile Leu Gly Ala Leu Leu Gly Leu Leu Ser Ala Gln Val
  1               5                  10                  15

Cys Cys Val Arg Gly Ile Gln Val Glu Gln Ser Pro Pro Asp Leu Ile
             20                  25                  30

Leu Gln Glu Gly Ala Asn Ser Thr Leu Arg Cys Asn Phe Ser Asp Ser
         35                  40                  45

Val Asn Asn Leu Gln Trp Phe His Gln Asn Pro Trp Gly Gln Leu Ile
 50                  55                  60

Asn Leu Phe Tyr Ile Pro Ser Gly Thr Lys Gln Asn Gly Arg Leu Ser
 65                  70                  75                  80

Ala Thr Thr Val Ala Thr Glu Arg Tyr Ser Leu Leu Tyr Ile Ser Ser
                 85                  90                  95

Ser Gln Thr Thr Asp Ser Gly Val Tyr Phe Cys Ala Val His Asn Phe
            100                 105                 110

Asn Lys Phe Tyr Phe Gly Ser Gly Thr Lys Leu Asn Val Lys Pro Asn
        115                 120                 125

Ile Gln Asn Pro Asp Pro Ala Val Tyr Gln Leu Arg Asp Ser Lys Ser
130                 135                 140

Ser Asp Lys Ser Val Cys Leu Phe Thr Asp Phe Asp Ser Gln Thr Asn
145                 150                 155                 160

Val Ser Gln Ser Lys Asp Ser Asp Val Tyr Ile Thr Asp Lys Thr Val
                165                 170                 175

Leu Asp Met Arg Ser Met Asp Phe Lys Ser Asn Ser Ala Val Ala Trp
            180                 185                 190

Ser Asn Lys Ser Asp Phe Ala Cys Ala Asn Ala Phe Asn Asn Ser Ile
        195                 200                 205

Ile Pro Glu Asp Thr Phe Phe Pro Ser Pro Glu Ser Ser Cys Asp Val
210                 215                 220

Lys Leu Val Glu Lys Ser Phe Glu Thr Asp Thr Asn Leu Asn Phe Gln
225                 230                 235                 240

Asn Leu Ser Val Ile Gly Phe Arg Ile Leu Leu Leu Lys Val Ala Gly
                245                 250                 255

Phe Asn Leu Leu Met Thr Leu Arg Leu Trp Ser Ser
            260                 265
```

<210> SEQ ID NO 79
<211> LENGTH: 5
<212> TYPE: PRT

```
<213> ORGANISM: Homo sapiens

<400> SEQUENCE: 79

Pro Arg His Asp Thr
1               5

<210> SEQ ID NO 80
<211> LENGTH: 6
<212> TYPE: PRT
<213> ORGANISM: Homo sapiens

<400> SEQUENCE: 80

Phe Tyr Glu Lys Met Gln
1               5

<210> SEQ ID NO 81
<211> LENGTH: 15
<212> TYPE: PRT
<213> ORGANISM: Homo sapiens

<400> SEQUENCE: 81

Cys Ala Ser Ser Leu Leu Gly Gln Gly Tyr Asn Glu Gln Phe Phe
1               5                   10                  15

<210> SEQ ID NO 82
<211> LENGTH: 143
<212> TYPE: PRT
<213> ORGANISM: Homo sapiens

<400> SEQUENCE: 82

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
                20                  25                  30

Val Ile Gln Ser Pro Arg His Leu Ile Lys Glu Lys Arg Glu Thr Ala
            35                  40                  45

Thr Leu Lys Cys Tyr Pro Ile Pro Arg His Asp Thr Val Tyr Trp Tyr
        50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Leu Leu Gly Gln Gly
        115                 120                 125

Tyr Asn Glu Gln Phe Phe Gly Pro Gly Thr Arg Leu Thr Val Leu
    130                 135                 140

<210> SEQ ID NO 83
<211> LENGTH: 179
<212> TYPE: PRT
<213> ORGANISM: Homo sapiens

<400> SEQUENCE: 83

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
```

```
                35                  40                  45
Gly Lys Glu Val His Ser Gly Val Ser Thr Asp Pro Gln Pro Leu Lys
 50                  55                  60
Glu Gln Pro Ala Leu Asn Asp Ser Arg Tyr Cys Leu Ser Ser Arg Leu
 65                  70                  75                  80
Arg Val Ser Ala Thr Phe Trp Gln Asn Pro Arg Asn His Phe Arg Cys
                 85                  90                  95
Gln Val Gln Phe Tyr Gly Leu Ser Glu Asn Asp Glu Trp Thr Gln Asp
                100                 105                 110
Arg Ala Lys Pro Val Thr Gln Ile Val Ser Ala Glu Ala Trp Gly Arg
                115                 120                 125
Ala Asp Cys Gly Phe Thr Ser Glu Ser Tyr Gln Gln Gly Val Leu Ser
130                 135                 140
Ala Thr Ile Leu Tyr Glu Ile Leu Leu Gly Lys Ala Thr Leu Tyr Ala
145                 150                 155                 160
Val Leu Val Ser Ala Leu Val Leu Met Ala Met Val Lys Arg Lys Asp
                165                 170                 175
Ser Arg Gly

<210> SEQ ID NO 84
<211> LENGTH: 322
<212> TYPE: PRT
<213> ORGANISM: Homo sapiens

<400> SEQUENCE: 84

Met Leu Ser Pro Asp Leu Pro Asp Ser Ala Trp Asn Thr Arg Leu Leu
 1                5                  10                  15
Cys His Val Met Leu Cys Leu Leu Gly Ala Val Ser Val Ala Ala Gly
                 20                  25                  30
Val Ile Gln Ser Pro Arg His Leu Ile Lys Glu Lys Arg Glu Thr Ala
                 35                  40                  45
Thr Leu Lys Cys Tyr Pro Ile Pro Arg His Asp Thr Val Tyr Trp Tyr
 50                  55                  60
Gln Gln Gly Pro Gly Gln Asp Pro Gln Phe Leu Ile Ser Phe Tyr Glu
 65                  70                  75                  80
Lys Met Gln Ser Asp Lys Gly Ser Ile Pro Asp Arg Phe Ser Ala Gln
                 85                  90                  95
Gln Phe Ser Asp Tyr His Ser Glu Leu Asn Met Ser Ser Leu Glu Leu
                100                 105                 110
Gly Asp Ser Ala Leu Tyr Phe Cys Ala Ser Ser Leu Leu Gly Gln Gly
                115                 120                 125
Tyr Asn Glu Gln Phe Phe Gly Pro Gly Thr Arg Leu Thr Val Leu Glu
130                 135                 140
Asp Leu Lys Asn Val Phe Pro Pro Glu Val Ala Val Phe Glu Pro Ser
145                 150                 155                 160
Glu Ala Glu Ile Ser His Thr Gln Lys Ala Thr Leu Val Cys Leu Ala
                165                 170                 175
Thr Gly Phe Tyr Pro Asp His Val Glu Leu Ser Trp Trp Val Asn Gly
                180                 185                 190
Lys Glu Val His Ser Gly Val Ser Thr Asp Pro Gln Pro Leu Lys Glu
                195                 200                 205
Gln Pro Ala Leu Asn Asp Ser Arg Tyr Cys Leu Ser Ser Arg Leu Arg
210                 215                 220
Val Ser Ala Thr Phe Trp Gln Asn Pro Arg Asn His Phe Arg Cys Gln
```

```
            225                 230                 235                 240
Val Gln Phe Tyr Gly Leu Ser Glu Asn Asp Glu Trp Thr Gln Asp Arg
                245                 250                 255
Ala Lys Pro Val Thr Gln Ile Val Ser Ala Glu Ala Trp Gly Arg Ala
                260                 265                 270
Asp Cys Gly Phe Thr Ser Glu Ser Tyr Gln Gln Gly Val Leu Ser Ala
                275                 280                 285
Thr Ile Leu Tyr Glu Ile Leu Leu Gly Lys Ala Thr Leu Tyr Ala Val
                290                 295                 300
Leu Val Ser Ala Leu Val Leu Met Ala Met Val Lys Arg Lys Asp Ser
305                 310                 315                 320
Arg Gly

<210> SEQ ID NO 85
<211> LENGTH: 7
<212> TYPE: PRT
<213> ORGANISM: Homo sapiens

<400> SEQUENCE: 85

Thr Arg Asp Thr Thr Tyr Tyr
1               5

<210> SEQ ID NO 86
<211> LENGTH: 4
<212> TYPE: PRT
<213> ORGANISM: Homo sapiens

<400> SEQUENCE: 86

Arg Asn Ser Phe
1

<210> SEQ ID NO 87
<211> LENGTH: 14
<212> TYPE: PRT
<213> ORGANISM: Homo sapiens

<400> SEQUENCE: 87

Cys Ala Leu Ser Asn Asn Asn Ala Gly Asn Met Leu Thr Phe
1               5                   10

<210> SEQ ID NO 88
<211> LENGTH: 135
<212> TYPE: PRT
<213> ORGANISM: Homo sapiens

<400> SEQUENCE: 88

Met Leu Thr Ala Ser Leu Leu Arg Ala Val Ile Ala Ser Ile Cys Val
1               5                   10                  15
Val Ser Ser Met Ala Gln Lys Val Thr Gln Ala Gln Thr Glu Ile Ser
                20                  25                  30
Val Val Glu Lys Glu Asp Val Thr Leu Asp Cys Val Tyr Glu Thr Arg
            35                  40                  45
Asp Thr Thr Tyr Tyr Leu Phe Trp Tyr Lys Gln Pro Pro Ser Gly Glu
        50                  55                  60
Leu Val Phe Leu Ile Arg Arg Asn Ser Phe Asp Glu Gln Asn Glu Ile
65                  70                  75                  80
Ser Gly Arg Tyr Ser Trp Asn Phe Gln Lys Ser Thr Ser Ser Phe Asn
                85                  90                  95
Phe Thr Ile Thr Ala Ser Gln Val Val Asp Ser Ala Val Tyr Phe Cys
```

-continued

```
                100                 105                 110
Ala Leu Ser Asn Asn Ala Gly Asn Met Leu Thr Phe Gly Gly Gly
            115                 120                 125

Thr Arg Leu Met Val Lys Pro
        130                 135

<210> SEQ ID NO 89
<211> LENGTH: 141
<212> TYPE: PRT
<213> ORGANISM: Homo sapiens

<400> SEQUENCE: 89

His Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 90
<211> LENGTH: 276
<212> TYPE: PRT
<213> ORGANISM: Homo sapiens

<400> SEQUENCE: 90

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
            100                 105                 110

Ala Leu Ser Asn Asn Asn Ala Gly Asn Met Leu Thr Phe Gly Gly Gly
        115                 120                 125

Thr Arg Leu Met Val Lys Pro His Ile Gln Asn Pro Asp Pro Ala Val
    130                 135                 140

Tyr Gln Leu Arg Asp Ser Lys Ser Ser Asp Lys Ser Val Cys Leu Phe
```

```
                145                 150                 155                 160
        Thr Asp Phe Asp Ser Gln Thr Asn Val Ser Gln Ser Lys Asp Ser Asp
                        165                 170                 175

Val Tyr Ile Thr Asp Lys Thr Val Leu Asp Met Arg Ser Met Asp Phe
                        180                 185                 190

Lys Ser Asn Ser Ala Val Ala Trp Ser Asn Lys Ser Asp Phe Ala Cys
                        195                 200                 205

Ala Asn Ala Phe Asn Asn Ser Ile Ile Pro Glu Asp Thr Phe Phe Pro
                        210                 215                 220

Ser Pro Glu Ser Ser Cys Asp Val Lys Leu Val Glu Lys Ser Phe Glu
        225                 230                 235                 240

Thr Asp Thr Asn Leu Asn Phe Gln Asn Leu Ser Val Ile Gly Phe Arg
                        245                 250                 255

Ile Leu Leu Leu Lys Val Ala Gly Phe Asn Leu Leu Met Thr Leu Arg
                        260                 265                 270

Leu Trp Ser Ser
                        275
```

<210> SEQ ID NO 91
<211> LENGTH: 5
<212> TYPE: PRT
<213> ORGANISM: Homo sapiens

<400> SEQUENCE: 91

```
Pro Arg His Asp Thr
1               5
```

<210> SEQ ID NO 92
<211> LENGTH: 6
<212> TYPE: PRT
<213> ORGANISM: Homo sapiens

<400> SEQUENCE: 92

```
Phe Tyr Glu Lys Met Gln
1               5
```

<210> SEQ ID NO 93
<211> LENGTH: 16
<212> TYPE: PRT
<213> ORGANISM: Homo sapiens

<400> SEQUENCE: 93

```
Cys Ala Ser Ser Pro Thr Gly Thr Ser Gly Tyr Asn Glu Gln Phe Phe
1               5                   10                  15
```

<210> SEQ ID NO 94
<211> LENGTH: 144
<212> TYPE: PRT
<213> ORGANISM: Homo sapiens

<400> SEQUENCE: 94

```
Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
                20                  25                  30

Val Ile Gln Ser Pro Arg His Leu Ile Lys Glu Lys Arg Glu Thr Ala
                35                  40                  45

Thr Leu Lys Cys Tyr Pro Ile Pro Arg His Asp Thr Val Tyr Trp Tyr
                50                  55                  60
```

```
Gln Gln Gly Pro Gly Gln Asp Pro Gln Phe Leu Ile Ser Phe Tyr Glu
 65                  70                  75                  80

Lys Met Gln Ser Asp Lys Gly Ser Ile Pro Asp Arg Phe Ser Ala Gln
                 85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Pro Thr Gly Thr Ser
        115                 120                 125

Gly Tyr Asn Glu Gln Phe Phe Gly Pro Gly Thr Arg Leu Thr Val Leu
    130                 135                 140
```

<210> SEQ ID NO 95
<211> LENGTH: 179
<212> TYPE: PRT
<213> ORGANISM: Homo sapiens

<400> SEQUENCE: 95

```
Glu Asp Leu Lys Asn Val Phe Pro Pro Glu Val Ala Val Phe Glu Pro
  1               5                  10                  15

Ser Glu Ala Glu Ile Ser His Thr Gln Lys Ala Thr Leu Val Cys Leu
                 20                  25                  30

Ala Thr Gly Phe Tyr Pro Asp His Val Glu Leu Ser Trp Trp Val Asn
             35                  40                  45

Gly Lys Glu Val His Ser Gly Val Ser Thr Asp Pro Gln Pro Leu Lys
         50                  55                  60

Glu Gln Pro Ala Leu Asn Asp Ser Arg Tyr Cys Leu Ser Ser Arg Leu
 65                  70                  75                  80

Arg Val Ser Ala Thr Phe Trp Gln Asn Pro Arg Asn His Phe Arg Cys
                 85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly
```

<210> SEQ ID NO 96
<211> LENGTH: 323
<212> TYPE: PRT
<213> ORGANISM: Homo sapiens

<400> SEQUENCE: 96

```
Met Leu Ser Pro Asp Leu Pro Asp Ser Ala Trp Asn Thr Arg Leu Leu
  1               5                  10                  15

Cys His Val Met Leu Cys Leu Leu Gly Ala Val Ser Val Ala Ala Gly
                 20                  25                  30

Val Ile Gln Ser Pro Arg His Leu Ile Lys Glu Lys Arg Glu Thr Ala
             35                  40                  45

Thr Leu Lys Cys Tyr Pro Ile Pro Arg His Asp Thr Val Tyr Trp Tyr
         50                  55                  60

Gln Gln Gly Pro Gly Gln Asp Pro Gln Phe Leu Ile Ser Phe Tyr Glu
```

```
                65                  70                  75                  80
Lys Met Gln Ser Asp Lys Gly Ser Ile Pro Asp Arg Phe Ser Ala Gln
                    85                  90                  95
Gln Phe Ser Asp Tyr His Ser Glu Leu Asn Met Ser Ser Leu Glu Leu
                    100                 105                 110
Gly Asp Ser Ala Leu Tyr Phe Cys Ala Ser Ser Pro Thr Gly Thr Ser
                    115                 120                 125
Gly Tyr Asn Glu Gln Phe Phe Gly Pro Gly Thr Arg Leu Thr Val Leu
                    130                 135                 140
Glu Asp Leu Lys Asn Val Phe Pro Pro Glu Val Ala Val Phe Glu Pro
145                 150                 155                 160
Ser Glu Ala Glu Ile Ser His Thr Gln Lys Ala Thr Leu Val Cys Leu
                    165                 170                 175
Ala Thr Gly Phe Tyr Pro Asp His Val Glu Leu Ser Trp Trp Val Asn
                    180                 185                 190
Gly Lys Glu Val His Ser Gly Val Ser Thr Asp Pro Gln Pro Leu Lys
                    195                 200                 205
Glu Gln Pro Ala Leu Asn Asp Ser Arg Tyr Cys Leu Ser Ser Arg Leu
                    210                 215                 220
Arg Val Ser Ala Thr Phe Trp Gln Asn Pro Arg Asn His Phe Arg Cys
225                 230                 235                 240
Gln Val Gln Phe Tyr Gly Leu Ser Glu Asn Asp Glu Trp Thr Gln Asp
                    245                 250                 255
Arg Ala Lys Pro Val Thr Gln Ile Val Ser Ala Glu Ala Trp Gly Arg
                    260                 265                 270
Ala Asp Cys Gly Phe Thr Ser Glu Ser Tyr Gln Gln Gly Val Leu Ser
                    275                 280                 285
Ala Thr Ile Leu Tyr Glu Ile Leu Leu Gly Lys Ala Thr Leu Tyr Ala
                    290                 295                 300
Val Leu Val Ser Ala Leu Val Leu Met Ala Met Val Lys Arg Lys Asp
305                 310                 315                 320
Ser Arg Gly

<210> SEQ ID NO 97
<211> LENGTH: 6
<212> TYPE: PRT
<213> ORGANISM: Homo sapiens

<400> SEQUENCE: 97

Ser Ser Asn Phe Tyr Ala
1               5

<210> SEQ ID NO 98
<211> LENGTH: 3
<212> TYPE: PRT
<213> ORGANISM: Homo sapiens

<400> SEQUENCE: 98

Met Thr Leu
1

<210> SEQ ID NO 99
<211> LENGTH: 11
<212> TYPE: PRT
<213> ORGANISM: Homo sapiens

<400> SEQUENCE: 99
```

Cys Ala Leu Asn Arg Asp Asp Lys Ile Ile Phe
1               5                   10

<210> SEQ ID NO 100
<211> LENGTH: 132
<212> TYPE: PRT
<213> ORGANISM: Homo sapiens

<400> SEQUENCE: 100

Met Glu Lys Asn Pro Leu Ala Ala Pro Leu Leu Ile Leu Trp Phe His
1               5                   10                  15

Leu Asp Cys Val Ser Ser Ile Leu Asn Val Glu Gln Ser Pro Gln Ser
            20                  25                  30

Leu His Val Gln Glu Gly Asp Ser Thr Asn Phe Thr Cys Ser Phe Pro
        35                  40                  45

Ser Ser Asn Phe Tyr Ala Leu His Trp Tyr Arg Trp Glu Thr Ala Lys
    50                  55                  60

Ser Pro Glu Ala Leu Phe Val Met Thr Leu Asn Gly Asp Glu Lys Lys
65                  70                  75                  80

Lys Gly Arg Ile Ser Ala Thr Leu Asn Thr Lys Glu Gly Tyr Ser Tyr
                85                  90                  95

Leu Tyr Ile Lys Gly Ser Gln Pro Glu Asp Ser Ala Thr Tyr Leu Cys
            100                 105                 110

Ala Leu Asn Arg Asp Asp Lys Ile Phe Gly Lys Gly Thr Arg Leu
            115                 120                 125

His Ile Leu Pro
        130

<210> SEQ ID NO 101
<211> LENGTH: 141
<212> TYPE: PRT
<213> ORGANISM: Homo sapiens

<400> SEQUENCE: 101

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 102
<211> LENGTH: 273
<212> TYPE: PRT
<213> ORGANISM: Homo sapiens

<400> SEQUENCE: 102

Met Glu Lys Asn Pro Leu Ala Ala Pro Leu Leu Ile Leu Trp Phe His
1               5                   10                  15

Leu Asp Cys Val Ser Ser Ile Leu Asn Val Glu Gln Ser Pro Gln Ser
            20                  25                  30

Leu His Val Gln Glu Gly Asp Ser Thr Asn Phe Thr Cys Ser Phe Pro
        35                  40                  45

Ser Ser Asn Phe Tyr Ala Leu His Trp Tyr Arg Trp Glu Thr Ala Lys
    50                  55                  60

Ser Pro Glu Ala Leu Phe Val Met Thr Leu Asn Gly Asp Glu Lys Lys
65                  70                  75                  80

Lys Gly Arg Ile Ser Ala Thr Leu Asn Thr Lys Glu Gly Tyr Ser Tyr
                85                  90                  95

Leu Tyr Ile Lys Gly Ser Gln Pro Glu Asp Ser Ala Thr Tyr Leu Cys
            100                 105                 110

Ala Leu Asn Arg Asp Asp Lys Ile Ile Phe Gly Lys Gly Thr Arg Leu
        115                 120                 125

His Ile Leu Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 103
<211> LENGTH: 5
<212> TYPE: PRT
<213> ORGANISM: Homo sapiens

<400> SEQUENCE: 103

Met Asp His Glu Asn
1               5

<210> SEQ ID NO 104
<211> LENGTH: 6
<212> TYPE: PRT
<213> ORGANISM: Homo sapiens

<400> SEQUENCE: 104

Ser Tyr Asp Val Lys Met
1               5

<210> SEQ ID NO 105

```
<211> LENGTH: 14
<212> TYPE: PRT
<213> ORGANISM: Homo sapiens

<400> SEQUENCE: 105

Cys Ala Ser Arg Leu Pro Ser Arg Thr Tyr Glu Gln Tyr Phe
1               5                   10

<210> SEQ ID NO 106
<211> LENGTH: 132
<212> TYPE: PRT
<213> ORGANISM: Homo sapiens

<400> SEQUENCE: 106

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
        50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Arg Leu Pro Ser Arg Thr Tyr Glu Gln Tyr Phe Gly Pro Gly Thr Arg
        115                 120                 125

Leu Thr Val Thr
    130

<210> SEQ ID NO 107
<211> LENGTH: 179
<212> TYPE: PRT
<213> ORGANISM: Homo sapiens

<400> SEQUENCE: 107

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
            35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
        130                 135                 140
```

```
Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 108
<211> LENGTH: 311
<212> TYPE: PRT
<213> ORGANISM: Homo sapiens

<400> SEQUENCE: 108

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Arg Leu Pro Ser Arg Thr Tyr Glu Gln Tyr Phe Gly Pro Gly Thr Arg
        115                 120                 125

Leu Thr Val Thr Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
290                 295                 300

Lys Arg Lys Asp Ser Arg Gly
305                 310

<210> SEQ ID NO 109
<211> LENGTH: 6
```

```
<212> TYPE: PRT
<213> ORGANISM: Homo sapiens

<400> SEQUENCE: 109

Asp Ser Ala Ile Tyr Asn
1               5

<210> SEQ ID NO 110
<211> LENGTH: 3
<212> TYPE: PRT
<213> ORGANISM: Homo sapiens

<400> SEQUENCE: 110

Ile Gln Ser
1

<210> SEQ ID NO 111
<211> LENGTH: 11
<212> TYPE: PRT
<213> ORGANISM: Homo sapiens

<400> SEQUENCE: 111

Cys Ala Val Asn Ser Asp Tyr Lys Leu Ser Phe
1               5                  10

<210> SEQ ID NO 112
<211> LENGTH: 129
<212> TYPE: PRT
<213> ORGANISM: Homo sapiens

<400> SEQUENCE: 112

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
                20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
        50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Asn
            100                 105                 110

Ser Asp Tyr Lys Leu Ser Phe Gly Ala Gly Thr Thr Val Thr Val Arg
        115                 120                 125

Ala

<210> SEQ ID NO 113
<211> LENGTH: 141
<212> TYPE: PRT
<213> ORGANISM: Homo sapiens

<400> SEQUENCE: 113

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
                20                  25                  30

Asn Val Ser Gln Ser Lys Asp Ser Asp Val Tyr Ile Thr Asp Lys Thr
```

```
            35                  40                  45
Val Leu Asp Met Arg Ser Met Asp Phe Lys Ser Asn Ser Ala Val Ala
 50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                 85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
130                 135                 140

<210> SEQ ID NO 114
<211> LENGTH: 270
<212> TYPE: PRT
<213> ORGANISM: Homo sapiens

<400> SEQUENCE: 114

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Asn
            100                 105                 110

Ser Asp Tyr Lys Leu Ser Phe Gly Ala Gly Thr Thr Val Thr Val Arg
        115                 120                 125

Ala Asn Ile Gln Asn Pro Asp Pro Ala Val Tyr Gln Leu Arg Asp Ser
130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270
```

<210> SEQ ID NO 115
<211> LENGTH: 5
<212> TYPE: PRT
<213> ORGANISM: Homo sapiens

<400> SEQUENCE: 115

Pro His Arg Asp Thr
1               5

<210> SEQ ID NO 116
<211> LENGTH: 6
<212> TYPE: PRT
<213> ORGANISM: Homo sapiens

<400> SEQUENCE: 116

Phe Tyr Glu Lys Met Gln
1               5

<210> SEQ ID NO 117
<211> LENGTH: 16
<212> TYPE: PRT
<213> ORGANISM: Homo sapiens

<400> SEQUENCE: 117

Cys Ala Ser Ser Leu Gly Leu Gly Thr Gly Asp Tyr Gly Tyr Thr Phe
1               5                   10                  15

<210> SEQ ID NO 118
<211> LENGTH: 144
<212> TYPE: PRT
<213> ORGANISM: Homo sapiens

<400> SEQUENCE: 118

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
                20                  25                  30

Val Ile Gln Ser Pro Arg His Leu Ile Lys Glu Lys Arg Glu Thr Ala
            35                  40                  45

Thr Leu Lys Cys Tyr Pro Ile Pro Arg His Asp Thr Val Tyr Trp Tyr
        50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Leu Gly Leu Gly Thr
        115                 120                 125

Gly Asp Tyr Gly Tyr Thr Phe Gly Ser Gly Thr Arg Leu Thr Val Val
    130                 135                 140

<210> SEQ ID NO 119
<211> LENGTH: 177
<212> TYPE: PRT
<213> ORGANISM: Homo sapiens

<400> SEQUENCE: 119

Glu Asp Leu Asn Lys Val Phe Pro Pro Glu Val Ala Val Phe Glu Pro
1               5                   10                  15

-continued

```
Ser Glu Ala Glu Ile Ser His Thr Gln Lys Ala Thr Leu Val Cys Leu
                20                  25                  30

Ala Thr Gly Phe Phe Pro Asp His Val Glu Leu Ser Trp Trp Val Asn
            35                  40                  45

Gly Lys Glu Val His Ser Gly Val Ser Thr Asp Pro Gln Pro Leu Lys
 50                  55                  60

Glu Gln Pro Ala Leu Asn Asp Ser Arg Tyr Cys Leu Ser Ser Arg Leu
 65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 120
<211> LENGTH: 321
<212> TYPE: PRT
<213> ORGANISM: Homo sapiens

<400> SEQUENCE: 120

Met Leu Ser Pro Asp Leu Pro Asp Ser Ala Trp Asn Thr Arg Leu Leu
 1               5                  10                  15

Cys His Val Met Leu Cys Leu Leu Gly Ala Val Ser Val Ala Ala Gly
                20                  25                  30

Val Ile Gln Ser Pro Arg His Leu Ile Lys Glu Lys Arg Glu Thr Ala
            35                  40                  45

Thr Leu Lys Cys Tyr Pro Ile Pro Arg His Asp Thr Val Tyr Trp Tyr
        50                  55                  60

Gln Gln Gly Pro Gly Gln Asp Pro Gln Phe Leu Ile Ser Phe Tyr Glu
 65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Leu Gly Leu Gly Thr
        115                 120                 125

Gly Asp Tyr Gly Tyr Thr Phe Gly Ser Gly Thr Arg Leu Thr Val Val
    130                 135                 140

Glu Asp Leu Asn Lys Val Phe Pro Pro Glu Val Ala Val Phe Glu Pro
145                 150                 155                 160

Ser Glu Ala Glu Ile Ser His Thr Gln Lys Ala Thr Leu Val Cys Leu
                165                 170                 175

Ala Thr Gly Phe Phe Pro Asp His Val Glu Leu Ser Trp Trp Val Asn
            180                 185                 190

Gly Lys Glu Val His Ser Gly Val Ser Thr Asp Pro Gln Pro Leu Lys
        195                 200                 205
```

Glu Gln Pro Ala Leu Asn Asp Ser Arg Tyr Cys Leu Ser Ser Arg Leu
        210                 215                 220

Arg Val Ser Ala Thr Phe Trp Gln Asn Pro Arg Asn His Phe Arg Cys
225                 230                 235                 240

Gln Val Gln Phe Tyr Gly Leu Ser Glu Asn Asp Glu Trp Thr Gln Asp
                245                 250                 255

Arg Ala Lys Pro Val Thr Gln Ile Val Ser Ala Glu Ala Trp Gly Arg
            260                 265                 270

Ala Asp Cys Gly Phe Thr Ser Val Ser Tyr Gln Gln Gly Val Leu Ser
        275                 280                 285

Ala Thr Ile Leu Tyr Glu Ile Leu Leu Gly Lys Ala Thr Leu Tyr Ala
        290                 295                 300

Val Leu Val Ser Ala Leu Val Leu Met Ala Met Val Lys Arg Lys Asp
305                 310                 315                 320

Phe

<210> SEQ ID NO 121
<211> LENGTH: 6
<212> TYPE: PRT
<213> ORGANISM: Homo sapiens

<400> SEQUENCE: 121

Asp Ser Ala Ile Tyr Asn
1               5

<210> SEQ ID NO 122
<211> LENGTH: 3
<212> TYPE: PRT
<213> ORGANISM: Homo sapiens

<400> SEQUENCE: 122

Ile Gln Ser
1

<210> SEQ ID NO 123
<211> LENGTH: 15
<212> TYPE: PRT
<213> ORGANISM: Homo sapiens

<400> SEQUENCE: 123

Cys Ala Val Arg Pro Thr Ser Gly Gly Ser Tyr Ile Pro Thr Phe
1               5                   10                  15

<210> SEQ ID NO 124
<211> LENGTH: 133
<212> TYPE: PRT
<213> ORGANISM: Homo sapiens

<400> SEQUENCE: 124

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

```
Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Pro Thr Ser Gly Gly Ser Tyr Ile Pro Thr Phe Gly Arg Gly Thr Ser
        115                 120                 125

Leu Ile Val His Pro
        130

<210> SEQ ID NO 125
<211> LENGTH: 141
<212> TYPE: PRT
<213> ORGANISM: Homo sapiens

<400> SEQUENCE: 125

Tyr Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
                20                  25                  30

Asn Val Ser Gln Ser Lys Asp Ser Asp Val Tyr Ile Thr Asp Lys Thr
            35                  40                  45

Val Leu Asp Met Arg Ser Met Asp Phe Lys Ser Asn Ser Ala Val Ala
50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
            115                 120                 125

Gly Phe Asn Leu Leu Met Thr Leu Arg Leu Trp Ser Ser
        130                 135                 140

<210> SEQ ID NO 126
<211> LENGTH: 274
<212> TYPE: PRT
<213> ORGANISM: Homo sapiens

<400> SEQUENCE: 126

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
                20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Pro Thr Ser Gly Gly Ser Tyr Ile Pro Thr Phe Gly Arg Gly Thr Ser
        115                 120                 125
```

Leu Ile Val His Pro Tyr Ile Gln Asn Pro Asp Pro Ala Val Tyr Gln
            130                 135                 140

Leu Arg Asp Ser Lys Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
                180                 185                 190

Asn Ser Ala Val Ala Trp Ser Asn Lys Ser Asp Phe Ala Cys Ala Asn
            195                 200                 205

Ala Phe Asn Asn Ser Ile Ile Pro Glu Asp Thr Phe Phe Pro Ser Pro
210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 127
<211> LENGTH: 5
<212> TYPE: PRT
<213> ORGANISM: Homo sapiens

<400> SEQUENCE: 127

Met Asn His Glu Tyr
1               5

<210> SEQ ID NO 128
<211> LENGTH: 6
<212> TYPE: PRT
<213> ORGANISM: Homo sapiens

<400> SEQUENCE: 128

Ser Val Gly Ala Gly Ile
1               5

<210> SEQ ID NO 129
<211> LENGTH: 14
<212> TYPE: PRT
<213> ORGANISM: Homo sapiens

<400> SEQUENCE: 129

Cys Ala Ser Ser Tyr Val Gly Asn Thr Gly Glu Leu Phe Phe
1               5                   10

<210> SEQ ID NO 130
<211> LENGTH: 132
<212> TYPE: PRT
<213> ORGANISM: Homo sapiens

<400> SEQUENCE: 130

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
                20                  25                  30

Lys Thr Gly Gln Ser Met Thr Leu Gln Cys Ala Gln Asp Met Asn His
            35                  40                  45

Glu Tyr Met Ser Trp Tyr Arg Gln Asp Pro Gly Met Gly Leu Arg Leu
            50                  55                  60

Ile His Tyr Ser Val Gly Ala Gly Ile Thr Asp Gln Gly Glu Val Pro
 65                  70                  75                  80

Asn Gly Tyr Asn Val Ser Arg Ser Thr Thr Glu Asp Phe Pro Leu Arg
                    85                  90                  95

Leu Leu Ser Ala Ala Pro Ser Gln Thr Ser Val Tyr Phe Cys Ala Ser
                100                 105                 110

Ser Tyr Val Gly Asn Thr Gly Glu Leu Phe Phe Gly Glu Gly Ser Arg
                115                 120                 125

Leu Thr Val Leu
    130

<210> SEQ ID NO 131
<211> LENGTH: 179
<212> TYPE: PRT
<213> ORGANISM: Homo sapiens

<400> SEQUENCE: 131

Glu Asp Leu Lys Asn Val Phe Pro Pro Glu Val Ala Val Phe Glu Pro
 1               5                  10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
                35                  40                  45

Gly Lys Glu Val His Ser Gly Val Ser Thr Asp Pro Gln Pro Leu Lys
 50                  55                  60

Glu Gln Pro Ala Leu Asn Asp Ser Arg Tyr Cys Leu Ser Ser Arg Leu
 65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
                115                 120                 125

Ala Asp Cys Gly Phe Thr Ser Glu Ser Tyr Gln Gln Gly Val Leu Ser
                130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 132
<211> LENGTH: 311
<212> TYPE: PRT
<213> ORGANISM: Homo sapiens

<400> SEQUENCE: 132

Met Ser Ile Gly Leu Leu Cys Cys Ala Ala Leu Ser Leu Leu Trp Ala
 1               5                  10                  15

Gly Pro Val Asn Ala Gly Val Thr Gln Thr Pro Lys Phe Gln Val Leu
                20                  25                  30

Lys Thr Gly Gln Ser Met Thr Leu Gln Cys Ala Gln Asp Met Asn His
                35                  40                  45

Glu Tyr Met Ser Trp Tyr Arg Gln Asp Pro Gly Met Gly Leu Arg Leu

```
                50                  55                  60
Ile His Tyr Ser Val Gly Ala Gly Ile Thr Asp Gln Gly Glu Val Pro
 65                  70                  75                  80

Asn Gly Tyr Asn Val Ser Arg Ser Thr Thr Glu Asp Phe Pro Leu Arg
                 85                  90                  95

Leu Leu Ser Ala Ala Pro Ser Gln Thr Ser Val Tyr Phe Cys Ala Ser
            100                 105                 110

Ser Tyr Val Gly Asn Thr Gly Glu Leu Phe Phe Gly Glu Gly Ser Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 133
<211> LENGTH: 9
<212> TYPE: PRT
<213> ORGANISM: Homo sapiens

<400> SEQUENCE: 133

Lys Val Leu Glu Tyr Val Ile Lys Val
1               5

<210> SEQ ID NO 134
<211> LENGTH: 9
<212> TYPE: PRT
<213> ORGANISM: Homo sapiens

<400> SEQUENCE: 134

Ala Val Leu Glu Tyr Val Ile Lys Val
1               5

<210> SEQ ID NO 135
<211> LENGTH: 9
<212> TYPE: PRT
<213> ORGANISM: Homo sapiens

<400> SEQUENCE: 135
```

```
Lys Ala Leu Glu Tyr Val Ile Lys Val
1               5
```

<210> SEQ ID NO 136
<211> LENGTH: 9
<212> TYPE: PRT
<213> ORGANISM: Homo sapiens

<400> SEQUENCE: 136

```
Lys Val Ala Glu Tyr Val Ile Lys Val
1               5
```

<210> SEQ ID NO 137
<211> LENGTH: 9
<212> TYPE: PRT
<213> ORGANISM: Homo sapiens

<400> SEQUENCE: 137

```
Lys Val Leu Ala Tyr Val Ile Lys Val
1               5
```

<210> SEQ ID NO 138
<211> LENGTH: 9
<212> TYPE: PRT
<213> ORGANISM: Homo sapiens

<400> SEQUENCE: 138

```
Lys Val Leu Glu Ala Val Ile Lys Val
1               5
```

<210> SEQ ID NO 139
<211> LENGTH: 9
<212> TYPE: PRT
<213> ORGANISM: Homo sapiens

<400> SEQUENCE: 139

```
Lys Val Leu Glu Tyr Ala Ile Lys Val
1               5
```

<210> SEQ ID NO 140
<211> LENGTH: 9
<212> TYPE: PRT
<213> ORGANISM: Homo sapiens

<400> SEQUENCE: 140

```
Lys Val Leu Glu Tyr Val Ala Lys Val
1               5
```

<210> SEQ ID NO 141
<211> LENGTH: 9
<212> TYPE: PRT
<213> ORGANISM: Homo sapiens

<400> SEQUENCE: 141

```
Lys Val Leu Glu Tyr Val Ile Ala Val
1               5
```

<210> SEQ ID NO 142
<211> LENGTH: 9
<212> TYPE: PRT
<213> ORGANISM: Homo sapiens

<400> SEQUENCE: 142

```
Lys Val Leu Glu Tyr Val Ile Lys Ala
```

```
<210> SEQ ID NO 143
<211> LENGTH: 9
<212> TYPE: PRT
<213> ORGANISM: Homo sapiens

<400> SEQUENCE: 143

Ile Leu Leu Pro Tyr Val Ser Lys Val
1               5

<210> SEQ ID NO 144
<211> LENGTH: 9
<212> TYPE: PRT
<213> ORGANISM: Homo sapiens

<400> SEQUENCE: 144

Lys Ala Leu Glu Gly Phe Ile Ala Val
1               5

<210> SEQ ID NO 145
<211> LENGTH: 9
<212> TYPE: PRT
<213> ORGANISM: Homo sapiens

<400> SEQUENCE: 145

Lys Leu Leu Glu Lys Val Arg Lys Val
1               5

<210> SEQ ID NO 146
<211> LENGTH: 9
<212> TYPE: PRT
<213> ORGANISM: Homo sapiens

<400> SEQUENCE: 146

Lys Leu Thr Glu Tyr Val Asp Lys Val
1               5

<210> SEQ ID NO 147
<211> LENGTH: 9
<212> TYPE: PRT
<213> ORGANISM: Homo sapiens

<400> SEQUENCE: 147

Lys Val Leu Glu Arg Val Asn Ala Val
1               5

<210> SEQ ID NO 148
<211> LENGTH: 9
<212> TYPE: PRT
<213> ORGANISM: Homo sapiens

<400> SEQUENCE: 148

Lys Val Leu Asn Lys Val Ile Thr Val
1               5

<210> SEQ ID NO 149
<211> LENGTH: 9
<212> TYPE: PRT
<213> ORGANISM: Homo sapiens

<400> SEQUENCE: 149

Lys Val Gln Glu Gln Val His Lys Val
1               5
```

```
<210> SEQ ID NO 150
<211> LENGTH: 9
<212> TYPE: PRT
<213> ORGANISM: Homo sapiens

<400> SEQUENCE: 150

Leu Leu Leu Pro Asp Val Ile Lys Val
1               5

<210> SEQ ID NO 151
<211> LENGTH: 9
<212> TYPE: PRT
<213> ORGANISM: Homo sapiens

<400> SEQUENCE: 151

Asn Val Leu Glu Ile Val Gln Lys Val
1               5

<210> SEQ ID NO 152
<211> LENGTH: 9
<212> TYPE: PRT
<213> ORGANISM: Homo sapiens

<400> SEQUENCE: 152

Ser Val Leu Glu Pro Val Ile Ser Val
1               5

<210> SEQ ID NO 153
<211> LENGTH: 9
<212> TYPE: PRT
<213> ORGANISM: Homo sapiens

<400> SEQUENCE: 153

Ser Leu Leu Met Trp Ile Thr Gln Val
1               5

<210> SEQ ID NO 154
<211> LENGTH: 9
<212> TYPE: PRT
<213> ORGANISM: Homo sapiens

<400> SEQUENCE: 154

Thr Val Leu Glu Tyr Val Ile Lys Val
1               5

<210> SEQ ID NO 155
<211> LENGTH: 9
<212> TYPE: PRT
<213> ORGANISM: Homo sapiens

<400> SEQUENCE: 155

Lys Thr Leu Glu Tyr Val Ile Lys Val
1               5

<210> SEQ ID NO 156
<211> LENGTH: 9
<212> TYPE: PRT
<213> ORGANISM: Homo sapiens

<400> SEQUENCE: 156

Lys Val Thr Glu Tyr Val Ile Lys Val
1               5

<210> SEQ ID NO 157
```

```
<211> LENGTH: 9
<212> TYPE: PRT
<213> ORGANISM: Homo sapiens

<400> SEQUENCE: 157

Lys Val Leu Thr Tyr Val Ile Lys Val
1               5

<210> SEQ ID NO 158
<211> LENGTH: 9
<212> TYPE: PRT
<213> ORGANISM: Homo sapiens

<400> SEQUENCE: 158

Lys Val Leu Glu Thr Val Ile Lys Val
1               5

<210> SEQ ID NO 159
<211> LENGTH: 9
<212> TYPE: PRT
<213> ORGANISM: Homo sapiens

<400> SEQUENCE: 159

Lys Val Leu Glu Tyr Thr Ile Lys Val
1               5

<210> SEQ ID NO 160
<211> LENGTH: 9
<212> TYPE: PRT
<213> ORGANISM: Homo sapiens

<400> SEQUENCE: 160

Lys Val Leu Glu Tyr Val Thr Lys Val
1               5

<210> SEQ ID NO 161
<211> LENGTH: 9
<212> TYPE: PRT
<213> ORGANISM: Homo sapiens

<400> SEQUENCE: 161

Lys Val Leu Glu Tyr Val Ile Thr Val
1               5

<210> SEQ ID NO 162
<211> LENGTH: 9
<212> TYPE: PRT
<213> ORGANISM: Homo sapiens

<400> SEQUENCE: 162

Lys Val Leu Glu Tyr Val Ile Lys Thr
1               5
```